US011426161B2

(12) United States Patent
Kostrzewski

(10) Patent No.: US 11,426,161 B2
(45) Date of Patent: Aug. 30, 2022

(54) ENDOSCOPIC STAPLER

(71) Applicant: Covidien LP, Mansfield, MA (US)

(72) Inventor: Stanislaw Kostrzewski, Newtown, CT (US)

(73) Assignee: Covidien LP, Mansfield, MA (US)

( * ) Notice: Subject to any disclaimer, the term of this patent is extended or adjusted under 35 U.S.C. 154(b) by 155 days.

(21) Appl. No.: 16/601,148

(22) Filed: Oct. 14, 2019

(65) Prior Publication Data

US 2020/0093490 A1 Mar. 26, 2020

Related U.S. Application Data

(63) Continuation of application No. 14/994,228, filed on Jan. 13, 2016, now Pat. No. 10,463,368.

(60) Provisional application No. 62/145,857, filed on Apr. 10, 2015.

(51) Int. Cl.
*A61B 17/072* (2006.01)
*A61B 17/064* (2006.01)
*A61B 17/00* (2006.01)

(52) U.S. Cl.
CPC .... *A61B 17/07207* (2013.01); *A61B 17/0644* (2013.01); *A61B 2017/0046* (2013.01); *A61B 2017/07228* (2013.01); *A61B 2017/07271* (2013.01); *A61B 2017/07278* (2013.01)

(58) Field of Classification Search
CPC .......... A61B 17/07207; A61B 17/0644; A61B 2017/07271; A61B 2017/07228; A61B 2017/07278; A61B 2017/0046; A61B 17/00234; A61B 17/064; A61B 2017/0645; A61B 2017/07221
See application file for complete search history.

(56) References Cited

U.S. PATENT DOCUMENTS

| 3,079,606 A | 3/1963 | Bobrov et al. |
| 3,490,675 A | 1/1970 | Green et al. |
| 3,499,591 A | 3/1970 | Green |

(Continued)

FOREIGN PATENT DOCUMENTS

| AU | 198654765 | 9/1986 |
| CA | 2773414 A1 | 11/2012 |

(Continued)

OTHER PUBLICATIONS

Japanese Office Action dated Jan. 24, 2020, issued in JP Appln. No. 2016-075711, 4 pages.

(Continued)

*Primary Examiner* — Thomas M Wittenschlaeger
*Assistant Examiner* — Katie L Gerth

(57) ABSTRACT

A surgical stapler is described herein which includes a shaft portion and a tool assembly supported on a distal end of the shaft portion. The tool assembly includes an anvil and a cartridge body which rotatably supports a plurality of staples within notches. At least one firing cam is provided to sequentially to engage and rotate each of the staples to fire the staples from the cartridge body. Each of the staples includes first and second legs axially offset from each other and interconnected by an intermediate portion. At least one firing cam is provided to sequentially to engage and rotate each of the staples to fire the staples from the cartridge body. The at least one firing cam includes axially offset cam members.

16 Claims, 27 Drawing Sheets

(56) References Cited

U.S. PATENT DOCUMENTS

| | | |
|---|---|---|
| 3,777,538 A | 12/1973 | Weatherly et al. |
| 3,882,854 A | 5/1975 | Hulka et al. |
| 4,027,510 A | 6/1977 | Hiltebrandt |
| 4,086,926 A | 5/1978 | Green et al. |
| 4,241,861 A | 12/1980 | Fleischer |
| 4,244,372 A | 1/1981 | Kapitanov et al. |
| 4,429,695 A | 2/1984 | Green |
| 4,505,414 A | 3/1985 | Filipi |
| 4,520,817 A | 6/1985 | Green |
| 4,589,413 A | 5/1986 | Malyshev et al. |
| 4,596,351 A | 6/1986 | Fedotov et al. |
| 4,602,634 A | 7/1986 | Barkley |
| 4,605,001 A | 8/1986 | Rothfuss et al. |
| 4,608,981 A | 9/1986 | Rothfuss et al. |
| 4,610,383 A | 9/1986 | Rothfuss et al. |
| 4,633,861 A | 1/1987 | Chow et al. |
| 4,633,874 A | 1/1987 | Chow et al. |
| 4,671,445 A | 6/1987 | Barker et al. |
| 4,700,703 A | 10/1987 | Resnick et al. |
| 4,703,887 A | 11/1987 | Clanton et al. |
| 4,728,020 A | 3/1988 | Green et al. |
| 4,752,024 A | 6/1988 | Green et al. |
| 4,784,137 A | 11/1988 | Kulik et al. |
| 4,863,088 A | 9/1989 | Redmond et al. |
| 4,869,415 A | 9/1989 | Fox |
| 4,892,244 A | 1/1990 | Fox et al. |
| 4,955,959 A | 9/1990 | Tompkins et al. |
| 4,978,049 A | 12/1990 | Green |
| 4,991,764 A | 2/1991 | Mericle |
| 5,014,899 A | 5/1991 | Presty et al. |
| 5,031,814 A | 7/1991 | Tompkins et al. |
| 5,040,715 A | 8/1991 | Green et al. |
| 5,065,929 A | 11/1991 | Schulze et al. |
| 5,071,430 A | 12/1991 | de Salis et al. |
| 5,074,454 A | 12/1991 | Peters |
| 5,083,695 A | 1/1992 | Foslien et al. |
| 5,084,057 A | 1/1992 | Green et al. |
| 5,106,008 A | 4/1992 | Tompkins et al. |
| 5,111,987 A | 5/1992 | Moeinzadeh et al. |
| 5,129,570 A | 7/1992 | Schulze et al. |
| 5,141,144 A | 8/1992 | Foslien et al. |
| 5,156,315 A | 10/1992 | Green et al. |
| 5,156,614 A | 10/1992 | Green et al. |
| 5,163,943 A | 11/1992 | Mohiuddin et al. |
| 5,170,925 A | 12/1992 | Madden et al. |
| 5,171,247 A | 12/1992 | Hughett et al. |
| 5,173,133 A | 12/1992 | Morin et al. |
| 5,180,092 A | 1/1993 | Crainich |
| 5,188,274 A | 2/1993 | Moeinzadeh et al. |
| 5,220,928 A | 6/1993 | Oddsen et al. |
| 5,221,036 A | 6/1993 | Takase |
| 5,242,457 A | 9/1993 | Akopov et al. |
| 5,246,156 A | 9/1993 | Rothfuss et al. |
| 5,253,793 A | 10/1993 | Green et al. |
| 5,263,629 A | 11/1993 | Trumbull et al. |
| RE34,519 E | 1/1994 | Fox et al. |
| 5,275,323 A | 1/1994 | Schulze et al. |
| 5,282,807 A | 2/1994 | Knoepfler |
| 5,289,963 A | 3/1994 | McGarry et al. |
| 5,307,976 A | 5/1994 | Olson et al. |
| 5,308,576 A | 5/1994 | Green et al. |
| 5,312,023 A | 5/1994 | Green et al. |
| 5,318,221 A | 6/1994 | Green et al. |
| 5,326,013 A | 7/1994 | Green et al. |
| 5,328,077 A | 7/1994 | Lou |
| 5,330,486 A | 7/1994 | Wilk |
| 5,332,142 A | 7/1994 | Robinson et al. |
| 5,336,232 A | 8/1994 | Green et al. |
| 5,344,061 A | 9/1994 | Crainich |
| 5,352,238 A | 10/1994 | Green et al. |
| 5,356,064 A | 10/1994 | Green et al. |
| 5,358,506 A | 10/1994 | Green et al. |
| 5,364,001 A | 11/1994 | Bryan |
| 5,364,002 A | 11/1994 | Green et al. |
| 5,364,003 A | 11/1994 | Williamson, IV |
| 5,366,133 A | 11/1994 | Geiste |
| 5,376,095 A | 12/1994 | Ortiz |
| 5,379,933 A | 1/1995 | Green et al. |
| 5,381,943 A | 1/1995 | Allen et al. |
| 5,382,255 A | 1/1995 | Castro et al. |
| 5,383,880 A | 1/1995 | Hooven |
| 5,389,098 A | 2/1995 | Tsuruta et al. |
| 5,395,033 A | 3/1995 | Byrne et al. |
| 5,395,034 A | 3/1995 | Allen et al. |
| 5,397,046 A | 3/1995 | Savage et al. |
| 5,397,324 A | 3/1995 | Carroll et al. |
| 5,403,312 A | 4/1995 | Yates et al. |
| 5,405,072 A | 4/1995 | Zlock et al. |
| 5,407,293 A | 4/1995 | Crainich |
| 5,413,268 A | 5/1995 | Green et al. |
| 5,415,334 A | 5/1995 | Williamson et al. |
| 5,415,335 A | 5/1995 | Knodell, Jr. |
| 5,417,361 A | 5/1995 | Williamson, IV |
| 5,423,471 A | 6/1995 | Mastri et al. |
| 5,425,745 A | 6/1995 | Green et al. |
| 5,431,322 A | 7/1995 | Green et al. |
| 5,431,323 A | 7/1995 | Smith et al. |
| 5,433,721 A | 7/1995 | Hooven et al. |
| 5,441,193 A | 8/1995 | Gravener |
| 5,445,304 A | 8/1995 | Plyley et al. |
| 5,447,265 A | 9/1995 | Vidal et al. |
| 5,452,837 A | 9/1995 | Williamson, IV et al. |
| 5,456,401 A | 10/1995 | Green et al. |
| 5,464,300 A | 11/1995 | Crainich |
| 5,465,895 A | 11/1995 | Knodel et al. |
| 5,467,911 A | 11/1995 | Tsuruta et al. |
| 5,470,007 A | 11/1995 | Plyley et al. |
| 5,470,010 A | 11/1995 | Rothfuss et al. |
| 5,472,132 A | 12/1995 | Savage et al. |
| 5,474,566 A | 12/1995 | Alesi et al. |
| 5,476,206 A | 12/1995 | Green et al. |
| 5,478,003 A | 12/1995 | Green et al. |
| 5,480,089 A | 1/1996 | Blewett |
| 5,482,197 A | 1/1996 | Green et al. |
| 5,484,095 A | 1/1996 | Green et al. |
| 5,484,451 A * | 1/1996 | Akopov ............... A61B 17/04 227/175.1 |
| 5,485,947 A | 1/1996 | Olson et al. |
| 5,485,952 A | 1/1996 | Fontayne |
| 5,486,185 A | 1/1996 | Freitas et al. |
| 5,487,499 A | 1/1996 | Sorrentino et al. |
| 5,487,500 A | 1/1996 | Knodel et al. |
| 5,489,058 A | 2/1996 | Plyley et al. |
| 5,490,856 A | 2/1996 | Person et al. |
| 5,497,933 A | 3/1996 | DeFonzo et al. |
| 5,501,689 A | 3/1996 | Green et al. |
| 5,505,363 A | 4/1996 | Green et al. |
| 5,507,426 A | 4/1996 | Young et al. |
| 5,518,163 A | 5/1996 | Hooven |
| 5,518,164 A | 5/1996 | Hooven |
| 5,529,235 A | 6/1996 | Boiarski et al. |
| 5,531,744 A | 7/1996 | Nardella et al. |
| 5,535,934 A | 7/1996 | Boiarski et al. |
| 5,535,935 A | 7/1996 | Vidal et al. |
| 5,535,937 A | 7/1996 | Boiarski et al. |
| 5,540,375 A | 7/1996 | Bolanos et al. |
| 5,542,594 A | 8/1996 | McKean et al. |
| 5,549,628 A | 8/1996 | Cooper et al. |
| 5,551,622 A | 9/1996 | Yoon |
| 5,553,765 A | 9/1996 | Knodel et al. |
| 5,554,164 A | 9/1996 | Wilson et al. |
| 5,554,169 A | 9/1996 | Green et al. |
| 5,560,530 A | 10/1996 | Bolanos et al. |
| 5,560,532 A | 10/1996 | DeFonzo et al. |
| 5,562,239 A | 10/1996 | Boiarski et al. |
| 5,562,241 A | 10/1996 | Knodel et al. |
| 5,562,682 A | 10/1996 | Oberlin et al. |
| 5,562,701 A | 10/1996 | Huitema et al. |
| 5,564,615 A | 10/1996 | Bishop et al. |
| 5,571,116 A | 11/1996 | Bolanos et al. |
| 5,573,169 A | 11/1996 | Green et al. |
| 5,573,543 A | 11/1996 | Akopov et al. |
| 5,575,799 A | 11/1996 | Bolanos et al. |
| 5,575,803 A | 11/1996 | Cooper et al. |

(56) References Cited

U.S. PATENT DOCUMENTS

| | | |
|---|---|---|
| 5,577,654 A | 11/1996 | Bishop |
| 5,584,425 A | 12/1996 | Savage et al. |
| 5,586,711 A | 12/1996 | Plyley et al. |
| 5,588,580 A | 12/1996 | Paul et al. |
| 5,588,581 A | 12/1996 | Conlon et al. |
| 5,597,107 A | 1/1997 | Knodel et al. |
| 5,601,224 A | 2/1997 | Bishop et al. |
| 5,607,095 A | 3/1997 | Smith et al. |
| 5,615,820 A | 4/1997 | Viola |
| 5,618,291 A | 4/1997 | Thompson et al. |
| 5,624,452 A | 4/1997 | Yates |
| 5,626,587 A | 5/1997 | Bishop et al. |
| 5,628,446 A | 5/1997 | Geiste et al. |
| 5,630,539 A | 5/1997 | Plyley et al. |
| 5,630,540 A | 5/1997 | Blewett |
| 5,630,541 A | 5/1997 | Williamson, IV et al. |
| 5,632,432 A | 5/1997 | Schulze et al. |
| 5,634,584 A | 6/1997 | Okorocha et al. |
| 5,636,780 A | 6/1997 | Green et al. |
| 5,645,209 A | 7/1997 | Green et al. |
| 5,647,526 A | 7/1997 | Green et al. |
| 5,651,491 A | 7/1997 | Heaton et al. |
| 5,653,373 A | 8/1997 | Green et al. |
| 5,653,374 A | 8/1997 | Young et al. |
| 5,653,721 A | 8/1997 | Knodel et al. |
| 5,655,698 A | 8/1997 | Yoon |
| 5,657,921 A | 8/1997 | Young et al. |
| 5,658,300 A | 8/1997 | Bito et al. |
| 5,662,258 A | 9/1997 | Knodel et al. |
| 5,662,259 A | 9/1997 | Yoon |
| 5,662,260 A | 9/1997 | Yoon |
| 5,662,662 A | 9/1997 | Bishop et al. |
| 5,662,666 A | 9/1997 | Onuki et al. |
| 5,665,085 A | 9/1997 | Nardella |
| 5,667,517 A | 9/1997 | Hooven |
| 5,669,544 A | 9/1997 | Schulze et al. |
| 5,673,840 A | 10/1997 | Schulze et al. |
| 5,673,841 A | 10/1997 | Schulze et al. |
| 5,673,842 A | 10/1997 | Billner et al. |
| 5,676,674 A | 10/1997 | Bolanos et al. |
| 5,680,981 A | 10/1997 | Mililli et al. |
| 5,680,982 A | 10/1997 | Schulze et al. |
| 5,680,983 A | 10/1997 | Plyley et al. |
| 5,690,269 A | 11/1997 | Bolanos et al. |
| 5,690,675 A | 11/1997 | Sawyer et al. |
| 5,692,668 A | 12/1997 | Schulze et al. |
| 5,697,542 A | 12/1997 | Knodel et al. |
| 5,702,409 A | 12/1997 | Rayburn et al. |
| 5,704,534 A | 1/1998 | Huitema et al. |
| 5,706,997 A | 1/1998 | Green et al. |
| 5,709,334 A | 1/1998 | Sorrentino et al. |
| 5,711,472 A | 1/1998 | Bryan |
| 5,713,505 A | 2/1998 | Huitema |
| 5,715,988 A | 2/1998 | Palmer |
| 5,716,366 A | 2/1998 | Yates |
| 5,718,359 A | 2/1998 | Palmer et al. |
| 5,725,536 A | 3/1998 | Oberlin et al. |
| 5,725,554 A | 3/1998 | Simon et al. |
| 5,728,110 A | 3/1998 | Vidal et al. |
| 5,732,806 A | 3/1998 | Foshee et al. |
| 5,735,848 A | 4/1998 | Yates et al. |
| 5,743,456 A | 4/1998 | Jones et al. |
| 5,749,893 A | 5/1998 | Vidal et al. |
| 5,752,644 A | 5/1998 | Bolanos et al. |
| 5,762,255 A | 6/1998 | Chrisman et al. |
| 5,762,256 A | 6/1998 | Mastri et al. |
| 5,769,303 A | 6/1998 | Knodel et al. |
| 5,769,892 A | 6/1998 | Kingwell |
| 5,772,099 A | 6/1998 | Gravener |
| 5,772,673 A | 6/1998 | Cuny et al. |
| 5,779,130 A | 7/1998 | Alesi et al. |
| 5,779,131 A | 7/1998 | Knodel et al. |
| 5,779,132 A | 7/1998 | Knodel et al. |
| 5,782,396 A | 7/1998 | Mastri et al. |
| 5,782,397 A | 7/1998 | Koukline |
| 5,782,834 A | 7/1998 | Lucey et al. |
| 5,785,232 A | 7/1998 | Vidal et al. |
| 5,797,536 A | 8/1998 | Smith et al. |
| 5,797,537 A | 8/1998 | Oberlin et al. |
| 5,797,538 A | 8/1998 | Heaton et al. |
| 5,810,811 A | 9/1998 | Yates et al. |
| 5,810,855 A | 9/1998 | Rayburn et al. |
| 5,814,055 A | 9/1998 | Knodel et al. |
| 5,814,057 A | 9/1998 | Oi et al. |
| 5,816,471 A | 10/1998 | Plyley et al. |
| 5,817,109 A | 10/1998 | McGarry et al. |
| 5,820,009 A | 10/1998 | Melling et al. |
| 5,823,066 A | 10/1998 | Huitema et al. |
| 5,826,776 A | 10/1998 | Schulze et al. |
| 5,829,662 A | 11/1998 | Allen et al. |
| 5,833,695 A | 11/1998 | Yoon |
| 5,836,147 A | 11/1998 | Schnipke |
| 5,862,972 A | 1/1999 | Green et al. |
| 5,865,361 A | 2/1999 | Milliman et al. |
| 5,871,135 A | 2/1999 | Williamson IV et al. |
| 5,873,873 A | 2/1999 | Smith et al. |
| 5,878,938 A | 3/1999 | Bittner et al. |
| 5,893,506 A | 4/1999 | Powell |
| 5,894,979 A | 4/1999 | Powell |
| 5,897,562 A | 4/1999 | Bolanos et al. |
| 5,901,895 A | 5/1999 | Heaton et al. |
| 5,911,352 A | 6/1999 | Racenet et al. |
| 5,911,353 A | 6/1999 | Bolanos et al. |
| 5,918,791 A | 7/1999 | Sorrentino et al. |
| 5,919,198 A | 7/1999 | Graves, Jr. et al. |
| 5,922,001 A | 7/1999 | Yoon |
| 5,931,847 A | 8/1999 | Billner et al. |
| 5,941,442 A | 8/1999 | Geiste et al. |
| 5,954,259 A | 9/1999 | Viola et al. |
| 5,964,774 A | 10/1999 | McKean et al. |
| 5,980,510 A | 11/1999 | Tsonton et al. |
| 5,988,479 A | 11/1999 | Palmer |
| 6,004,335 A | 12/1999 | Vaitekunas et al. |
| 6,010,054 A | 1/2000 | Johnson et al. |
| 6,032,849 A | 3/2000 | Mastri et al. |
| 6,045,560 A | 4/2000 | McKean et al. |
| 6,063,097 A | 5/2000 | Oi et al. |
| 6,079,606 A | 6/2000 | Milliman et al. |
| 6,099,551 A | 8/2000 | Gabbay |
| 6,109,500 A | 8/2000 | Alli et al. |
| 6,131,789 A | 10/2000 | Schulze et al. |
| 6,131,790 A | 10/2000 | Piraka |
| 6,155,473 A | 12/2000 | Tompkins et al. |
| 6,197,017 B1 | 3/2001 | Brock et al. |
| 6,202,914 B1 | 3/2001 | Geiste et al. |
| 6,241,139 B1 | 6/2001 | Milliman et al. |
| 6,250,532 B1 | 6/2001 | Green et al. |
| 6,264,086 B1 | 7/2001 | McGuckin, Jr. |
| 6,264,087 B1 | 7/2001 | Whitman |
| 6,279,809 B1 | 8/2001 | Nicolo |
| 6,315,183 B1 | 11/2001 | Piraka |
| 6,315,184 B1 | 11/2001 | Whitman |
| 6,325,810 B1 | 12/2001 | Hamilton et al. |
| 6,330,965 B1 | 12/2001 | Milliman et al. |
| 6,391,038 B2 | 5/2002 | Vargas et al. |
| 6,398,797 B2 | 6/2002 | Bombard et al. |
| 6,436,097 B1 | 8/2002 | Nardella |
| 6,439,446 B1 | 8/2002 | Perry et al. |
| 6,443,973 B1 | 9/2002 | Whitman |
| 6,478,804 B2 | 11/2002 | Vargas et al. |
| 6,488,196 B1 | 12/2002 | Fenton, Jr. |
| 6,503,257 B2 | 1/2003 | Grant et al. |
| 6,505,768 B2 | 1/2003 | Whitman |
| 6,544,274 B2 | 4/2003 | Danitz et al. |
| 6,554,844 B2 | 4/2003 | Lee et al. |
| 6,565,554 B1 | 5/2003 | Niemeyer |
| 6,587,750 B2 | 7/2003 | Gerbi et al. |
| 6,592,597 B2 | 7/2003 | Grant et al. |
| 6,594,552 B1 | 7/2003 | Nowlin et al. |
| 6,602,252 B2 | 8/2003 | Mollenauer |
| 6,619,529 B2 | 9/2003 | Green et al. |
| D480,808 S | 10/2003 | Wells et al. |
| 6,644,532 B2 | 11/2003 | Green et al. |
| 6,656,193 B2 | 12/2003 | Grant et al. |

(56) References Cited

U.S. PATENT DOCUMENTS

| | | |
|---|---|---|
| 6,669,073 B2 | 12/2003 | Milliman et al. |
| 6,681,978 B2 | 1/2004 | Geiste et al. |
| 6,698,643 B2 | 3/2004 | Whitman |
| 6,716,232 B1 | 4/2004 | Vidal et al. |
| 6,722,552 B2 | 4/2004 | Fenton, Jr. |
| 6,755,338 B2 | 6/2004 | Hahnen et al. |
| 6,783,524 B2 | 8/2004 | Anderson et al. |
| 6,786,382 B1 | 9/2004 | Hoffman |
| 6,817,509 B2 | 11/2004 | Geiste et al. |
| 6,830,174 B2 | 12/2004 | Hillstead et al. |
| 6,835,199 B2 | 12/2004 | McGuckin, Jr. et al. |
| 6,843,403 B2 | 1/2005 | Whitman |
| RE38,708 E | 3/2005 | Bolanos et al. |
| 6,877,647 B2 | 4/2005 | Green et al. |
| 6,889,116 B2 | 5/2005 | Jinno |
| 6,905,057 B2 | 6/2005 | Swayze et al. |
| 6,945,444 B2 | 9/2005 | Gresham et al. |
| 6,953,138 B1 | 10/2005 | Dworak et al. |
| 6,953,139 B2 | 10/2005 | Milliman et al. |
| 6,959,852 B2 | 11/2005 | Shelton, IV et al. |
| 6,962,594 B1 | 11/2005 | Thevenet |
| 6,964,363 B2 | 11/2005 | Wales et al. |
| 6,978,921 B2 | 12/2005 | Shelton, IV et al. |
| 6,981,628 B2 | 1/2006 | Wales |
| 6,986,451 B1 | 1/2006 | Mastri et al. |
| 6,988,649 B2 | 1/2006 | Shelton, IV et al. |
| 6,991,627 B2 | 1/2006 | Madhani et al. |
| 6,994,714 B2 | 2/2006 | Vargas et al. |
| 7,000,818 B2 | 2/2006 | Shelton, IV et al. |
| 7,000,819 B2 | 2/2006 | Swayze et al. |
| 7,032,799 B2 | 4/2006 | Viola et al. |
| 7,044,352 B2 | 5/2006 | Shelton, IV et al. |
| 7,044,353 B2 | 5/2006 | Mastri et al. |
| 7,055,730 B2 | 6/2006 | Ehrenfels et al. |
| 7,055,731 B2 | 6/2006 | Shelton, IV et al. |
| 7,059,508 B2 | 6/2006 | Shelton, IV et al. |
| 7,070,083 B2 | 7/2006 | Jankowski |
| 7,083,075 B2 | 8/2006 | Swayze et al. |
| 7,097,089 B2 | 8/2006 | Marczyk |
| 7,111,769 B2 | 9/2006 | Wales et al. |
| 7,114,642 B2 | 10/2006 | Whitman |
| 7,121,446 B2 | 10/2006 | Arad et al. |
| 7,128,253 B2 | 10/2006 | Mastri et al. |
| 7,128,254 B2 | 10/2006 | Shelton, IV et al. |
| 7,140,527 B2 | 11/2006 | Ehrenfels et al. |
| 7,140,528 B2 | 11/2006 | Shelton, IV |
| 7,143,923 B2 | 12/2006 | Shelton, IV et al. |
| 7,143,924 B2 | 12/2006 | Scirica et al. |
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |
| 7,159,750 B2 | 1/2007 | Racenet et al. |
| 7,168,604 B2 | 1/2007 | Milliman et al. |
| 7,172,104 B2 | 2/2007 | Scirica et al. |
| 7,188,758 B2 | 3/2007 | Viola et al. |
| 7,207,471 B2 | 4/2007 | Heinrich et al. |
| 7,213,736 B2 | 5/2007 | Wales et al. |
| 7,225,963 B2 | 6/2007 | Scirica |
| 7,225,964 B2 | 6/2007 | Mastri et al. |
| 7,238,195 B2 | 7/2007 | Viola |
| 7,246,734 B2 | 7/2007 | Shelton, IV |
| 7,258,262 B2 | 8/2007 | Mastri et al. |
| 7,267,682 B1 | 9/2007 | Bender et al. |
| 7,278,562 B2 | 10/2007 | Mastri et al. |
| 7,278,563 B1 | 10/2007 | Green |
| 7,287,682 B1 | 10/2007 | Ezzat et al. |
| 7,293,685 B2 | 11/2007 | Ehrenfels et al. |
| 7,296,722 B2 | 11/2007 | Ivanko |
| 7,296,724 B2 | 11/2007 | Green et al. |
| 7,296,772 B2 | 11/2007 | Wang |
| 7,300,444 B1 | 11/2007 | Nielsen et al. |
| 7,303,107 B2 | 12/2007 | Milliman et al. |
| 7,303,108 B2 | 12/2007 | Shelton, IV |
| 7,308,998 B2 | 12/2007 | Mastri et al. |
| 7,326,232 B2 | 2/2008 | Viola et al. |
| 7,328,828 B2 | 2/2008 | Ortiz et al. |
| 7,328,829 B2 | 2/2008 | Arad et al. |
| 7,334,717 B2 | 2/2008 | Rethy et al. |
| 7,354,447 B2 | 4/2008 | Shelton, IV et al. |
| 7,357,287 B2 | 4/2008 | Shelton, IV et al. |
| 7,364,061 B2 | 4/2008 | Swayze et al. |
| 7,367,485 B2 | 5/2008 | Shelton, IV et al. |
| 7,377,928 B2 | 5/2008 | Zubik et al. |
| 7,380,695 B2 | 6/2008 | Doll et al. |
| 7,380,696 B2 | 6/2008 | Shelton, IV et al. |
| 7,396,356 B2 | 7/2008 | Mollenauer |
| 7,398,907 B2 | 7/2008 | Racenet et al. |
| 7,399,310 B2 | 7/2008 | Edoga et al. |
| 7,401,720 B1 | 7/2008 | Durrani |
| 7,401,721 B2 | 7/2008 | Holsten et al. |
| 7,404,508 B2 | 7/2008 | Smith et al. |
| 7,404,509 B2 | 7/2008 | Ortiz et al. |
| 7,407,074 B2 | 8/2008 | Ortiz et al. |
| 7,407,075 B2 | 8/2008 | Holsten et al. |
| 7,407,077 B2 | 8/2008 | Ortiz et al. |
| 7,407,078 B2 | 8/2008 | Shelton, IV et al. |
| 7,416,101 B2 | 8/2008 | Shelton, IV et al. |
| 7,419,080 B2 | 9/2008 | Smith et al. |
| 7,419,081 B2 | 9/2008 | Ehrenfels et al. |
| 7,419,495 B2 | 9/2008 | Menn et al. |
| 7,422,139 B2 | 9/2008 | Shelton, IV et al. |
| 7,424,965 B2 | 9/2008 | Racenet et al. |
| 7,431,189 B2 | 10/2008 | Shelton, IV et al. |
| 7,431,730 B2 | 10/2008 | Viola |
| 7,434,715 B2 | 10/2008 | Shelton, IV et al. |
| 7,434,717 B2 | 10/2008 | Shelton, IV et al. |
| 7,438,208 B2 | 10/2008 | Larson |
| 7,438,209 B1 | 10/2008 | Hess et al. |
| 7,441,684 B2 | 10/2008 | Shelton, IV et al. |
| 7,441,685 B1 | 10/2008 | Boudreaux |
| 7,448,525 B2 | 11/2008 | Shelton, IV et al. |
| 7,451,904 B2 | 11/2008 | Shelton, IV |
| 7,455,208 B2 | 11/2008 | Wales et al. |
| 7,455,676 B2 | 11/2008 | Holsten et al. |
| 7,458,494 B2 | 12/2008 | Matsutani et al. |
| 7,461,767 B2 | 12/2008 | Viola et al. |
| 7,462,185 B1 | 12/2008 | Knodel |
| 7,464,846 B2 | 12/2008 | Shelton, IV et al. |
| 7,464,847 B2 | 12/2008 | Viola et al. |
| 7,464,848 B2 | 12/2008 | Green et al. |
| 7,464,849 B2 | 12/2008 | Shelton, IV et al. |
| 7,467,740 B2 | 12/2008 | Shelton, IV et al. |
| 7,472,814 B2 | 1/2009 | Mastri et al. |
| 7,472,815 B2 | 1/2009 | Shelton, IV et al. |
| 7,472,816 B2 | 1/2009 | Holsten et al. |
| 7,473,258 B2 | 1/2009 | Clauson et al. |
| 7,481,347 B2 | 1/2009 | Roy |
| 7,481,348 B2 | 1/2009 | Marczyk |
| 7,481,349 B2 | 1/2009 | Holsten et al. |
| 7,481,824 B2 | 1/2009 | Boudreaux et al. |
| 7,487,899 B2 | 2/2009 | Shelton, IV et al. |
| 7,490,749 B2 | 2/2009 | Schall et al. |
| 7,494,039 B2 | 2/2009 | Racenet et al. |
| 7,500,979 B2 | 3/2009 | Hueil et al. |
| 7,503,474 B2 | 3/2009 | Hillstead et al. |
| 7,506,790 B2 | 3/2009 | Shelton, IV |
| 7,506,791 B2 | 3/2009 | Omaits et al. |
| 7,510,107 B2 | 3/2009 | Timm et al. |
| 7,513,408 B2 | 4/2009 | Shelton, IV et al. |
| 7,517,356 B2 | 4/2009 | Heinrich |
| 7,537,602 B2 | 5/2009 | Whitman |
| 7,543,729 B2 | 6/2009 | Ivanko |
| 7,543,730 B1 | 6/2009 | Marczyk |
| 7,543,731 B2 | 6/2009 | Green et al. |
| 7,552,854 B2 | 6/2009 | Wixey et al. |
| 7,556,185 B2 | 7/2009 | Viola |
| 7,556,186 B2 | 7/2009 | Milliman |
| 7,559,450 B2 | 7/2009 | Wales et al. |
| 7,559,452 B2 | 7/2009 | Wales et al. |
| 7,559,453 B2 | 7/2009 | Heinrich et al. |
| 7,559,937 B2 | 7/2009 | de la Torre et al. |
| 7,565,993 B2 | 7/2009 | Milliman et al. |
| 7,568,603 B2 | 8/2009 | Shelton, IV et al. |
| 7,568,604 B2 | 8/2009 | Ehrenfels et al. |

(56) References Cited

U.S. PATENT DOCUMENTS

| | | |
|---|---|---|
| 7,571,845 B2 | 8/2009 | Viola |
| 7,575,144 B2 | 8/2009 | Ortiz et al. |
| 7,584,880 B2 | 9/2009 | Racenet et al. |
| 7,588,174 B2 | 9/2009 | Holsten et al. |
| 7,588,175 B2 | 9/2009 | Timm et al. |
| 7,588,176 B2 | 9/2009 | Timm et al. |
| 7,588,177 B2 | 9/2009 | Racenet |
| 7,597,229 B2 | 10/2009 | Boudreaux et al. |
| 7,597,230 B2 | 10/2009 | Racenet et al. |
| 7,600,663 B2 | 10/2009 | Green |
| 7,604,150 B2 | 10/2009 | Boudreaux |
| 7,604,151 B2 | 10/2009 | Hess et al. |
| 7,607,557 B2 | 10/2009 | Shelton, IV et al. |
| 7,611,038 B2 | 11/2009 | Racenet et al. |
| 7,617,961 B2 | 11/2009 | Viola |
| 7,624,902 B2 | 12/2009 | Marczyk et al. |
| 7,624,903 B2 | 12/2009 | Green et al. |
| 7,631,793 B2 | 12/2009 | Rethy et al. |
| 7,631,794 B2 | 12/2009 | Rethy et al. |
| 7,635,073 B2 | 12/2009 | Heinrich |
| 7,635,074 B2 | 12/2009 | Olson et al. |
| 7,635,373 B2 | 12/2009 | Ortiz |
| 7,637,409 B2 | 12/2009 | Marczyk |
| 7,637,410 B2 | 12/2009 | Marczyk |
| 7,641,091 B2 | 1/2010 | Olson et al. |
| 7,641,095 B2 | 1/2010 | Viola |
| 7,644,848 B2 | 1/2010 | Swayze et al. |
| 7,648,055 B2 | 1/2010 | Marczyk |
| 7,651,017 B2 | 1/2010 | Ortiz et al. |
| 7,654,431 B2 | 2/2010 | Hueil et al. |
| 7,658,311 B2 | 2/2010 | Boudreaux |
| 7,658,312 B2 | 2/2010 | Vidal et al. |
| 7,665,646 B2 | 2/2010 | Prommersberger |
| 7,665,647 B2 | 2/2010 | Shelton, IV et al. |
| 7,669,746 B2 | 3/2010 | Shelton, IV |
| 7,670,334 B2 | 3/2010 | Hueil et al. |
| 7,673,780 B2 | 3/2010 | Shelton, IV et al. |
| 7,673,781 B2 | 3/2010 | Swayze et al. |
| 7,673,782 B2 | 3/2010 | Hess et al. |
| 7,673,783 B2 | 3/2010 | Morgan et al. |
| 7,678,121 B1 | 3/2010 | Knodel |
| 7,681,772 B2 | 3/2010 | Green et al. |
| 7,682,367 B2 | 3/2010 | Shah et al. |
| 7,682,368 B1 | 3/2010 | Bombard et al. |
| 7,690,547 B2 | 4/2010 | Racenet et al. |
| 7,694,865 B2 | 4/2010 | Scirica |
| 7,699,205 B2 | 4/2010 | Ivanko |
| 7,703,653 B2 | 4/2010 | Shah et al. |
| 7,721,931 B2 | 5/2010 | Shelton, IV et al. |
| 7,721,933 B2 | 5/2010 | Ehrenfels et al. |
| 7,721,935 B2 | 5/2010 | Racenet et al. |
| 7,726,537 B2 | 6/2010 | Olson et al. |
| 7,726,538 B2 | 6/2010 | Holsten et al. |
| 7,726,539 B2 | 6/2010 | Holsten et al. |
| 7,731,072 B2 | 6/2010 | Timm et al. |
| 7,735,703 B2 | 6/2010 | Morgan et al. |
| 7,740,159 B2 | 6/2010 | Shelton, IV et al. |
| 7,740,160 B2 | 6/2010 | Viola |
| 7,743,960 B2 | 6/2010 | Whitman et al. |
| 7,744,628 B2 | 6/2010 | Viola |
| 7,753,245 B2 | 7/2010 | Boudreaux et al. |
| 7,753,248 B2 | 7/2010 | Viola |
| 7,757,924 B2 | 7/2010 | Gerbi et al. |
| 7,757,925 B2 | 7/2010 | Viola et al. |
| 7,762,445 B2 | 7/2010 | Heinrich et al. |
| 7,766,209 B2 | 8/2010 | Baxter, III et al. |
| 7,766,210 B2 | 8/2010 | Shelton, IV et al. |
| 7,766,924 B1 | 8/2010 | Bombard et al. |
| 7,766,928 B2 | 8/2010 | Ezzat et al. |
| 7,770,774 B2 | 8/2010 | Mastri et al. |
| 7,770,775 B2 | 8/2010 | Shelton, IV et al. |
| 7,776,060 B2 | 8/2010 | Mooradian et al. |
| 7,780,055 B2 | 8/2010 | Scirica et al. |
| 7,784,662 B2 | 8/2010 | Wales et al. |
| 7,789,283 B2 | 9/2010 | Shah |
| 7,789,889 B2 | 9/2010 | Zubik et al. |
| 7,793,812 B2 | 9/2010 | Moore et al. |
| 7,793,814 B2 | 9/2010 | Racenet et al. |
| 7,794,475 B2 | 9/2010 | Hess et al. |
| 7,798,385 B2 | 9/2010 | Boyden et al. |
| 7,798,386 B2 | 9/2010 | Schall et al. |
| 7,799,039 B2 | 9/2010 | Shelton, IV et al. |
| 7,810,690 B2 | 10/2010 | Bilotti et al. |
| 7,810,692 B2 | 10/2010 | Hall et al. |
| 7,810,693 B2 | 10/2010 | Broehl et al. |
| 7,815,090 B2 | 10/2010 | Marczyk |
| 7,815,091 B2 | 10/2010 | Marczyk |
| 7,815,092 B2 | 10/2010 | Whitman et al. |
| 7,819,296 B2 | 10/2010 | Hueil et al. |
| 7,819,297 B2 | 10/2010 | Doll et al. |
| 7,819,298 B2 | 10/2010 | Hall et al. |
| 7,819,299 B2 | 10/2010 | Shelton, IV et al. |
| 7,819,796 B2 | 10/2010 | Blake et al. |
| 7,819,896 B2 | 10/2010 | Racenet |
| 7,823,760 B2 | 11/2010 | Zemlok et al. |
| 7,823,761 B2 | 11/2010 | Boyden et al. |
| 7,824,426 B2 | 11/2010 | Racenet et al. |
| 7,828,186 B2 | 11/2010 | Wales |
| 7,828,187 B2 | 11/2010 | Green et al. |
| 7,828,188 B2 | 11/2010 | Jankowski |
| 7,828,189 B2 | 11/2010 | Holsten et al. |
| 7,832,408 B2 | 11/2010 | Shelton, IV et al. |
| 7,832,611 B2 | 11/2010 | Boyden et al. |
| 7,832,612 B2 | 11/2010 | Baxter, III et al. |
| 7,837,079 B2 | 11/2010 | Holsten et al. |
| 7,837,081 B2 | 11/2010 | Holsten et al. |
| 7,841,503 B2 | 11/2010 | Sonnenschein et al. |
| 7,845,533 B2 | 12/2010 | Marczyk et al. |
| 7,845,534 B2 | 12/2010 | Viola et al. |
| 7,845,535 B2 | 12/2010 | Scircia |
| 7,845,537 B2 | 12/2010 | Shelton, IV et al. |
| 7,845,538 B2 | 12/2010 | Whitman |
| 7,850,703 B2 | 12/2010 | Bombard et al. |
| 7,857,183 B2 | 12/2010 | Shelton, IV |
| 7,857,184 B2 | 12/2010 | Viola |
| 7,857,185 B2 | 12/2010 | Swayze et al. |
| 7,857,186 B2 | 12/2010 | Baxter, III et al. |
| 7,861,906 B2 | 1/2011 | Doll et al. |
| 7,861,907 B2 | 1/2011 | Green et al. |
| 7,866,524 B2 | 1/2011 | Krehel |
| 7,866,525 B2 | 1/2011 | Scirica |
| 7,866,526 B2 | 1/2011 | Green et al. |
| 7,866,527 B2 | 1/2011 | Hall et al. |
| 7,866,528 B2 | 1/2011 | Olson et al. |
| 7,870,989 B2 | 1/2011 | Viola et al. |
| 7,886,952 B2 | 2/2011 | Scirica et al. |
| 7,891,532 B2 | 2/2011 | Mastri et al. |
| 7,891,533 B2 | 2/2011 | Green et al. |
| 7,891,534 B2 | 2/2011 | Wenchell et al. |
| 7,896,214 B2 | 3/2011 | Farascioni |
| 7,900,805 B2 | 3/2011 | Shelton, IV et al. |
| 7,901,416 B2 | 3/2011 | Nolan et al. |
| 7,905,380 B2 | 3/2011 | Shelton, IV et al. |
| 7,905,381 B2 | 3/2011 | Baxter, III et al. |
| 7,909,039 B2 | 3/2011 | Hur |
| 7,909,220 B2 | 3/2011 | Viola |
| 7,909,221 B2 | 3/2011 | Viola et al. |
| 7,909,224 B2 | 3/2011 | Prommersberger |
| 7,913,891 B2 | 3/2011 | Doll et al. |
| 7,913,893 B2 | 3/2011 | Mastri et al. |
| 7,914,543 B2 | 3/2011 | Roth et al. |
| 7,918,230 B2 | 4/2011 | Whitman et al. |
| 7,922,061 B2 | 4/2011 | Shelton, IV et al. |
| 7,922,063 B2 | 4/2011 | Zemlok et al. |
| 7,922,064 B2 | 4/2011 | Boyden et al. |
| 7,926,691 B2 | 4/2011 | Viola et al. |
| 7,926,692 B2 | 4/2011 | Racenet et al. |
| 7,934,628 B2 | 5/2011 | Wenchell et al. |
| 7,934,630 B2 | 5/2011 | Shelton, IV et al. |
| 7,934,631 B2 | 5/2011 | Balbierz et al. |
| 7,942,300 B2 | 5/2011 | Rethy et al. |
| 7,942,303 B2 | 5/2011 | Shah |
| 7,950,560 B2 | 5/2011 | Zemlok et al. |
| 7,950,561 B2 | 5/2011 | Aranyi |

(56) References Cited

U.S. PATENT DOCUMENTS

| | | |
|---|---|---|
| 7,950,562 B2 | 5/2011 | Beardsley et al. |
| 7,954,682 B2 | 6/2011 | Giordano et al. |
| 7,954,683 B1 | 6/2011 | Knodel et al. |
| 7,954,684 B2 | 6/2011 | Boudreaux |
| 7,954,685 B2 | 6/2011 | Viola |
| 7,954,686 B2 | 6/2011 | Baxter, III et al. |
| 7,954,687 B2 | 6/2011 | Zemlok et al. |
| 7,959,051 B2 | 6/2011 | Smith et al. |
| 7,963,431 B2 | 6/2011 | Scirica |
| 7,963,432 B2 | 6/2011 | Knodel et al. |
| 7,963,433 B2 | 6/2011 | Whitman et al. |
| 7,967,178 B2 | 6/2011 | Scirica et al. |
| 7,967,179 B2 | 6/2011 | Olson et al. |
| 7,967,180 B2 | 6/2011 | Scirica |
| 7,975,894 B2 | 7/2011 | Boyden et al. |
| 7,980,443 B2 | 7/2011 | Scheib et al. |
| 7,988,026 B2 | 8/2011 | Knodel et al. |
| 7,988,027 B2 | 8/2011 | Olson et al. |
| 7,988,028 B2 | 8/2011 | Farascioni et al. |
| 7,992,758 B2 | 8/2011 | Whitman et al. |
| 7,997,468 B2 | 8/2011 | Farascioni |
| 7,997,469 B2 | 8/2011 | Olson et al. |
| 8,002,795 B2 | 8/2011 | Beetel |
| 8,006,885 B2 | 8/2011 | Marczyk |
| 8,006,887 B2 | 8/2011 | Marczyk |
| 8,007,505 B2 | 8/2011 | Weller et al. |
| 8,007,513 B2 | 8/2011 | Nalagatla et al. |
| 8,011,550 B2 | 9/2011 | Aranyi et al. |
| 8,011,551 B2 | 9/2011 | Marczyk et al. |
| 8,011,552 B2 | 9/2011 | Ivanko |
| 8,011,553 B2 | 9/2011 | Mastri et al. |
| 8,011,555 B2 | 9/2011 | Farinelli et al. |
| 8,012,170 B2 | 9/2011 | Whitman et al. |
| 8,015,976 B2 | 9/2011 | Shah |
| 8,016,177 B2 | 9/2011 | Bettuchi et al. |
| 8,016,178 B2 | 9/2011 | Olson et al. |
| 8,020,742 B2 | 9/2011 | Marczyk |
| 8,020,743 B2 | 9/2011 | Shelton, IV |
| 8,028,882 B2 | 10/2011 | Viola |
| 8,028,883 B2 | 10/2011 | Stopek |
| 8,028,884 B2 | 10/2011 | Sniffin et al. |
| 8,033,438 B2 | 10/2011 | Scirica |
| 8,033,440 B2 | 10/2011 | Wenchell et al. |
| 8,033,441 B2 | 10/2011 | Marczyk |
| 8,033,442 B2 | 10/2011 | Racenet et al. |
| 8,034,077 B2 | 10/2011 | Smith et al. |
| 8,038,044 B2 | 10/2011 | Viola |
| 8,038,045 B2 | 10/2011 | Bettuchi et al. |
| 8,052,024 B2 | 11/2011 | Viola et al. |
| 8,056,787 B2 | 11/2011 | Boudreaux et al. |
| 8,056,788 B2 | 11/2011 | Mastri et al. |
| 8,056,789 B1 | 11/2011 | White et al. |
| 8,056,791 B2 | 11/2011 | Whitman |
| 8,061,577 B2 | 11/2011 | Racenet et al. |
| 8,066,166 B2 | 11/2011 | Demmy et al. |
| 8,070,033 B2 | 12/2011 | Milliman et al. |
| 8,070,034 B1 | 12/2011 | Knodel |
| 8,070,035 B2 | 12/2011 | Holsten et al. |
| 8,074,858 B2 | 12/2011 | Marczyk |
| 8,074,859 B2 | 12/2011 | Kostrzewski |
| 8,074,862 B2 | 12/2011 | Shah |
| 8,083,118 B2 | 12/2011 | Milliman et al. |
| 8,083,119 B2 | 12/2011 | Prommersberger |
| 8,083,120 B2 | 12/2011 | Shelton, IV et al. |
| 8,087,563 B2 | 1/2012 | Milliman et al. |
| 8,091,753 B2 | 1/2012 | Viola |
| 8,091,754 B2 | 1/2012 | Ehrenfels et al. |
| 8,091,756 B2 | 1/2012 | Viola |
| 8,092,493 B2 | 1/2012 | Marczyk |
| 8,096,459 B2 | 1/2012 | Ortiz et al. |
| 8,096,460 B2 | 1/2012 | Blier et al. |
| 8,100,309 B2 | 1/2012 | Marczyk |
| 8,100,310 B2 | 1/2012 | Zemlok |
| 8,102,008 B2 | 1/2012 | Wells |
| 8,113,406 B2 | 2/2012 | Holsten et al. |
| 8,113,407 B2 | 2/2012 | Holsten et al. |
| 8,113,408 B2 | 2/2012 | Wenchell et al. |
| 8,113,409 B2 | 2/2012 | Cohen et al. |
| 8,113,410 B2 | 2/2012 | Hall et al. |
| 8,123,101 B2 | 2/2012 | Racenet et al. |
| 8,127,975 B2 | 3/2012 | Olson et al. |
| 8,127,976 B2 | 3/2012 | Scirica et al. |
| 8,132,703 B2 | 3/2012 | Milliman et al. |
| 8,132,705 B2 | 3/2012 | Viola et al. |
| 8,132,706 B2 | 3/2012 | Marczyk et al. |
| 8,136,713 B2 | 3/2012 | Hathaway et al. |
| 8,141,762 B2 | 3/2012 | Bedi et al. |
| 8,152,041 B2 | 4/2012 | Kostrzewski |
| 8,157,148 B2 | 4/2012 | Scirica |
| 8,157,150 B2 | 4/2012 | Viola et al. |
| 8,157,151 B2 | 4/2012 | Ingmanson et al. |
| 8,157,152 B2 | 4/2012 | Holsten et al. |
| 8,162,197 B2 | 4/2012 | Mastri et al. |
| 8,167,185 B2 | 5/2012 | Shelton, IV et al. |
| 8,167,186 B2 | 5/2012 | Racenet et al. |
| 8,172,121 B2 | 5/2012 | Krehel |
| 8,172,124 B2 | 5/2012 | Shelton, IV et al. |
| 8,181,837 B2 | 5/2012 | Roy |
| 8,186,555 B2 | 5/2012 | Shelton, IV et al. |
| 8,186,557 B2 | 5/2012 | Cohen et al. |
| 8,186,558 B2 | 5/2012 | Sapienza |
| 8,186,559 B1 | 5/2012 | Whitman |
| 8,186,560 B2 | 5/2012 | Hess et al. |
| 8,193,044 B2 | 6/2012 | Kenneth |
| 8,196,795 B2 | 6/2012 | Moore et al. |
| 8,196,796 B2 | 6/2012 | Shelton, IV et al. |
| 8,201,721 B2 | 6/2012 | Zemlok et al. |
| 8,205,619 B2 | 6/2012 | Shah et al. |
| 8,205,780 B2 | 6/2012 | Sorrentino et al. |
| 8,205,781 B2 | 6/2012 | Baxter, III et al. |
| 8,210,412 B2 | 7/2012 | Marczyk |
| 8,210,416 B2 | 7/2012 | Milliman et al. |
| 8,216,236 B2 | 7/2012 | Heinrich et al. |
| 8,220,688 B2 | 7/2012 | Laurent et al. |
| 8,220,690 B2 | 7/2012 | Hess et al. |
| 8,225,979 B2 | 7/2012 | Farascioni et al. |
| 8,225,980 B1 | 7/2012 | Rivera |
| 8,231,040 B2 | 7/2012 | Zemlok et al. |
| 8,231,041 B2 | 7/2012 | Marczyk et al. |
| 8,235,272 B2 | 8/2012 | Nicholas et al. |
| 8,235,273 B2 | 8/2012 | Olson et al. |
| 8,235,274 B2 | 8/2012 | Cappola |
| 8,236,010 B2 | 8/2012 | Ortiz et al. |
| 8,240,536 B2 | 8/2012 | Marczyk |
| 8,240,537 B2 | 8/2012 | Marczyk |
| 8,241,322 B2 | 8/2012 | Whitman et al. |
| 8,245,897 B2 | 8/2012 | Tzakis et al. |
| 8,245,898 B2 | 8/2012 | Smith et al. |
| 8,245,899 B2 | 8/2012 | Swensgard et al. |
| 8,245,931 B2 | 8/2012 | Shigeta |
| 8,252,009 B2 | 8/2012 | Weller et al. |
| 8,256,653 B2 | 9/2012 | Farascioni |
| 8,256,654 B2 | 9/2012 | Bettuchi et al. |
| 8,256,655 B2 | 9/2012 | Sniffin et al. |
| 8,256,656 B2 | 9/2012 | Milliman et al. |
| 8,267,300 B2 | 9/2012 | Boudreaux |
| 8,272,551 B2 | 9/2012 | Knodel et al. |
| 8,272,553 B2 | 9/2012 | Mastri et al. |
| 8,272,554 B2 | 9/2012 | Whitman et al. |
| 8,276,594 B2 | 10/2012 | Shah |
| 8,276,801 B2 | 10/2012 | Zemlok et al. |
| 8,281,973 B2 | 10/2012 | Wenchell et al. |
| 8,286,847 B2 | 10/2012 | Taylor |
| 8,286,848 B2 | 10/2012 | Wenchell et al. |
| 8,286,850 B2 | 10/2012 | Viola |
| 8,292,146 B2 | 10/2012 | Holsten et al. |
| 8,292,147 B2 | 10/2012 | Viola |
| 8,292,148 B2 | 10/2012 | Viola |
| 8,292,149 B2 | 10/2012 | Ivanko |
| 8,292,150 B2 | 10/2012 | Bryant |
| 8,292,151 B2 | 10/2012 | Viola |
| 8,292,152 B2 | 10/2012 | Milliman et al. |
| 8,292,153 B2 | 10/2012 | Jankowski |
| 8,292,154 B2 | 10/2012 | Marczyk |

(56) References Cited

U.S. PATENT DOCUMENTS

| | | | |
|---|---|---|---|
| 8,292,155 B2 | 10/2012 | Shelton, IV et al. |
| 8,292,156 B2 | 10/2012 | Kostrzewski |
| 8,292,158 B2 | 10/2012 | Sapienza |
| 8,308,040 B2 | 11/2012 | Huang et al. |
| 8,308,041 B2 | 11/2012 | Kostrzewski |
| 8,308,042 B2 | 11/2012 | Aranyi |
| 8,308,043 B2 | 11/2012 | Bindra et al. |
| 8,308,044 B2 | 11/2012 | Viola |
| 8,308,046 B2 | 11/2012 | Prommersberger |
| 8,308,757 B2 | 11/2012 | Hillstead et al. |
| 8,317,070 B2 | 11/2012 | Hueil et al. |
| 8,317,071 B1 | 11/2012 | Knodel |
| 8,322,455 B2 | 12/2012 | Shelton, IV et al. |
| 8,322,589 B2 | 12/2012 | Boudreaux |
| 8,328,061 B2 | 12/2012 | Kasvikis |
| 8,328,065 B2 | 12/2012 | Shah |
| 8,333,313 B2 | 12/2012 | Boudreaux et al. |
| 8,336,751 B2 | 12/2012 | Scirica |
| 8,336,753 B2 | 12/2012 | Olson et al. |
| 8,336,754 B2 | 12/2012 | Cappola et al. |
| 8,342,377 B2 | 1/2013 | Milliman et al. |
| 8,342,378 B2 | 1/2013 | Marczyk et al. |
| 8,342,379 B2 | 1/2013 | Whitman et al. |
| 8,342,380 B2 | 1/2013 | Viola |
| 8,348,123 B2 | 1/2013 | Scirica et al. |
| 8,348,124 B2 | 1/2013 | Scirica |
| 8,348,125 B2 | 1/2013 | Viola et al. |
| 8,348,126 B2 | 1/2013 | Olson et al. |
| 8,348,127 B2 | 1/2013 | Marczyk |
| 8,348,129 B2 | 1/2013 | Bedi et al. |
| 8,348,130 B2 | 1/2013 | Shah et al. |
| 8,348,131 B2 | 1/2013 | Omaits et al. |
| 8,353,437 B2 | 1/2013 | Boudreaux |
| 8,353,440 B2 | 1/2013 | Whitman et al. |
| 8,356,740 B1 | 1/2013 | Knodel |
| 8,357,174 B2 | 1/2013 | Roth et al. |
| 8,360,294 B2 | 1/2013 | Scirica |
| 8,360,297 B2 | 1/2013 | Shelton, IV et al. |
| 8,360,298 B2 | 1/2013 | Farascioni et al. |
| 8,360,299 B2 | 1/2013 | Zemlok et al. |
| 8,365,971 B1 | 2/2013 | Knodel |
| 8,365,972 B2 | 2/2013 | Aranyi et al. |
| 8,365,973 B1 | 2/2013 | White et al. |
| 8,365,976 B2 | 2/2013 | Hess et al. |
| 8,371,491 B2 | 2/2013 | Huitema et al. |
| 8,371,492 B2 | 2/2013 | Aranyi et al. |
| 8,371,493 B2 | 2/2013 | Aranyi et al. |
| 8,381,828 B2 | 2/2013 | Whitman et al. |
| 8,381,961 B2 | 2/2013 | Holsten et al. |
| 8,387,848 B2 | 3/2013 | Johnson et al. |
| 8,387,849 B2 | 3/2013 | Buesseler et al. |
| 8,387,850 B2 | 3/2013 | Hathaway et al. |
| 8,388,652 B2 | 3/2013 | Viola |
| 8,393,513 B2 | 3/2013 | Jankowski |
| 8,393,514 B2 | 3/2013 | Shelton, IV et al. |
| 8,393,516 B2 | 3/2013 | Kostrzewski |
| 8,397,971 B2 | 3/2013 | Yates et al. |
| 8,397,972 B2 | 3/2013 | Kostrzewski |
| 8,403,195 B2 | 3/2013 | Beardsley et al. |
| 8,403,196 B2 | 3/2013 | Beardsley et al. |
| 8,403,197 B2 | 3/2013 | Vidal et al. |
| 8,403,198 B2 | 3/2013 | Sorrentino et al. |
| 8,403,956 B1 | 3/2013 | Thompson et al. |
| 8,408,439 B2 | 4/2013 | Huang et al. |
| 8,408,440 B2 | 4/2013 | Olson et al. |
| 8,408,442 B2 | 4/2013 | Racenet et al. |
| 8,413,868 B2 | 4/2013 | Cappola |
| 8,413,869 B2 | 4/2013 | Heinrich |
| 8,413,871 B2 | 4/2013 | Racenet et al. |
| 8,418,904 B2 | 4/2013 | Wenchell et al. |
| 8,418,905 B2 | 4/2013 | Milliman |
| 8,418,906 B2 | 4/2013 | Farascioni et al. |
| 8,418,907 B2 | 4/2013 | Johnson et al. |
| 8,418,908 B1 | 4/2013 | Beardsley |
| 8,419,768 B2 | 4/2013 | Marczyk |
| 8,424,735 B2 | 4/2013 | Viola et al. |
| 8,424,736 B2 | 4/2013 | Scirica et al. |
| 8,424,737 B2 | 4/2013 | Scirica |
| 8,424,739 B2 | 4/2013 | Racenet et al. |
| 8,424,740 B2 | 4/2013 | Shelton, IV et al. |
| 8,439,244 B2 | 5/2013 | Holcomb et al. |
| 8,439,245 B2 | 5/2013 | Knodel et al. |
| 8,439,246 B1 | 5/2013 | Knodel |
| 8,444,036 B2 | 5/2013 | Shelton, IV |
| 8,444,037 B2 | 5/2013 | Nicholas et al. |
| 8,444,038 B2 | 5/2013 | Farascioni et al. |
| 8,448,832 B2 | 5/2013 | Viola et al. |
| 8,453,652 B2 | 6/2013 | Stopek |
| 8,453,905 B2 | 6/2013 | Holcomb et al. |
| 8,453,906 B2 | 6/2013 | Huang et al. |
| 8,453,907 B2 | 6/2013 | Laurent et al. |
| 8,453,908 B2 | 6/2013 | Bedi et al. |
| 8,453,909 B2 | 6/2013 | Olson et al. |
| 8,453,910 B2 | 6/2013 | Bettuchi et al. |
| 8,453,912 B2 | 6/2013 | Mastri et al. |
| 8,453,913 B2 | 6/2013 | Milliman |
| 8,453,914 B2 | 6/2013 | Laurent et al. |
| 8,454,628 B2 | 6/2013 | Smith et al. |
| 8,459,520 B2 | 6/2013 | Giordano et al. |
| 8,459,521 B2 | 6/2013 | Zemlok et al. |
| 8,459,522 B2 | 6/2013 | Marczyk |
| 8,459,523 B2 | 6/2013 | Whitman |
| 8,459,524 B2 | 6/2013 | Pribanic et al. |
| 8,459,525 B2 | 6/2013 | Yates et al. |
| 8,464,922 B2 | 6/2013 | Marczyk |
| 8,464,923 B2 | 6/2013 | Shelton, IV |
| 8,469,252 B2 | 6/2013 | Holcomb et al. |
| 8,469,254 B2 | 6/2013 | Czernik et al. |
| 8,474,677 B2 | 7/2013 | Woodard, Jr. et al. |
| 8,479,967 B2 | 7/2013 | Marczyk |
| 8,479,968 B2 | 7/2013 | Hodgkinson et al. |
| 8,479,969 B2 | 7/2013 | Shelton, IV |
| 8,485,412 B2 * | 7/2013 | Shelton, IV ......... A61B 17/105 227/176.1 |
| 8,490,852 B2 | 7/2013 | Viola |
| 8,496,152 B2 | 7/2013 | Viola |
| 8,496,154 B2 | 7/2013 | Marczyk et al. |
| 8,496,156 B2 | 7/2013 | Sniffin et al. |
| 8,496,683 B2 | 7/2013 | Prommersberger et al. |
| 8,499,993 B2 | 8/2013 | Shelton, IV et al. |
| 8,505,799 B2 | 8/2013 | Viola et al. |
| 8,505,802 B2 | 8/2013 | Viola et al. |
| 8,511,575 B2 | 8/2013 | Cok |
| 8,512,359 B2 | 8/2013 | Whitman et al. |
| 8,512,402 B2 | 8/2013 | Marczyk et al. |
| 8,517,240 B1 | 8/2013 | Mata et al. |
| 8,517,241 B2 | 8/2013 | Nicholas et al. |
| 8,517,243 B2 | 8/2013 | Giordano et al. |
| 8,517,244 B2 | 8/2013 | Shelton, IV et al. |
| 8,523,041 B2 | 9/2013 | Ishitsuki et al. |
| 8,523,042 B2 | 9/2013 | Masiakos et al. |
| 8,523,043 B2 | 9/2013 | Ullrich et al. |
| 8,534,528 B2 | 9/2013 | Shelton, IV |
| 8,540,128 B2 | 9/2013 | Shelton, IV et al. |
| 8,540,129 B2 | 9/2013 | Baxter, III et al. |
| 8,540,130 B2 | 9/2013 | Moore et al. |
| 8,540,131 B2 | 9/2013 | Swayze |
| 8,540,733 B2 | 9/2013 | Whitman et al. |
| 8,544,711 B2 | 10/2013 | Ma et al. |
| 8,550,325 B2 | 10/2013 | Cohen et al. |
| 8,556,151 B2 | 10/2013 | Viola |
| 8,561,870 B2 | 10/2013 | Baxter, III et al. |
| 8,561,873 B2 | 10/2013 | Ingmanson et al. |
| 8,561,874 B2 | 10/2013 | Scirica |
| 8,567,656 B2 | 10/2013 | Shelton, IV et al. |
| 8,573,461 B2 | 11/2013 | Shelton, IV et al. |
| 8,573,463 B2 | 11/2013 | Scirica et al. |
| 8,573,465 B2 | 11/2013 | Shelton, IV |
| 8,579,176 B2 | 11/2013 | Smith et al. |
| 8,579,177 B2 | 11/2013 | Beetel |
| 8,584,919 B2 | 11/2013 | Hueil et al. |
| 8,584,920 B2 | 11/2013 | Hodgkinson |
| 8,590,762 B2 | 11/2013 | Hess et al. |
| 8,596,515 B2 | 12/2013 | Okoniewski |

(56) References Cited

U.S. PATENT DOCUMENTS

| | | |
|---|---|---|
| 8,602,288 B2 | 12/2013 | Shelton, IV et al. |
| 8,608,045 B2 | 12/2013 | Smith et al. |
| 8,608,046 B2 | 12/2013 | Laurent et al. |
| 8,608,047 B2 | 12/2013 | Holsten et al. |
| 8,613,383 B2 | 12/2013 | Beckman et al. |
| 8,613,384 B2 | 12/2013 | Pastorelli et al. |
| 8,616,427 B2 | 12/2013 | Viola |
| 8,616,430 B2 | 12/2013 | (Prommersberger) Stopek |
| 8,627,994 B2 | 1/2014 | Zemlok et al. |
| 8,628,544 B2 | 1/2014 | Farascioni |
| 8,631,988 B2 | 1/2014 | Viola |
| 8,631,989 B2 | 1/2014 | Aranyi et al. |
| 8,631,991 B2 | 1/2014 | Cropper et al. |
| 8,632,525 B2 | 1/2014 | Kerr et al. |
| 8,632,535 B2 | 1/2014 | Shelton, IV et al. |
| 8,636,187 B2 | 1/2014 | Hueil et al. |
| 8,636,190 B2 | 1/2014 | Zemlok et al. |
| 8,636,192 B2 | 1/2014 | Farascioni et al. |
| 8,636,762 B2 | 1/2014 | Whitman et al. |
| 8,636,766 B2 | 1/2014 | Milliman et al. |
| 8,640,940 B2 | 2/2014 | Ohdaira |
| 8,657,174 B2 | 2/2014 | Yates et al. |
| 8,657,176 B2 | 2/2014 | Scirica et al. |
| 8,657,178 B2 | 2/2014 | Hueil et al. |
| 8,662,371 B2 | 3/2014 | Viola |
| 8,668,129 B2 | 3/2014 | Olson |
| 8,672,206 B2 | 3/2014 | Aranyi et al. |
| 8,672,208 B2 | 3/2014 | Hess et al. |
| 8,672,209 B2 | 3/2014 | Crainich |
| 8,678,263 B2 | 3/2014 | Viola |
| 8,678,990 B2 | 3/2014 | Wazer et al. |
| 8,679,155 B2 | 3/2014 | Knodel et al. |
| 8,684,247 B2 | 4/2014 | Scirica et al. |
| 8,684,249 B2 | 4/2014 | Racenet et al. |
| 8,690,039 B2 | 4/2014 | Beardsley et al. |
| 8,695,865 B2 | 4/2014 | Smith et al. |
| 8,695,866 B2 | 4/2014 | Leimbach et al. |
| 8,701,958 B2 | 4/2014 | Shelton, IV et al. |
| 8,701,959 B2 | 4/2014 | Shah |
| 8,701,961 B2 | 4/2014 | Ivanko |
| 8,708,213 B2 | 4/2014 | Shelton, IV et al. |
| 8,714,429 B2 | 5/2014 | Demmy |
| 8,715,277 B2 | 5/2014 | Weizman |
| 8,720,766 B2 | 5/2014 | Hess et al. |
| 8,721,630 B2 | 5/2014 | Ortiz et al. |
| 8,727,197 B2 | 5/2014 | Hess et al. |
| 8,727,200 B2 | 5/2014 | Roy |
| 8,733,612 B2 | 5/2014 | Ma |
| 8,740,034 B2 | 6/2014 | Morgan et al. |
| 8,740,039 B2 | 6/2014 | Farascioni |
| 8,757,465 B2 | 6/2014 | Woodard, Jr. et al. |
| 8,758,391 B2 | 6/2014 | Swayze et al. |
| 8,763,877 B2 | 7/2014 | Schall et al. |
| 8,763,879 B2 | 7/2014 | Shelton, IV et al. |
| 8,770,458 B2 | 7/2014 | Scirica |
| 8,777,082 B2 | 7/2014 | Scirica |
| 8,783,541 B2 | 7/2014 | Shelton, IV et al. |
| 8,783,542 B2 | 7/2014 | Riestenberg et al. |
| 8,789,737 B2 | 7/2014 | Hodgkinson et al. |
| 8,789,738 B2 | 7/2014 | Knodel et al. |
| 8,789,739 B2 | 7/2014 | Swensgard |
| 8,800,838 B2 | 8/2014 | Shelton, IV |
| 8,800,840 B2 | 8/2014 | Jankowski |
| 8,800,841 B2 | 8/2014 | Ellerhorst et al. |
| 8,808,311 B2 | 8/2014 | Heinrich et al. |
| 8,814,024 B2 | 8/2014 | Woodard, Jr. et al. |
| 8,814,025 B2 | 8/2014 | Miller et al. |
| 8,820,603 B2 | 9/2014 | Shelton, IV et al. |
| 8,820,605 B2 | 9/2014 | Shelton, IV |
| 8,820,607 B2 | 9/2014 | Marczyk |
| 8,827,133 B2 | 9/2014 | Shelton, IV et al. |
| 8,827,134 B2 | 9/2014 | Viola et al. |
| 8,833,632 B2 | 9/2014 | Swensgard |
| 8,840,003 B2 | 9/2014 | Morgan et al. |
| 8,840,603 B2 | 9/2014 | Shelton, IV et al. |
| 8,851,355 B2 | 10/2014 | Aranyi et al. |
| 9,016,546 B2 | 4/2015 | Demmy et al. |
| 9,027,817 B2 | 5/2015 | Milliman et al. |
| 10,463,368 B2 | 11/2019 | Kostrzewski |
| 2004/0028502 A1* | 2/2004 | Cummins .......... A61B 17/0644 411/457 |
| 2004/0108357 A1 | 6/2004 | Milliman et al. |
| 2004/0199180 A1 | 10/2004 | Knodel et al. |
| 2004/0199181 A1 | 10/2004 | Knodel et al. |
| 2004/0232201 A1 | 11/2004 | Wenchell et al. |
| 2004/0243151 A1 | 12/2004 | Demmy et al. |
| 2004/0267310 A1 | 12/2004 | Racenet et al. |
| 2005/0006429 A1 | 1/2005 | Wales et al. |
| 2005/0103819 A1 | 5/2005 | Racenet et al. |
| 2005/0216055 A1 | 9/2005 | Scirica et al. |
| 2006/0049229 A1 | 3/2006 | Milliman et al. |
| 2006/0180634 A1 | 8/2006 | Shelton et al. |
| 2006/0289602 A1 | 12/2006 | Wales et al. |
| 2007/0073341 A1 | 3/2007 | Smith et al. |
| 2007/0084897 A1 | 4/2007 | Shelton et al. |
| 2007/0102472 A1 | 5/2007 | Shelton |
| 2007/0106317 A1 | 5/2007 | Shelton et al. |
| 2007/0119901 A1 | 5/2007 | Ehrenfels et al. |
| 2007/0145096 A1 | 6/2007 | Viola et al. |
| 2007/0170225 A1 | 7/2007 | Shelton et al. |
| 2007/0175950 A1 | 8/2007 | Shelton et al. |
| 2007/0175951 A1 | 8/2007 | Shelton et al. |
| 2007/0175955 A1 | 8/2007 | Shelton et al. |
| 2007/0179528 A1 | 8/2007 | Soltz et al. |
| 2007/0194079 A1 | 8/2007 | Hueil et al. |
| 2007/0194082 A1 | 8/2007 | Morgan et al. |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0045982 A1* | 2/2008 | To .................. A61B 17/0682 606/151 |
| 2008/0078802 A1 | 4/2008 | Hess et al. |
| 2008/0110961 A1 | 5/2008 | Voegele et al. |
| 2008/0169328 A1 | 7/2008 | Shelton |
| 2008/0169332 A1 | 7/2008 | Shelton et al. |
| 2008/0169333 A1 | 7/2008 | Shelton et al. |
| 2008/0287987 A1 | 11/2008 | Boyden et al. |
| 2008/0296346 A1 | 12/2008 | Shelton, IV et al. |
| 2008/0308602 A1 | 12/2008 | Timm et al. |
| 2008/0308603 A1 | 12/2008 | Shelton et al. |
| 2009/0001121 A1 | 1/2009 | Hess et al. |
| 2009/0001130 A1 | 1/2009 | Hess et al. |
| 2009/0090763 A1 | 4/2009 | Zemlok et al. |
| 2009/0090766 A1 | 4/2009 | Knodel |
| 2009/0242610 A1 | 10/2009 | Shelton, IV et al. |
| 2009/0255974 A1 | 10/2009 | Viola |
| 2009/0272787 A1 | 11/2009 | Scirica |
| 2009/0277948 A1 | 11/2009 | Beardsley et al. |
| 2009/0277949 A1 | 11/2009 | Viola et al. |
| 2009/0283568 A1 | 11/2009 | Racenet et al. |
| 2009/0308907 A1 | 12/2009 | Nalagatla et al. |
| 2010/0012703 A1 | 1/2010 | Calabrese et al. |
| 2010/0069934 A1 | 3/2010 | Bombard et al. |
| 2010/0069942 A1 | 3/2010 | Shelton, IV |
| 2010/0127041 A1 | 5/2010 | Morgan et al. |
| 2010/0133317 A1 | 6/2010 | Shelton, IV et al. |
| 2010/0147921 A1 | 6/2010 | Olson |
| 2010/0147922 A1 | 6/2010 | Olson |
| 2010/0155453 A1 | 6/2010 | Bombard et al. |
| 2010/0193566 A1 | 8/2010 | Scheib et al. |
| 2010/0224668 A1 | 9/2010 | Fontayne et al. |
| 2010/0249802 A1 | 9/2010 | May et al. |
| 2010/0252611 A1 | 10/2010 | Ezzat et al. |
| 2010/0305552 A1 | 12/2010 | Shelton, IV et al. |
| 2011/0006099 A1 | 1/2011 | Hall et al. |
| 2011/0006101 A1 | 1/2011 | Hall et al. |
| 2011/0017801 A1 | 1/2011 | Zemlok et al. |
| 2011/0024477 A1 | 2/2011 | Hall |
| 2011/0024478 A1 | 2/2011 | Shelton, IV |
| 2011/0036891 A1 | 2/2011 | Zemlok et al. |
| 2011/0068148 A1 | 3/2011 | Hall et al. |
| 2011/0087276 A1 | 4/2011 | Bedi et al. |
| 2011/0101069 A1 | 5/2011 | Bombard et al. |

(56) References Cited

U.S. PATENT DOCUMENTS

| | | |
|---|---|---|
| 2011/0108603 A1 | 5/2011 | Racenet et al. |
| 2011/0114702 A1 | 5/2011 | Farascioni |
| 2011/0121049 A1 | 5/2011 | Malinouskas et al. |
| 2011/0132961 A1 | 6/2011 | Whitman et al. |
| 2011/0132964 A1 | 6/2011 | Weisenburgh, II et al. |
| 2011/0139851 A1 | 6/2011 | McCuen |
| 2011/0147433 A1 | 6/2011 | Shelton, IV et al. |
| 2011/0155781 A1 | 6/2011 | Swensgard et al. |
| 2011/0155787 A1 | 6/2011 | Baxter, III et al. |
| 2011/0163146 A1 | 7/2011 | Ortiz et al. |
| 2011/0163149 A1 | 7/2011 | Viola |
| 2011/0192881 A1 | 8/2011 | Balbierz et al. |
| 2011/0192882 A1 | 8/2011 | Hess et al. |
| 2011/0192883 A1 | 8/2011 | Whitman et al. |
| 2011/0204119 A1 | 8/2011 | McCuen |
| 2011/0278343 A1 | 11/2011 | Knodel et al. |
| 2011/0288573 A1 | 11/2011 | Yates et al. |
| 2011/0290851 A1 | 12/2011 | Shelton, IV |
| 2011/0290853 A1 | 12/2011 | Shelton, IV et al. |
| 2011/0290854 A1 | 12/2011 | Timm et al. |
| 2011/0290855 A1 | 12/2011 | Moore et al. |
| 2011/0290856 A1 | 12/2011 | Shelton, IV et al. |
| 2012/0016362 A1 | 1/2012 | Heinrich et al. |
| 2012/0037683 A1 | 2/2012 | Lee |
| 2012/0053406 A1 | 3/2012 | Conlon et al. |
| 2012/0061446 A1 | 3/2012 | Knodel et al. |
| 2012/0061450 A1 | 3/2012 | Kostrzewski |
| 2012/0074196 A1 | 3/2012 | Shelton, IV et al. |
| 2012/0074200 A1 | 3/2012 | Schmid et al. |
| 2012/0080474 A1 | 4/2012 | Farascioni |
| 2012/0080475 A1 | 4/2012 | Smith et al. |
| 2012/0080478 A1 | 4/2012 | Morgan et al. |
| 2012/0080479 A1 | 4/2012 | Shelton, IV |
| 2012/0080481 A1 | 4/2012 | Widenhouse et al. |
| 2012/0080482 A1 | 4/2012 | Schall et al. |
| 2012/0080484 A1 | 4/2012 | Morgan et al. |
| 2012/0080485 A1 | 4/2012 | Woodard, Jr. et al. |
| 2012/0080486 A1 | 4/2012 | Woodard, Jr. et al. |
| 2012/0080488 A1 | 4/2012 | Shelton, IV et al. |
| 2012/0080489 A1 | 4/2012 | Shelton, IV et al. |
| 2012/0080490 A1 | 4/2012 | Shelton, IV et al. |
| 2012/0080491 A1 | 4/2012 | Shelton, IV et al. |
| 2012/0080493 A1 | 4/2012 | Shelton, IV et al. |
| 2012/0080494 A1 | 4/2012 | Thompson et al. |
| 2012/0080495 A1 | 4/2012 | Holcomb et al. |
| 2012/0080498 A1 | 4/2012 | Shelton, IV et al. |
| 2012/0080499 A1 | 4/2012 | Schall et al. |
| 2012/0080502 A1 | 4/2012 | Morgan et al. |
| 2012/0091183 A1 | 4/2012 | Manoux et al. |
| 2012/0100200 A1 | 4/2012 | Belcheva et al. |
| 2012/0138659 A1 | 6/2012 | Marczyk et al. |
| 2012/0175399 A1 | 7/2012 | Shelton et al. |
| 2012/0181322 A1 | 7/2012 | Whitman et al. |
| 2012/0187179 A1 | 7/2012 | Gleiman |
| 2012/0193394 A1 | 8/2012 | Holcomb et al. |
| 2012/0193399 A1 | 8/2012 | Holcomb et al. |
| 2012/0199632 A1 | 8/2012 | Spivey et al. |
| 2012/0211542 A1 | 8/2012 | Racenet |
| 2012/0223121 A1 | 9/2012 | Viola et al. |
| 2012/0223123 A1 | 9/2012 | Baxter, III et al. |
| 2012/0228358 A1 | 9/2012 | Zemlok et al. |
| 2012/0234893 A1 | 9/2012 | Schuckmann et al. |
| 2012/0234895 A1 | 9/2012 | O'Connor et al. |
| 2012/0234897 A1 | 9/2012 | Shelton, IV et al. |
| 2012/0234899 A1 | 9/2012 | Scheib et al. |
| 2012/0239009 A1 | 9/2012 | Mollere et al. |
| 2012/0241491 A1 | 9/2012 | Aldridge et al. |
| 2012/0241492 A1 | 9/2012 | Shelton, IV et al. |
| 2012/0241493 A1 | 9/2012 | Baxter, III et al. |
| 2012/0241496 A1 | 9/2012 | Mandakolathur Vasudevan et al. |
| 2012/0241497 A1 | 9/2012 | Mandakolathur Vasudevan et al. |
| 2012/0241498 A1 | 9/2012 | Gonzalez et al. |
| 2012/0241499 A1 | 9/2012 | Baxter, III et al. |
| 2012/0241500 A1 | 9/2012 | Timmer et al. |
| 2012/0241501 A1 | 9/2012 | Swayze et al. |
| 2012/0241502 A1 | 9/2012 | Aldridge et al. |
| 2012/0241503 A1 | 9/2012 | Baxter, III et al. |
| 2012/0241504 A1 | 9/2012 | Soltz et al. |
| 2012/0241505 A1 | 9/2012 | Alexander, III et al. |
| 2012/0248169 A1 | 10/2012 | Widenhouse et al. |
| 2012/0248170 A1 | 10/2012 | Marczyk |
| 2012/0255986 A1 | 10/2012 | Petty et al. |
| 2012/0286021 A1 | 11/2012 | Kostrzewski |
| 2012/0286022 A1 | 11/2012 | Olson et al. |
| 2012/0292369 A1 | 11/2012 | Munro, III et al. |
| 2012/0298719 A1 | 11/2012 | Shelton, IV et al. |
| 2012/0298722 A1 | 11/2012 | Hess et al. |
| 2012/0312858 A1 | 12/2012 | Patankar et al. |
| 2012/0312859 A1 | 12/2012 | Gupta et al. |
| 2012/0312860 A1 | 12/2012 | Ming et al. |
| 2012/0312861 A1 | 12/2012 | Gurumurthy et al. |
| 2012/0318842 A1 | 12/2012 | Anim et al. |
| 2012/0318843 A1 | 12/2012 | Henderson et al. |
| 2012/0318844 A1 | 12/2012 | Shelton, IV et al. |
| 2013/0008937 A1 | 1/2013 | Viola |
| 2013/0012983 A1 | 1/2013 | Kleyman |
| 2013/0015231 A1 | 1/2013 | Kostrzewski |
| 2013/0020375 A1 | 1/2013 | Shelton, IV et al. |
| 2013/0020376 A1 | 1/2013 | Shelton, IV et al. |
| 2013/0026208 A1 | 1/2013 | Shelton, IV et al. |
| 2013/0026210 A1 | 1/2013 | Shelton, IV et al. |
| 2013/0030438 A1 | 1/2013 | Fox |
| 2013/0032626 A1 | 2/2013 | Smith et al. |
| 2013/0037594 A1 | 2/2013 | Dhakad et al. |
| 2013/0037595 A1 | 2/2013 | Gupta et al. |
| 2013/0037596 A1 | 2/2013 | Bear et al. |
| 2013/0037597 A1 | 2/2013 | Katre et al. |
| 2013/0037598 A1 | 2/2013 | Marczyk |
| 2013/0041406 A1 | 2/2013 | Bear et al. |
| 2013/0048697 A1 | 2/2013 | Shelton, IV et al. |
| 2013/0056518 A1 | 3/2013 | Swensgard |
| 2013/0056521 A1 | 3/2013 | Swensgard |
| 2013/0062391 A1 | 3/2013 | Boudreaux et al. |
| 2013/0062393 A1 | 3/2013 | Bruewer et al. |
| 2013/0062394 A1 | 3/2013 | Smith et al. |
| 2013/0068815 A1 | 3/2013 | Bruewer et al. |
| 2013/0068816 A1 | 3/2013 | Mandakolathur Vasudevan et al. |
| 2013/0068818 A1 | 3/2013 | Kasvikis |
| 2013/0068821 A1 | 3/2013 | Huitema et al. |
| 2013/0075443 A1 | 3/2013 | Giordano et al. |
| 2013/0075444 A1 | 3/2013 | Cappola et al. |
| 2013/0075445 A1 | 3/2013 | Balek et al. |
| 2013/0075446 A1 | 3/2013 | Wang et al. |
| 2013/0075447 A1 | 3/2013 | Weisenburgh, II et al. |
| 2013/0075448 A1 | 3/2013 | Schmid et al. |
| 2013/0075449 A1 | 3/2013 | Schmid et al. |
| 2013/0075450 A1 | 3/2013 | Schmid et al. |
| 2013/0075451 A1 | 3/2013 | Balek et al. |
| 2013/0082086 A1 | 4/2013 | Hueil et al. |
| 2013/0087597 A1 | 4/2013 | Shelton, IV et al. |
| 2013/0087599 A1 | 4/2013 | Krumanaker et al. |
| 2013/0087600 A1 | 4/2013 | Scirica |
| 2013/0087601 A1 | 4/2013 | Farascioni |
| 2013/0087602 A1 | 4/2013 | Olson et al. |
| 2013/0087603 A1 | 4/2013 | Viola |
| 2013/0092717 A1 | 4/2013 | Marczyk et al. |
| 2013/0098964 A1 | 4/2013 | Smith et al. |
| 2013/0098965 A1 | 4/2013 | Kostrzewski et al. |
| 2013/0098966 A1 | 4/2013 | Kostrzewski et al. |
| 2013/0098970 A1 | 4/2013 | Racenet et al. |
| 2013/0105545 A1 | 5/2013 | Burbank |
| 2013/0105548 A1 | 5/2013 | Hodgkinson et al. |
| 2013/0105552 A1 | 5/2013 | Weir et al. |
| 2013/0105553 A1 | 5/2013 | (Tarinelli) Racenet et al. |
| 2013/0112730 A1 | 5/2013 | Whitman et al. |
| 2013/0112732 A1 | 5/2013 | Aranyi et al. |
| 2013/0112733 A1 | 5/2013 | Aranyi et al. |
| 2013/0119109 A1 | 5/2013 | Farascioni et al. |
| 2013/0126581 A1 | 5/2013 | Yates et al. |
| 2013/0126582 A1 | 5/2013 | Shelton, IV et al. |
| 2013/0126586 A1 | 5/2013 | Zhang et al. |
| 2013/0140343 A1 | 6/2013 | Knodel |
| 2013/0144333 A1 | 6/2013 | Viola |
| 2013/0146641 A1 | 6/2013 | Shelton, IV et al. |

(56) References Cited

U.S. PATENT DOCUMENTS

| | | |
|---|---|---|
| 2013/0146642 A1 | 6/2013 | Shelton, IV et al. |
| 2013/0146643 A1 | 6/2013 | Schmid et al. |
| 2013/0153636 A1 | 6/2013 | Shelton, IV et al. |
| 2013/0153641 A1 | 6/2013 | Shelton, IV et al. |
| 2013/0161374 A1 | 6/2013 | Swayze et al. |
| 2013/0168431 A1 | 7/2013 | Zemlok et al. |
| 2013/0175316 A1 | 7/2013 | Thompson et al. |
| 2013/0193188 A1 | 8/2013 | Shelton, IV et al. |
| 2013/0277410 A1 | 10/2013 | Fernandez et al. |
| 2013/0334280 A1 | 12/2013 | Krehel et al. |
| 2013/0334281 A1 | 12/2013 | Williams |
| 2014/0001232 A1 | 1/2014 | Cappola et al. |
| 2014/0001233 A1 | 1/2014 | Cappola et al. |
| 2014/0014704 A1 | 1/2014 | Onukuri et al. |
| 2014/0014707 A1 | 1/2014 | Onukuri et al. |
| 2014/0021242 A1 | 1/2014 | Hodgkinson et al. |
| 2014/0025046 A1 | 1/2014 | Williams et al. |
| 2014/0027492 A1 | 1/2014 | Williams |
| 2014/0042205 A1* | 2/2014 | Baxter, III .......... A61B 17/064 227/175.1 |
| 2014/0048580 A1 | 2/2014 | Merchant et al. |
| 2014/0061280 A1 | 3/2014 | Ingmanson et al. |
| 2014/0076955 A1 | 3/2014 | Lorenz |
| 2014/0103092 A1 | 4/2014 | Kostrzewski et al. |
| 2014/0110453 A1 | 4/2014 | Wingardner et al. |
| 2014/0110455 A1 | 4/2014 | Ingmanson et al. |
| 2014/0110457 A1* | 4/2014 | Zhang .................. A61B 17/068 227/177.1 |
| 2014/0131418 A1 | 5/2014 | Kostrzewski |
| 2014/0131419 A1 | 5/2014 | Bettuchi |
| 2014/0138423 A1 | 5/2014 | Whitfield et al. |
| 2014/0151431 A1 | 6/2014 | Hodgkinson et al. |
| 2014/0166720 A1 | 6/2014 | Chowaniec et al. |
| 2014/0166721 A1 | 6/2014 | Stevenson et al. |
| 2014/0166724 A1 | 6/2014 | Schellin et al. |
| 2014/0166725 A1 | 6/2014 | Schellin et al. |
| 2014/0166726 A1 | 6/2014 | Schellin et al. |
| 2014/0175146 A1 | 6/2014 | Knodel |
| 2014/0175150 A1 | 6/2014 | Shelton, IV et al. |
| 2014/0203061 A1 | 7/2014 | Hodgkinson |
| 2014/0203062 A1 | 7/2014 | Viola |
| 2014/0203063 A1 | 7/2014 | Hessler et al. |
| 2014/0239036 A1 | 8/2014 | Zerkle et al. |
| 2014/0239037 A1 | 8/2014 | Boudreaux et al. |
| 2014/0239038 A1 | 8/2014 | Leimbach et al. |
| 2014/0239040 A1 | 8/2014 | Fanelli et al. |
| 2014/0239041 A1 | 8/2014 | Zerkle et al. |
| 2014/0239042 A1 | 8/2014 | Simms et al. |
| 2014/0239043 A1 | 8/2014 | Simms et al. |
| 2014/0239044 A1 | 8/2014 | Hoffman |
| 2014/0239047 A1 | 8/2014 | Hodgkinson et al. |
| 2014/0246471 A1 | 9/2014 | Jaworek et al. |
| 2014/0246472 A1 | 9/2014 | Kimsey et al. |
| 2014/0246473 A1 | 9/2014 | Auld |
| 2014/0246474 A1 | 9/2014 | Hall et al. |
| 2014/0246475 A1 | 9/2014 | Hall et al. |
| 2014/0246476 A1 | 9/2014 | Hall et al. |
| 2014/0246477 A1 | 9/2014 | Koch, Jr. et al. |
| 2014/0246478 A1 | 9/2014 | Baber et al. |
| 2014/0246479 A1 | 9/2014 | Baber et al. |
| 2014/0252062 A1 | 9/2014 | Mozdzierz |
| 2014/0252064 A1 | 9/2014 | Mozdzierz et al. |
| 2014/0252065 A1 | 9/2014 | Hessler et al. |
| 2014/0263537 A1 | 9/2014 | Leimbach et al. |
| 2014/0263539 A1 | 9/2014 | Leimbach et al. |
| 2014/0263540 A1 | 9/2014 | Covach et al. |
| 2014/0263541 A1 | 9/2014 | Leimbach et al. |
| 2014/0263542 A1 | 9/2014 | Leimbach et al. |
| 2014/0263543 A1 | 9/2014 | Leimbach et al. |
| 2014/0263544 A1 | 9/2014 | Ranucci et al. |
| 2014/0263546 A1 | 9/2014 | Aranyi |
| 2014/0263550 A1 | 9/2014 | Aranyi et al. |
| 2014/0263551 A1 | 9/2014 | Hall et al. |
| 2014/0263552 A1 | 9/2014 | Hall et al. |
| 2014/0263553 A1 | 9/2014 | Leimbach et al. |
| 2014/0263554 A1 | 9/2014 | Leimbach et al. |
| 2014/0263555 A1 | 9/2014 | Hufnagel et al. |
| 2014/0263557 A1* | 9/2014 | Schaller .......... A61B 17/07207 227/176.1 |
| 2014/0263558 A1 | 9/2014 | Hausen et al. |
| 2014/0263562 A1 | 9/2014 | Patel et al. |
| 2014/0263564 A1 | 9/2014 | Leimbach et al. |
| 2014/0263565 A1 | 9/2014 | Lytle, IV et al. |
| 2014/0263566 A1 | 9/2014 | Williams et al. |
| 2014/0263570 A1 | 9/2014 | Hopkins et al. |
| 2014/0284371 A1 | 9/2014 | Morgan et al. |
| 2014/0284372 A1 | 9/2014 | Kostrzewski |
| 2014/0291379 A1 | 10/2014 | Schellin et al. |
| 2014/0291380 A1 | 10/2014 | Weaner et al. |
| 2014/0291383 A1 | 10/2014 | Spivey et al. |
| 2014/0303668 A1 | 10/2014 | Nicholas et al. |
| 2014/0309665 A1 | 10/2014 | Parihar et al. |
| 2014/0332578 A1 | 11/2014 | Fernandez et al. |
| 2014/0339286 A1 | 11/2014 | Motooka et al. |
| 2014/0353358 A1 | 12/2014 | Shelton, IV et al. |
| 2014/0367445 A1 | 12/2014 | Ingmanson et al. |
| 2014/0367446 A1 | 12/2014 | Ingmanson et al. |
| 2014/0367448 A1 | 12/2014 | Cappola |
| 2015/0048143 A1 | 2/2015 | Scheib et al. |
| 2015/0053740 A1 | 2/2015 | Shelton, IV |
| 2015/0053742 A1 | 2/2015 | Shelton, IV et al. |
| 2015/0053744 A1 | 2/2015 | Swayze et al. |
| 2015/0053749 A1 | 2/2015 | Shelton, IV et al. |
| 2015/0054753 A1 | 2/2015 | Morgan et al. |
| 2015/0060517 A1 | 3/2015 | Williams |
| 2015/0076205 A1 | 3/2015 | Zergiebel |
| 2015/0076211 A1 | 3/2015 | Irka et al. |
| 2015/0080912 A1 | 3/2015 | Sapre |
| 2015/0083780 A1* | 3/2015 | Shelton, IV ..... A61B 17/00234 227/176.1 |
| 2015/0133996 A1 | 5/2015 | Shelton, IV et al. |
| 2015/0134076 A1 | 5/2015 | Shelton, IV et al. |
| 2015/0157321 A1 | 6/2015 | Zergiebel et al. |
| 2015/0173744 A1 | 6/2015 | Shelton, IV et al. |
| 2015/0173745 A1 | 6/2015 | Baxter, III et al. |
| 2015/0173746 A1 | 6/2015 | Baxter, III et al. |
| 2015/0173747 A1 | 6/2015 | Baxter, III et al. |
| 2015/0173748 A1* | 6/2015 | Marczyk ............ A61B 17/0644 227/177.1 |
| 2015/0173749 A1 | 6/2015 | Shelton, IV et al. |
| 2015/0173750 A1 | 6/2015 | Shelton, IV et al. |
| 2015/0173755 A1 | 6/2015 | Baxter, III et al. |
| 2015/0173756 A1 | 6/2015 | Baxter, III et al. |
| 2015/0173760 A1 | 6/2015 | Shelton, IV et al. |
| 2015/0173761 A1 | 6/2015 | Shelton, IV et al. |
| 2015/0173762 A1 | 6/2015 | Shelton, IV et al. |
| 2016/0000429 A1* | 1/2016 | Knodel ................ A61B 17/068 606/219 |
| 2016/0051259 A1* | 2/2016 | Hopkins .......... A61B 17/07207 227/176.1 |
| 2017/0119388 A1* | 5/2017 | Kostrzewski ...... A61B 17/0644 |

FOREIGN PATENT DOCUMENTS

| | | |
|---|---|---|
| DE | 2744824 A1 | 4/1978 |
| DE | 2903159 A1 | 7/1980 |
| DE | 3114135 A1 | 10/1982 |
| DE | 4213426 A1 | 10/1992 |
| DE | 4300307 A1 | 7/1994 |
| EP | 0041022 A1 | 12/1981 |
| EP | 0136950 A2 | 4/1985 |
| EP | 0140552 A2 | 5/1985 |
| EP | 0156774 A2 | 10/1985 |
| EP | 0213817 A1 | 3/1987 |
| EP | 0216532 A1 | 4/1987 |
| EP | 0220029 A1 | 4/1987 |
| EP | 0273468 A2 | 7/1988 |
| EP | 0324166 A2 | 7/1989 |
| EP | 0324635 A1 | 7/1989 |
| EP | 0324637 A1 | 7/1989 |
| EP | 0324638 A1 | 7/1989 |
| EP | 0365153 A1 | 4/1990 |
| EP | 0369324 A1 | 5/1990 |

(56) References Cited

FOREIGN PATENT DOCUMENTS

| | | | |
|---|---|---|---|
| EP | 0373762 | A1 | 6/1990 |
| EP | 0380025 | A2 | 8/1990 |
| EP | 0399701 | A1 | 11/1990 |
| EP | 0449394 | A2 | 10/1991 |
| EP | 0484677 | A1 | 5/1992 |
| EP | 0489436 | A1 | 6/1992 |
| EP | 0503662 | A1 | 9/1992 |
| EP | 0514139 | A2 | 11/1992 |
| EP | 0536903 | A2 | 4/1993 |
| EP | 0537572 | A2 | 4/1993 |
| EP | 0539762 | A1 | 5/1993 |
| EP | 0545029 | A1 | 6/1993 |
| EP | 0552050 | A2 | 7/1993 |
| EP | 0552423 | A2 | 7/1993 |
| EP | 0579038 | A1 | 1/1994 |
| EP | 0589306 | A2 | 3/1994 |
| EP | 0591946 | A1 | 4/1994 |
| EP | 0592243 | A2 | 4/1994 |
| EP | 0593920 | A1 | 4/1994 |
| EP | 0598202 | A1 | 5/1994 |
| EP | 0598579 | A1 | 5/1994 |
| EP | 0600182 | A2 | 6/1994 |
| EP | 0621006 | A1 | 10/1994 |
| EP | 0621009 | A1 | 10/1994 |
| EP | 0641546 | A1 | 3/1995 |
| EP | 0656188 | A2 | 6/1995 |
| EP | 0666057 | A2 | 8/1995 |
| EP | 0705571 | A1 | 4/1996 |
| EP | 0760230 | A1 | 3/1997 |
| EP | 1952769 | A2 | 8/2008 |
| EP | 2090253 | A2 | 8/2009 |
| EP | 2090254 | A1 | 8/2009 |
| EP | 2583630 | A2 | 4/2013 |
| EP | 2586382 | A2 | 5/2013 |
| EP | 2907456 | A1 | 8/2015 |
| FR | 391239 | A | 10/1908 |
| FR | 2542188 | A1 | 9/1984 |
| FR | 2660851 | A1 | 10/1991 |
| FR | 2681775 | A1 | 4/1993 |
| GB | 1352554 | A | 5/1974 |
| GB | 1452185 | A | 10/1976 |
| GB | 1555455 | A | 11/1979 |
| GB | 2048685 | A | 12/1980 |
| GB | 2070499 | A | 9/1981 |
| GB | 2141066 | A | 12/1984 |
| GB | 2165559 | A | 4/1986 |
| JP | 51149985 | | 12/1976 |
| JP | H07163576 | A | 6/1995 |
| JP | 2001087272 | | 4/2001 |
| JP | 2004524078 | A | 8/2004 |
| JP | 2006334413 | A | 12/2006 |
| JP | 2015150419 | A | 8/2015 |
| SU | 659146 | A1 | 4/1979 |
| SU | 728848 | A1 | 4/1980 |
| SU | 980703 | A1 | 12/1982 |
| SU | 990220 | A1 | 1/1983 |
| WO | 2008302247 | | 7/1983 |
| WO | 8910094 | A1 | 11/1989 |
| WO | 9210976 | A1 | 7/1992 |
| WO | 9308754 | A1 | 5/1993 |
| WO | 9314706 | A1 | 8/1993 |
| WO | 2004/032760 | A2 | 4/2004 |
| WO | 2009071070 | A2 | 6/2009 |
| WO | 2014152942 | A1 | 9/2014 |
| WO | 20150191887 | A1 | 12/2015 |

OTHER PUBLICATIONS

European Search Report dated Aug. 16, 2016, issued in EP Application No. 16 16 4369.
European Examination Report dated Sep. 19, 2017, issued in EP Application No. 16 164 369.
Chinese Office Action dated Nov. 1, 2019, issued in CN Appln. No. 201610221803.
Australian Office Action dated Oct. 23, 2019, issued in AU Appln. No. 2016201623.
Chinese Office Action dated Jul. 2, 2020, issued in CN Appln. No. 201610221803.
Canadian Office Action dated May 10, 2022, issued in corresponding CA Appln. No. 2,923,239, 7 pages.

* cited by examiner

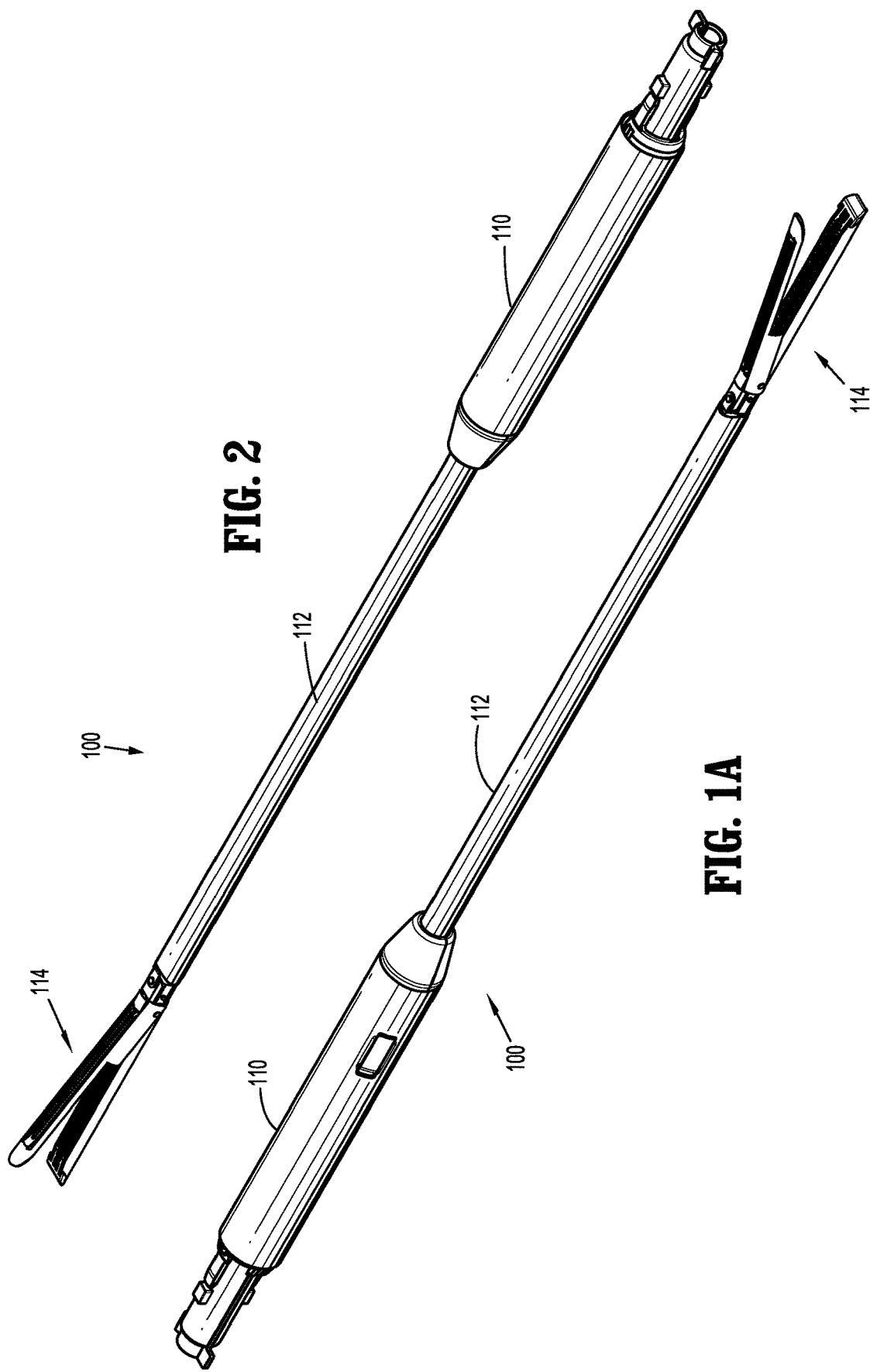

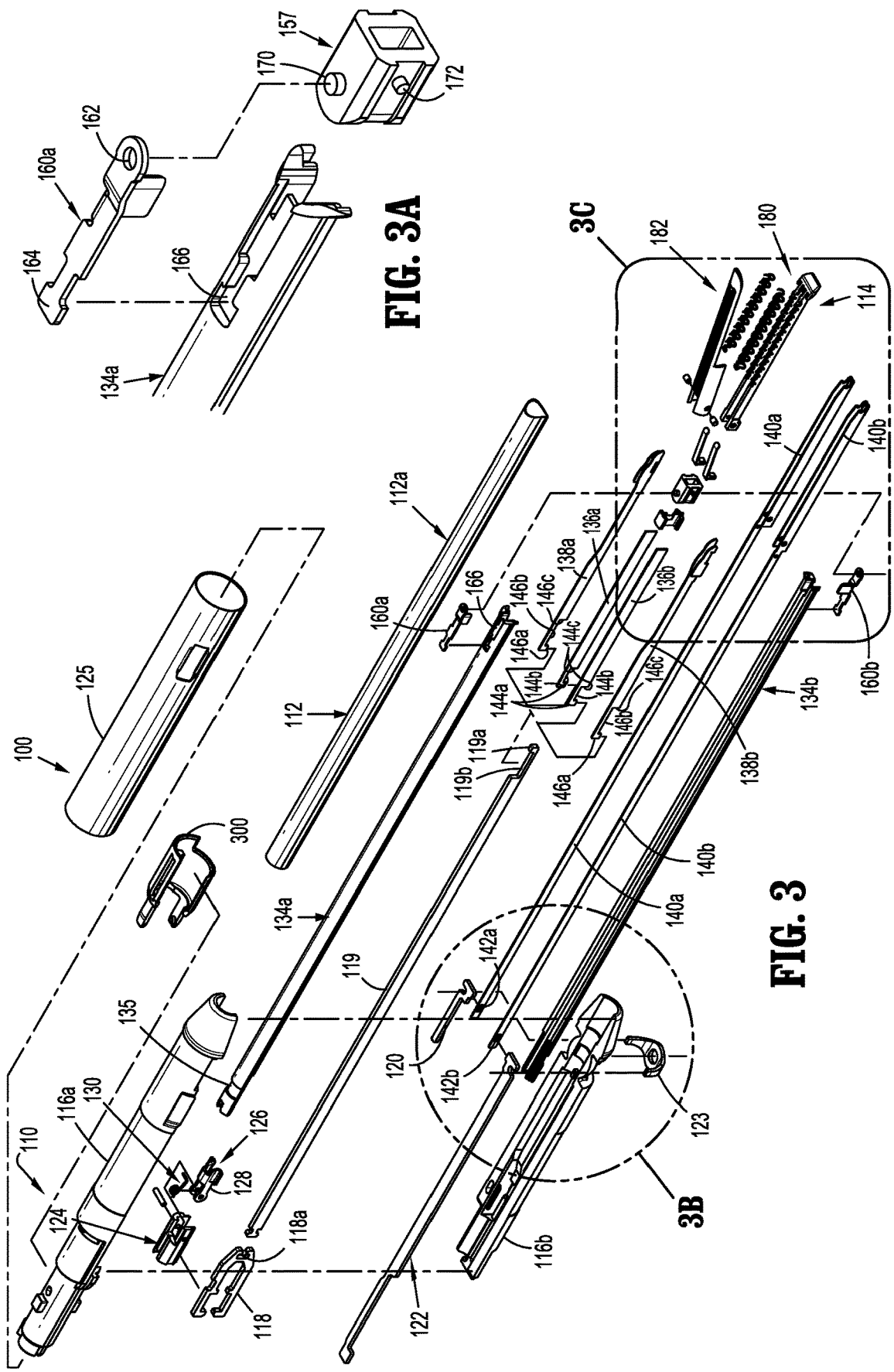

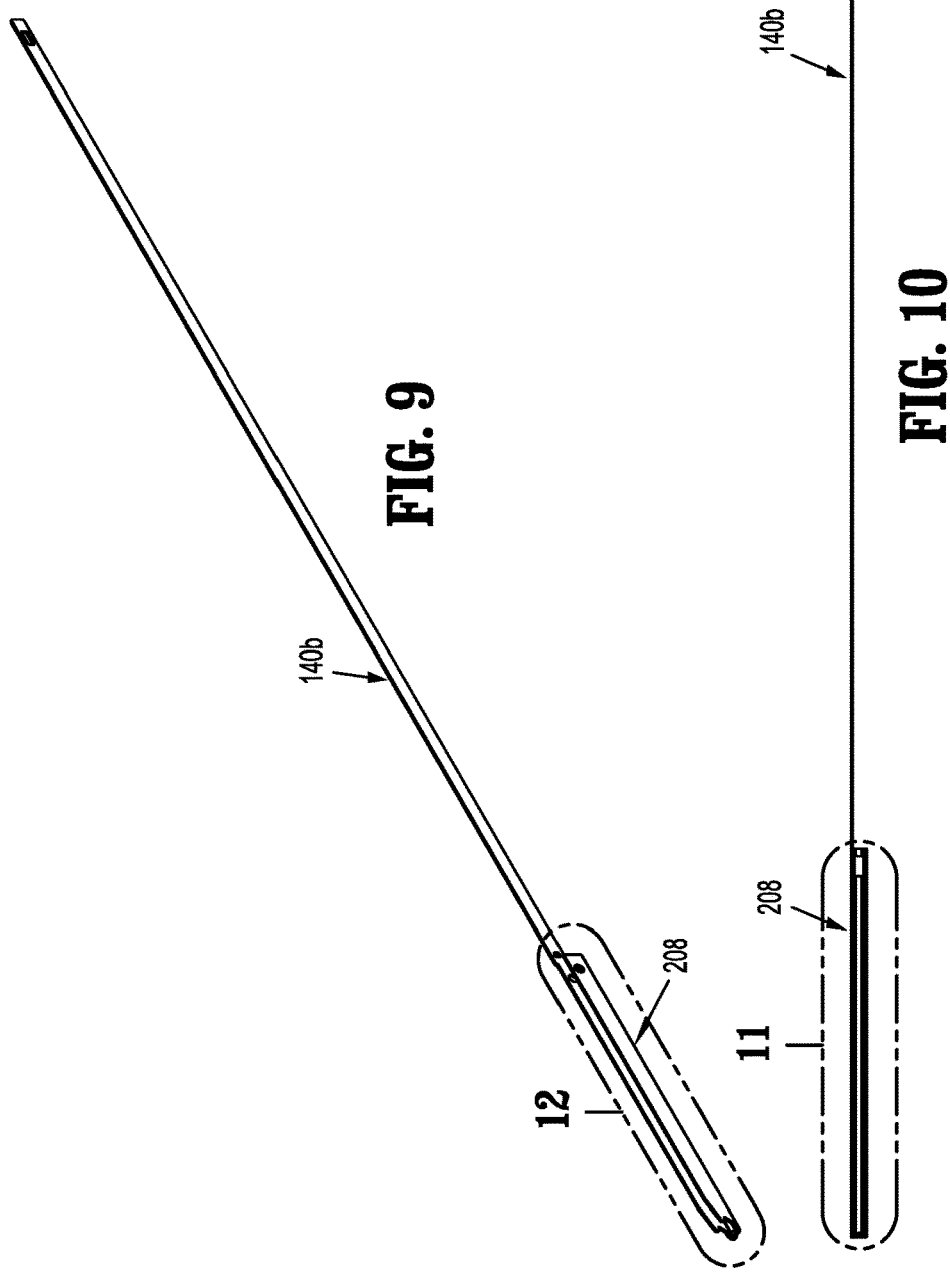

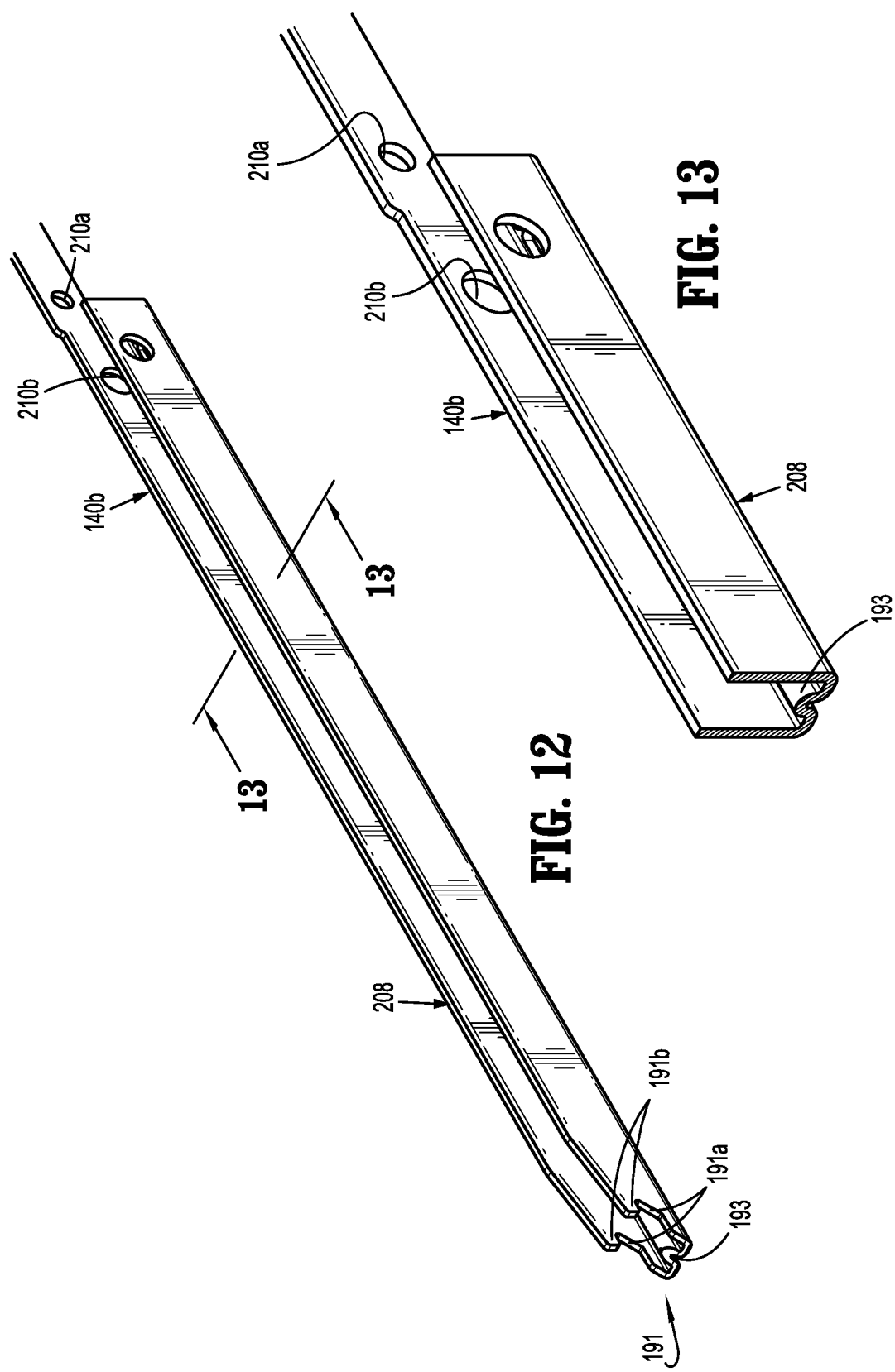

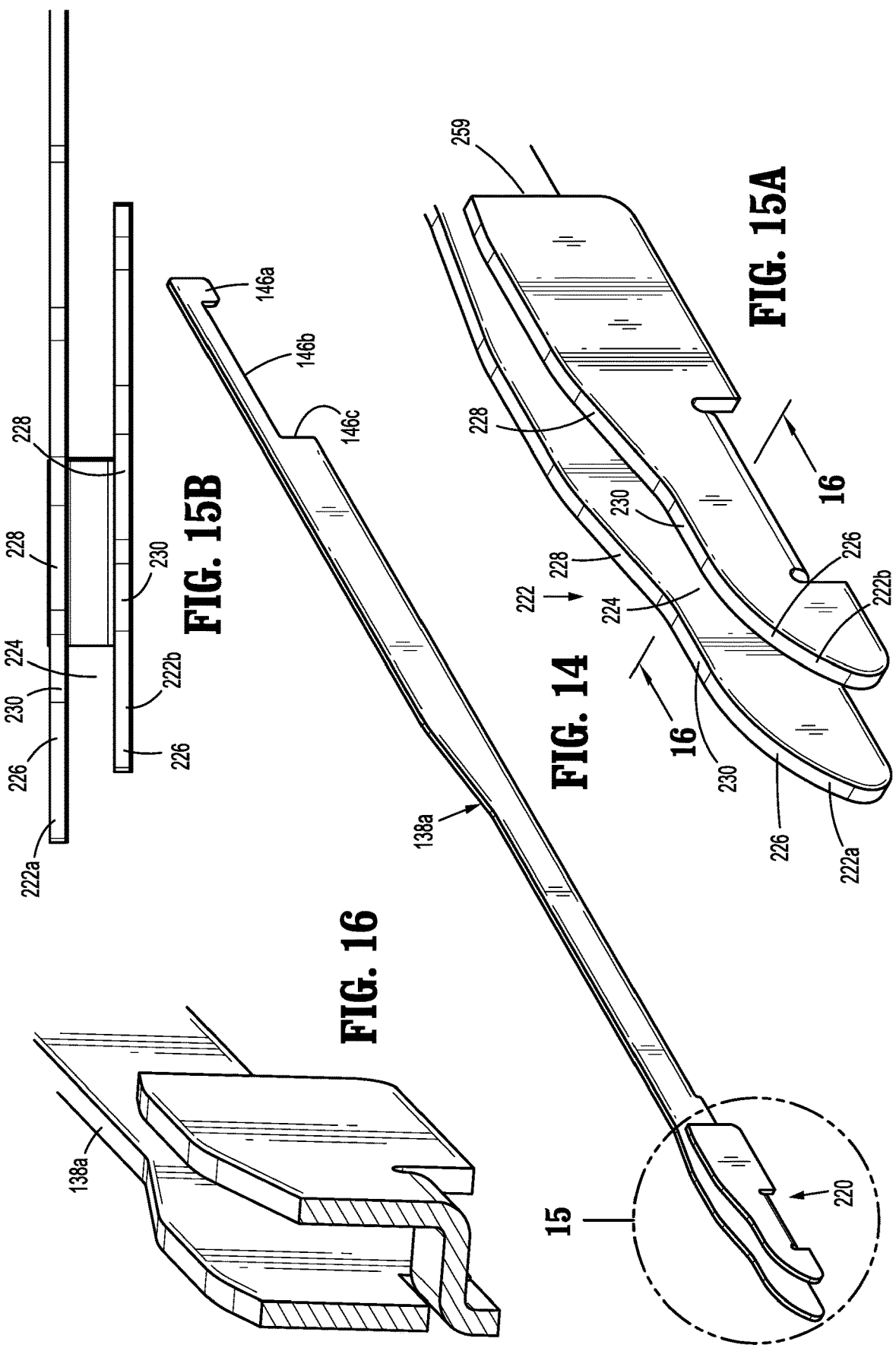

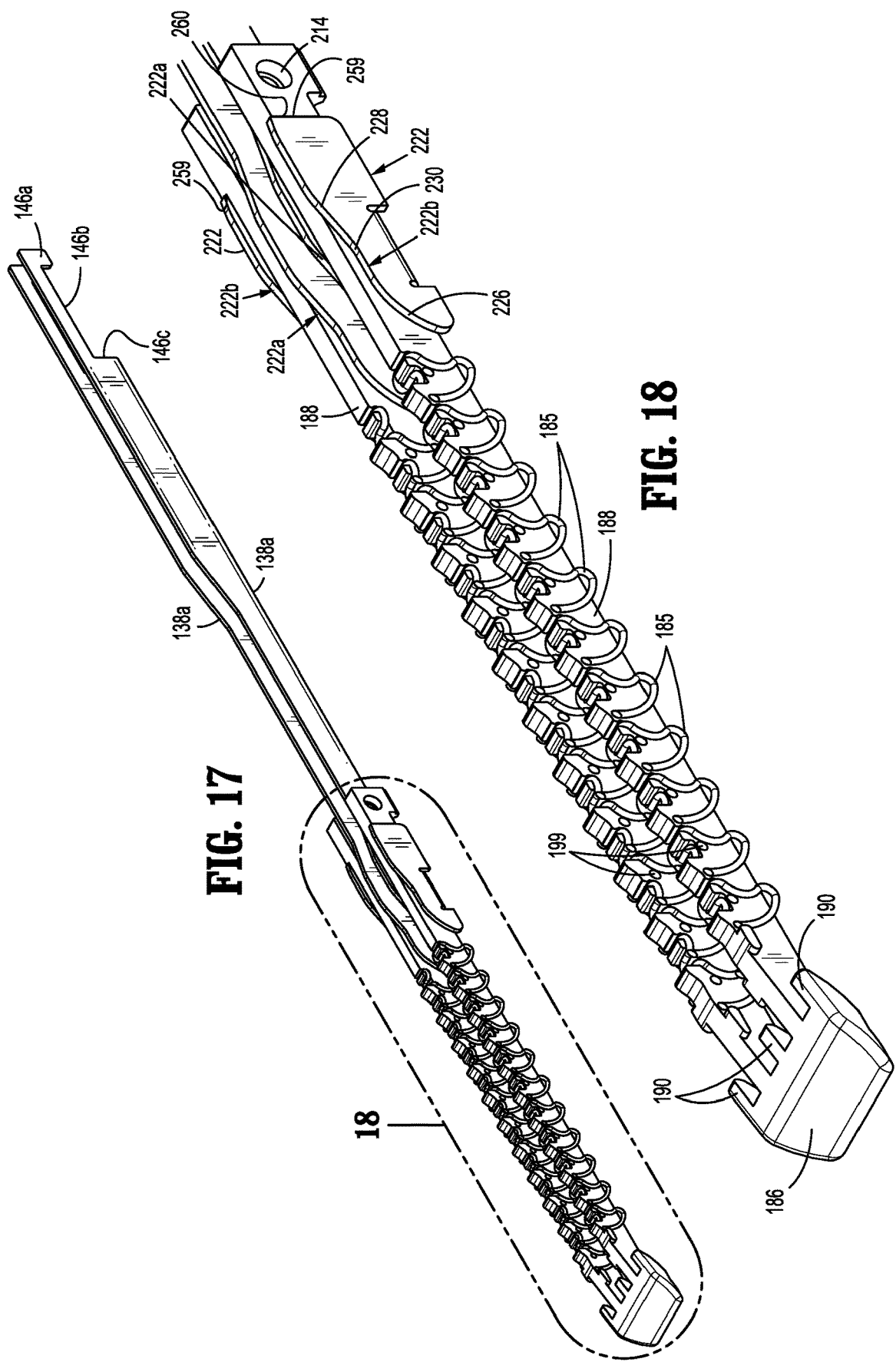

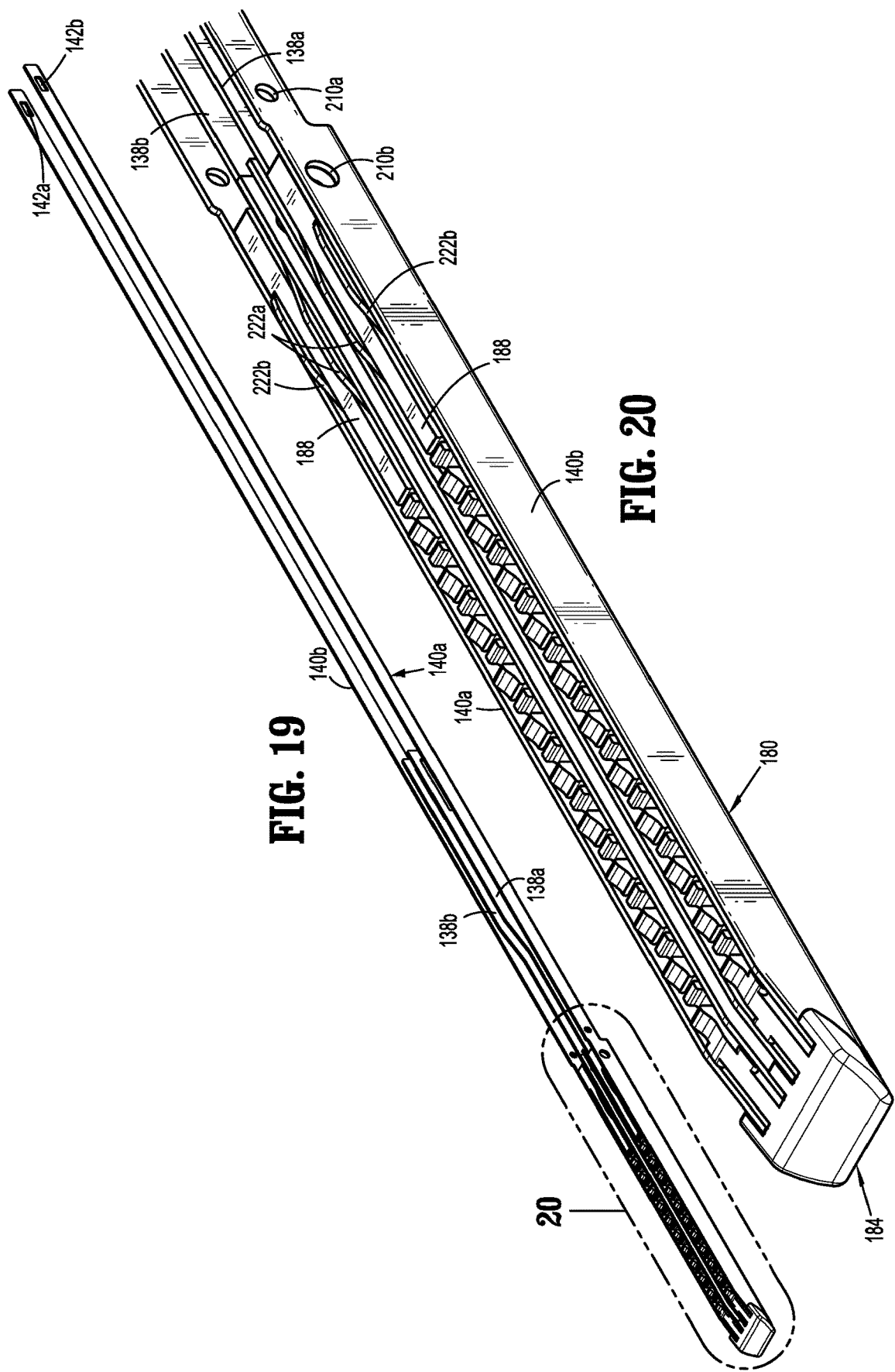

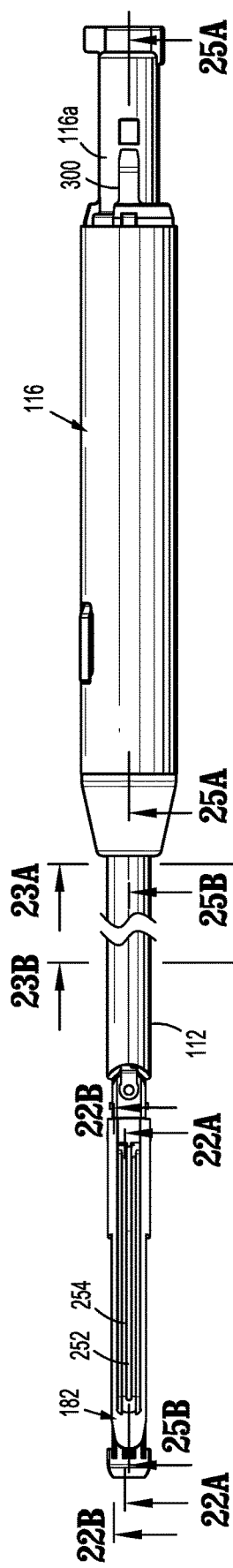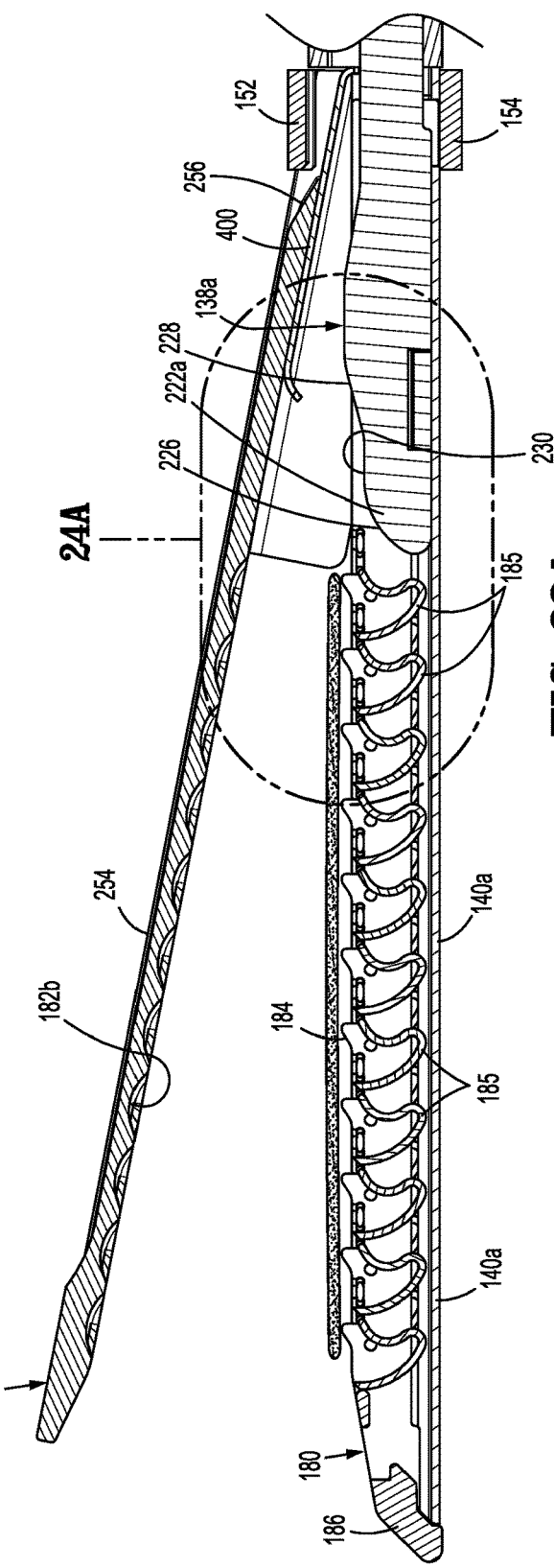
FIG. 21
FIG. 22A

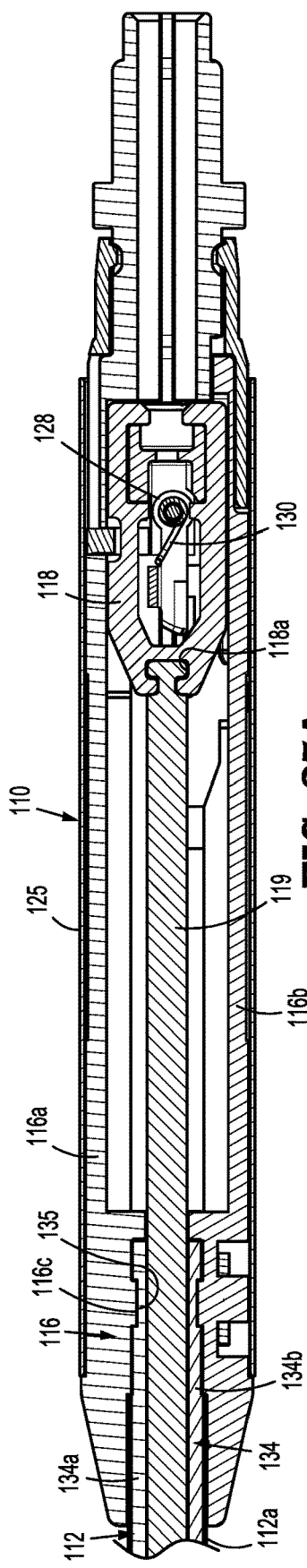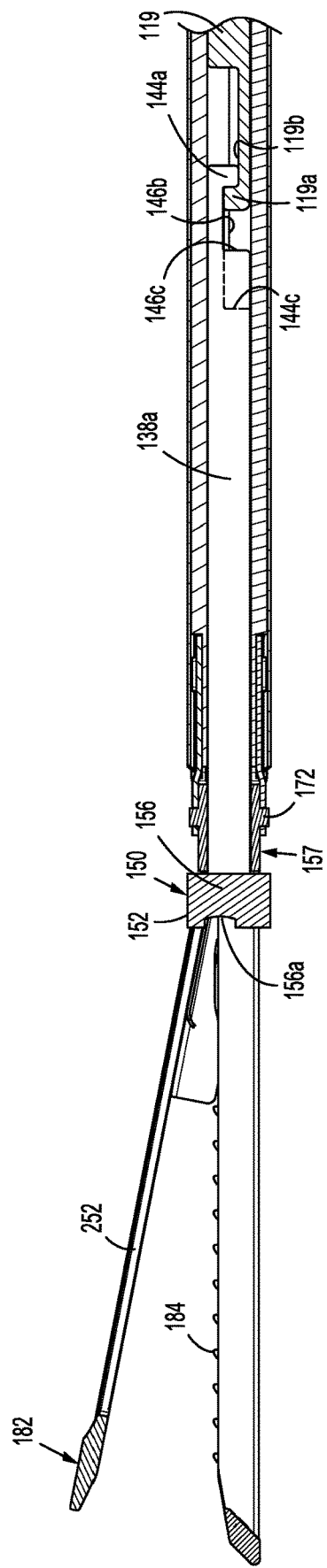
FIG. 25A
FIG. 25B

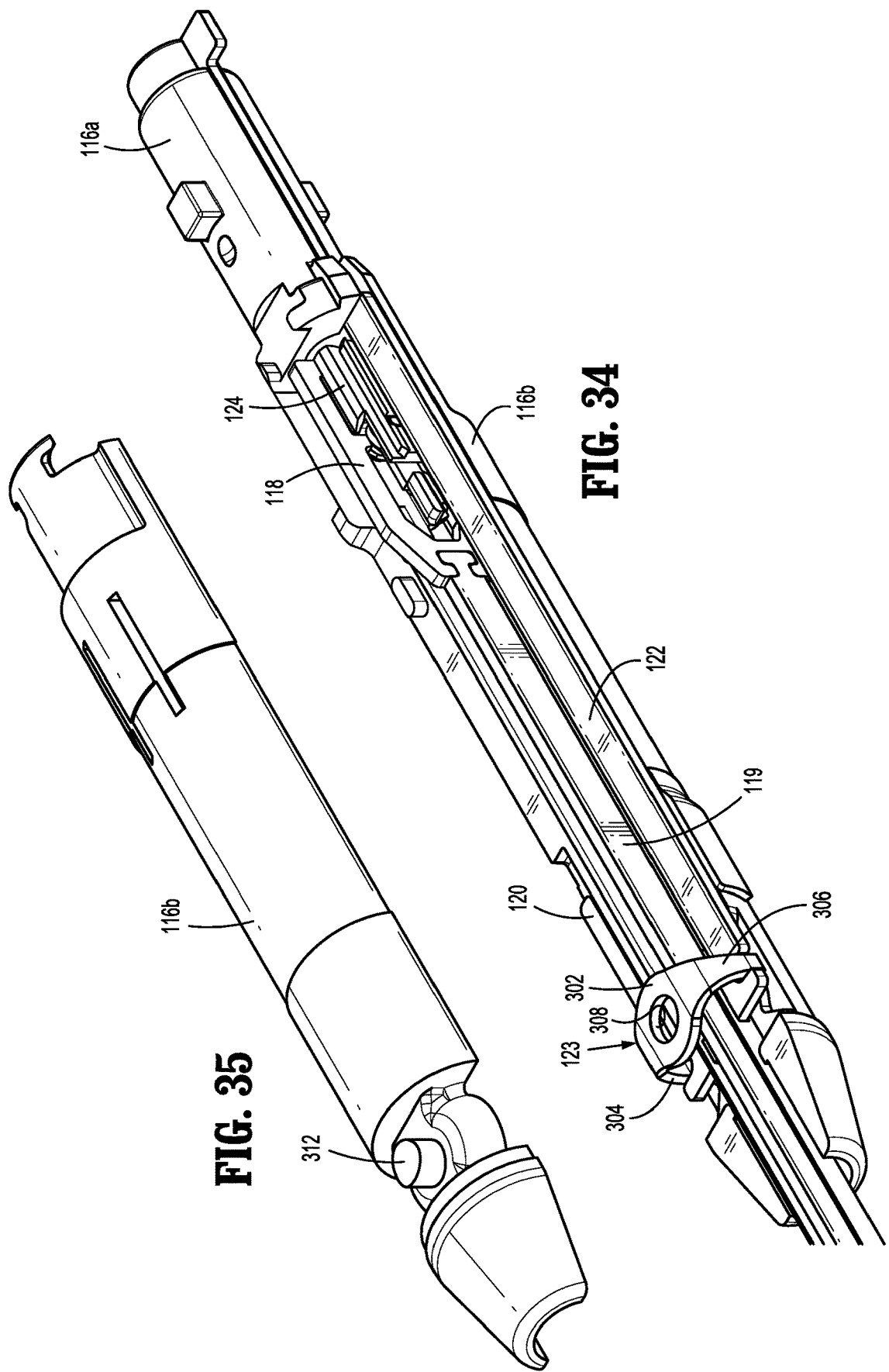

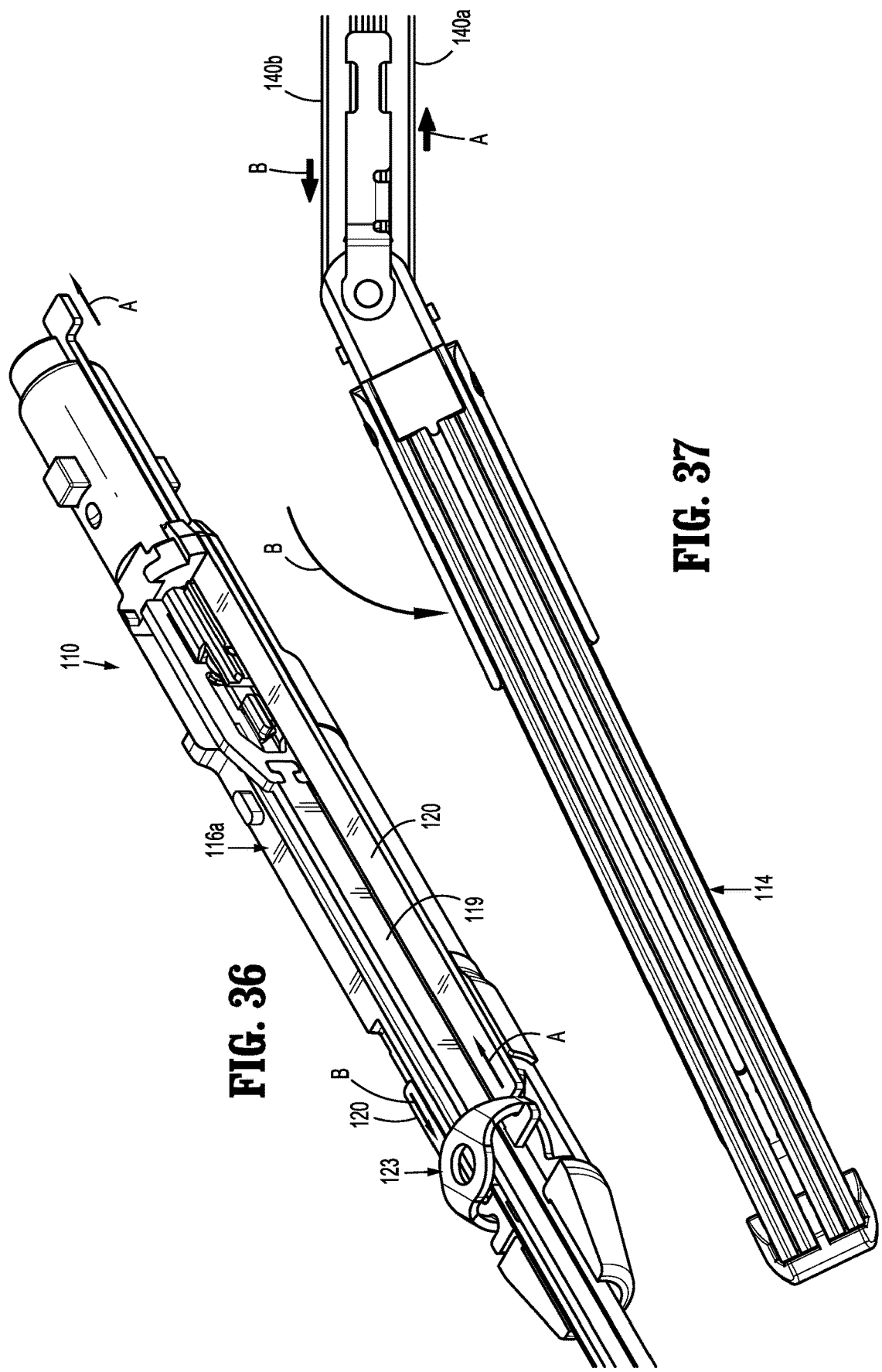

ENDOSCOPIC STAPLER

CROSS-REFERENCE TO RELATED APPLICATIONS

This application is a continuation of U.S. patent application Ser. No. 14/994,228, filed Jan. 13, 2016, now U.S. Pat. No. 10,463,368, which claims the benefit of and priority to U.S. Provisional Patent Application No. 62/145,857 filed Apr. 10, 2015, the entire disclosures each of which are incorporated by reference herein.

BACKGROUND

Technical Field

The present disclosure relates to surgical staplers, and more particularly, to surgical staplers for endoscopic use. The present disclosure also relates to surgical staples for use with endoscopic surgical staplers.

Background

Surgical staplers typically include a cartridge housing a plurality of staples, an anvil for forming the staples as the staples are ejected from the cartridge, and a knife to effect simultaneous dissection and suturing of tissue. When compared to applying manually threaded sutures, the use of surgical staplers to suture and dissect tissue has increased the speed of the surgical procedure and thus, minimized patient trauma.

In an endoscopic surgical procedure, a surgical stapler is inserted through a small incision in the skin or through a cannula to access a surgical site. Due to the complexity of known surgical staplers as well as the staple size requirements of known staple forming apparatus, a continued need exists for small diameter surgical staplers suitable for endoscopic use.

SUMMARY

The present disclosure is directed to a surgical stapler having a tool assembly including an anvil and a staple cartridge having a series of staples which are supported and configured to be rotatably ejected from the staple cartridge into the anvil to suture tissue. The manner in which the staples are supported and ejected from within the staple cartridge facilitates the use of a small diameter tool assembly that includes staples capable of suturing thicker tissues than would normally be associated with tool assemblies with such a small diameter. In embodiments, the surgical stapler includes at least one firing cam having staggered cam members and the staples are configured with staggered legs. Each of the staple legs has a D-shaped configuration when deformed.

In one aspect of the disclosure, a surgical stapler includes a shaft portion and a tool assembly supported on a distal end of the shaft portion. The tool assembly includes an anvil and a cartridge assembly having a cartridge body including at least one leg defining a plurality of notches and a plurality of staples. Each of the staples has an intermediate portion interconnecting first and second staple legs. The intermediate portion of each of the staples has a first end connected to the first leg and a second end connected to the second leg, wherein the first and second ends of the intermediate portion are axially offset from each other. The surgical stapler includes at least one firing cam having a distal end defining a cam member including first and second cam surfaces. The first and second cam surfaces are axially offset from each other. The cam member is movable within the tool assembly to move the first and second cam surfaces into sequential engagement with the first and second staple legs, respectively, of each of the plurality of staples, wherein engagement between the cam member and the first and second staple legs of each of the plurality of staples effects rotational movement of each of the plurality of staples to fire each of the plurality of staples from the cartridge body.

In embodiments, each notch of the plurality of notches is configured to rotatably support one of the staples of the plurality of staples.

In some embodiments, the at least one leg of the cartridge body defines a plurality of cutouts. Each of the plurality of cutouts is spaced from adjacent notches of the plurality of notches and is configured to receive a first portion of the intermediate portion of one of the staples of the plurality of staples.

In embodiments, the intermediate portion of each of the staples is S-shaped and includes a distal U-shaped portion that is configured to be received in a respective one of the cutouts of the plurality of cutouts on the at least one leg of the cartridge body.

In certain embodiments, each of the notches of the plurality of notches is configured to rotatably receive a proximal portion of the intermediate portion of a respective one of the staples of the plurality of staples.

In embodiments, the first and second staple legs of each of the staples of the plurality of staples has a curved configuration and each of the first and second staple legs defines a D-shape when formed against the anvil.

In some embodiments, each notch of the plurality of notches includes a cylindrical slot that is configured to receive the proximal portion of the intermediate portion of a respective one of the staples of the plurality of staples in a snap-fit manner.

In certain embodiments, the at least one leg of the cartridge body includes two spaced legs and the plurality of notches is spaced axially along each of the two spaced legs, wherein each of the plurality of notches rotatably supports one of the staples of the plurality of staples.

In embodiments, the surgical stapler includes first and second cartridge channels. Each of the first and second cartridge channels has a distal end defining a U-shaped member and each of the two spaced legs of the cartridge body is secured within a respective one of the U-shaped members.

In some embodiments, the at least one firing cam includes first and second firing cams. Each of the cam members of the first and second firing cams has a U-shape and is positioned about one of the two spaced legs of the cartridge body and within the U-shaped member of one of the first and second cartridge channels.

In certain embodiments, the surgical stapler includes a pivot member pivotably secured to the distal end of the shaft portion and fixedly secured to each of the first and second cartridge channels.

In embodiments, the surgical stapler includes a first articulation link having a distal end secured to a proximal end of the first cartridge channel and a second articulation link having a distal end secured to a proximal end of the second cartridge channel. The first and second articulation links are axially movable to effect axial movement of the first and second cartridge channels in relation to each other to pivot the pivot member in relation to the shaft portion.

In some embodiments, a pivotable articulation member interconnects the first articulation link to the second articulation link such that movement of the first articulation link in one direction effects movement of the second articulation link in an opposite direction.

In certain embodiments, each of the first and second staple legs of each of the plurality of staples has a tapered tip.

In embodiments, the at least one leg of the cartridge body includes a plurality of dimples and each of the plurality of dimples is positioned to engage one of the first and second legs of one of the staples of the plurality of staples to stabilize the staple on the cartridge body.

In another aspect of the disclosure, a surgical staple is described that includes a first curved leg, a second curved leg, and an intermediate portion interconnecting the first curved leg to the second curved leg. The intermediate portion of the staple has a first end connected to the first curved leg and a second end connected to the second curved leg, wherein the first and second ends of the intermediate portion are axially offset from each other.

In some embodiments, the intermediate portion of the staple is S-shaped and includes a distal U-shaped portion and a proximal portion.

In certain embodiments, each of the first and second legs includes a tapered tip.

In embodiments, the first and second legs of the staple is configured to have a D-shape when formed against an anvil.

BRIEF DESCRIPTION OF THE DRAWINGS

Various embodiments of the presently disclosed small diameter surgical stapler are described herein with reference to the drawings, wherein:

FIG. 1A is a side perspective view from the distal end of a stapler reload of the surgical stapler shown in FIG. 1;

FIG. 2 is a side perspective view from the proximal end of the surgical stapler reload shown in FIG. 1A;

FIG. 3 is a side perspective, exploded view of the surgical stapler reload shown in FIG. 1A;

FIG. 3A is a top, perspective, exploded view of a distal end of the upper housing half-section of a proximal body portion, a pivot member, and a connecting member of the surgical stapler reload shown in 3;

FIG. 9 is a side, perspective view of a cartridge channel of the stapler reload shown in FIG. 3;

FIG. 10 is a top view of the cartridge channel shown in FIG. 9;

FIG. 11 is an enlarged view of the indicated area shown in FIG. 10;

FIG. 12 is an enlarged view of the indicated area of detail shown in FIG. 9;

FIG. 13 is a perspective, cross-sectional view taken along section line 13-13 of FIG. 12.

FIG. 14 is a side, perspective view of a staggered firing cam of the stapler reload shown in FIG. 3;

FIG. 15A is an enlarged view of the indicated area of detail shown in FIG. 14;

FIG. 15B is a top view of the distal end of the staggered firing cam shown in FIG. 14;

FIG. 16 is a perspective, cross-sectional view taken along section line 16-16 of FIG. 15;

FIG. 17 is a side, perspective view of the cartridge assembly of the stapler reload shown in FIG. 3 supported on a distal end of the firing cams;

FIG. 18 is an enlarged view of the indicated area of detail shown in FIG. 17;

FIG. 19 is a side, perspective view of the cartridge assembly of the stapler reload shown in FIG. 3 supported on the distal ends of the cartridge channels and firing cams;

FIG. 20 is an enlarged view of the indicated area of detail shown in FIG. 19;

FIG. 21 is a top view of the stapler reload shown in FIG. 1A with the tool assembly in an unapproximated position;

FIG. 22A is a cross-sectional view taken along section line 22A-22A of FIG. 21;

FIG. 25A is a cross-sectional view taken along section line 25A-25A of FIG. 21;

FIG. 25B is a cross-sectional view taken along section line 25B-25B of FIG. 21;

FIG. 34 is a top perspective view of the proximal body portion of the stapler reload with the proximal tube removed and the upper housing half section removed;

FIG. 35 is a top perspective view of the upper housing half section of the proximal body portion of the stapler reload;

FIG. 36 is a top, perspective view of the proximal body portion of the stapler reload shown in FIG. 35 with the proximal tube and the upper housing half section removed and the articulation member rotated; and FIG. 37 is a top view of the tool assembly of the stapler reload, shown in FIG. 26 in an articulated position.

DETAILED DESCRIPTION OF EMBODIMENTS

Figure 1:
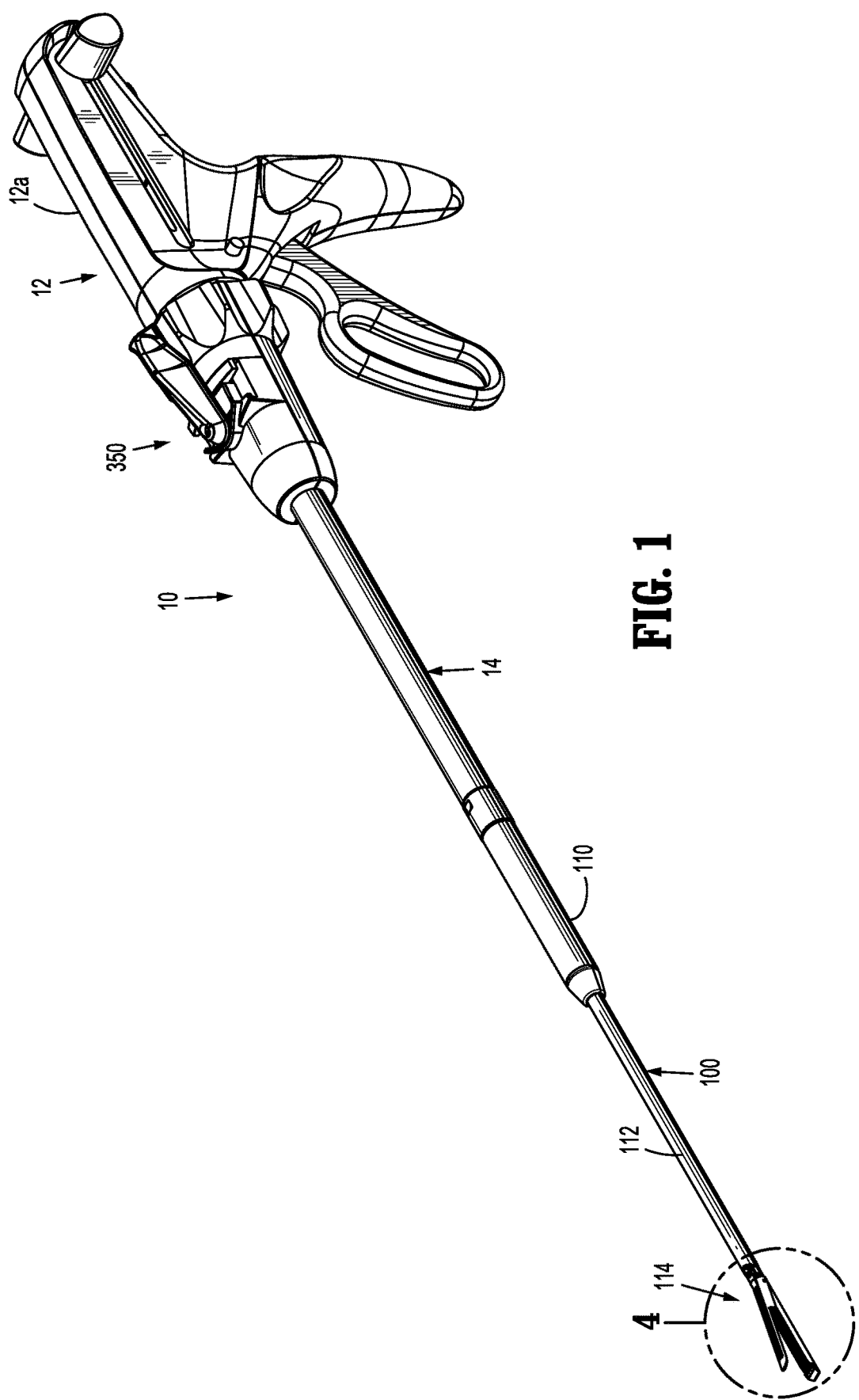
FIG. 1 is a side perspective view of one embodiment of the presently disclosed small diameter surgical stapler in an unapproximated position.

Embodiments of the presently disclosed endoscopic surgical stapler including staples with staggered legs will now be described in detail with reference to the drawings wherein like reference numerals designate identical or corresponding elements in each of the several views. In this description, the term "proximal" is used generally to refer to the portion of the apparatus that is closer to a clinician, while the term "distal" is used generally to refer to the portion of the apparatus that is farther from the clinician. In addition, the term "endoscopic" procedure is used generally to refer to endoscopic, laparoscopic, arthroscopic, and any other surgical procedure performed through a small incision or a cannula inserted into a patient's body. Finally, the term clinician is used generally to refer to medical personnel including doctors, nurses, and support personnel.

The presently disclosed surgical stapler includes a tool assembly which supports a series of staples which are supported and configured to be rotatably ejected from a staple cartridge into an anvil to suture tissue. The manner in which the staples are supported and ejected from within the staple cartridge facilitates the use of a small diameter tool assembly which includes staples capable of suturing thicker tissues than would normally be associated with tool assemblies with such a small diameter. In embodiments, the surgical stapler includes at least one firing cam having staggered cam members and the staples are configured with staggered legs. Each of the staple legs has a D-shaped configuration when deformed.

FIG. 1-2 illustrate the presently disclosed surgical stapler 10 which includes an actuating device 12 having a handle assembly 12a, a body portion 14 which extends distally from the handle portion 12, and a stapler reload 100 supported on a distal end of the body portion 14. The distal end of the body portion 14 is adapted to releasably engage a proximal end of the reload 100 such that actuation of the actuating device 12 effects operation of the reload 100. A suitable actuating device is disclosed in detail in U.S. Pat. No. 5,865,361 ("361 patent") and U.S. Pat. No. 7,143,924 ("924 patent") which are incorporated herein in their entirety by reference. Although the presently disclosed actuating device is illustrated as a manually actuated handle assembly, it is envisioned that other known actuating devices including robotic devices, motorized devices, and/or electrically or mechanically driven devices can be used to actuate the reload 100.

In an alternate embodiment, the reload 100 can be fixedly attached to the distal end of the handle assembly 12 and only a cartridge assembly of a tool assembly can be removable and replaceable. Alternatively, a removable and replaceable reload can also have a removable and replaceable cartridge.

Figure 3B:
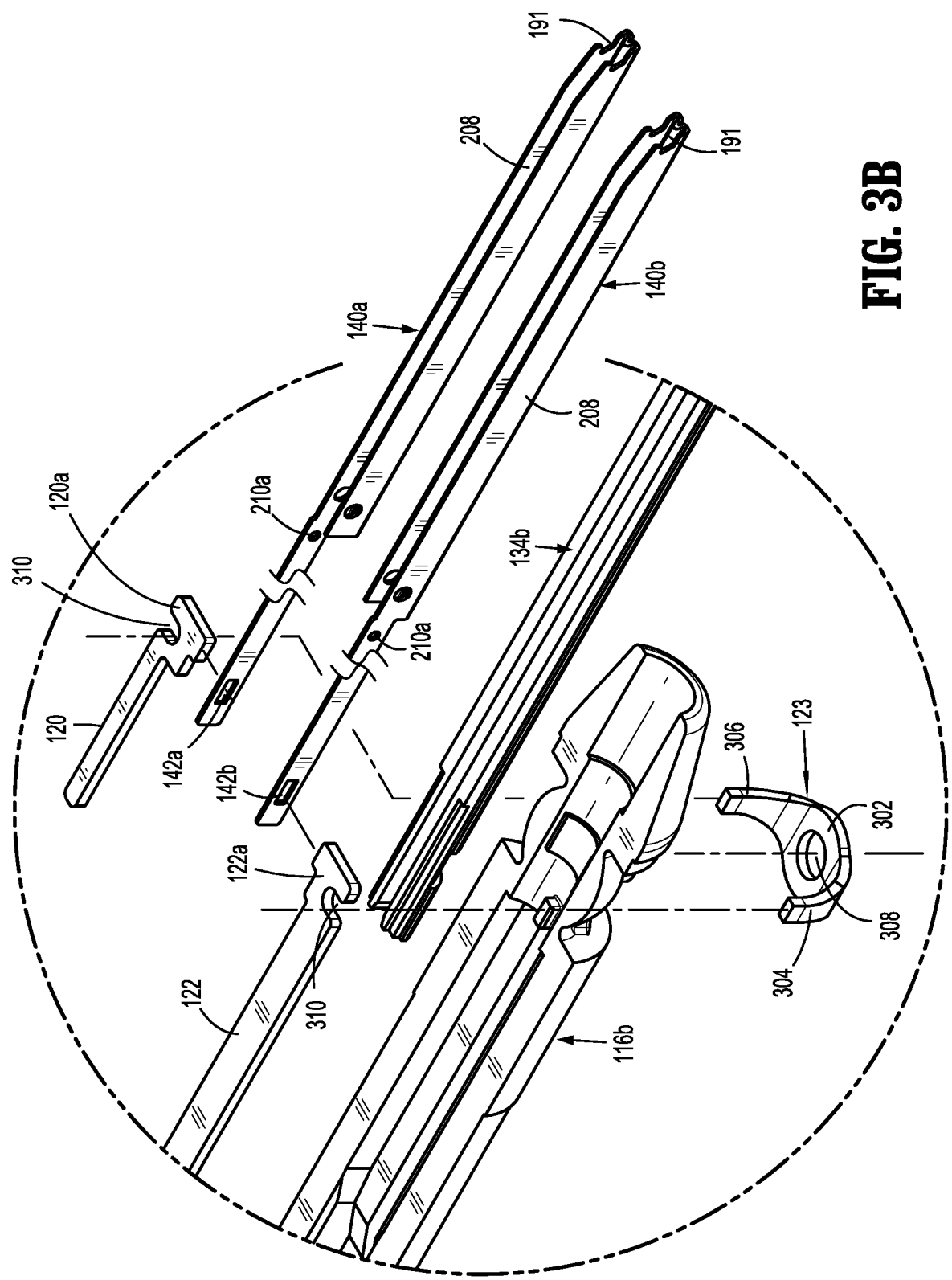
FIG. 3B is an enlarged view of the indicated area of detail shown in FIG. 3.
Figure 3C:
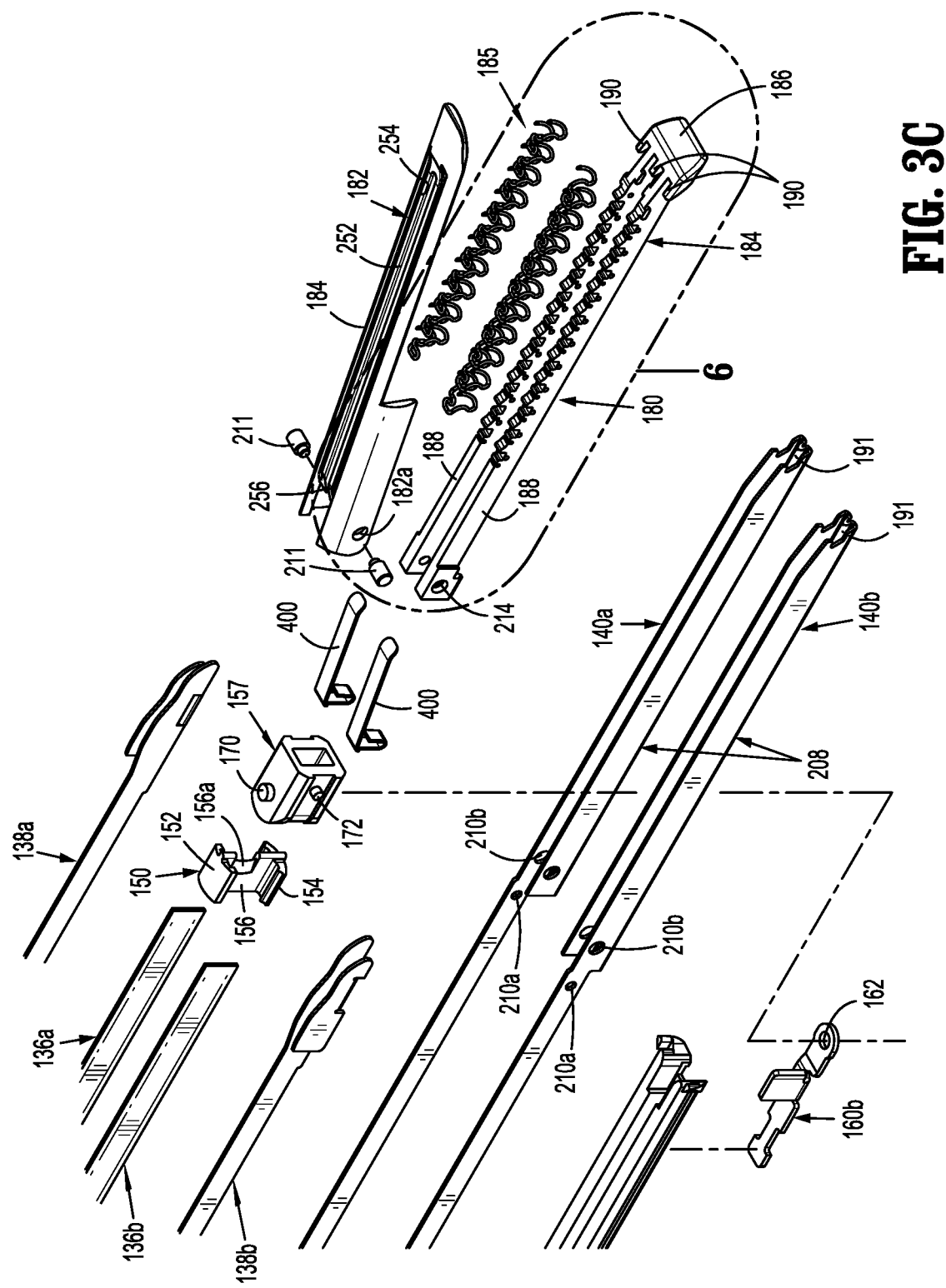
FIG. 3C is an enlarged view of the indicated area of detail shown in FIG. 3.
Figure 4:
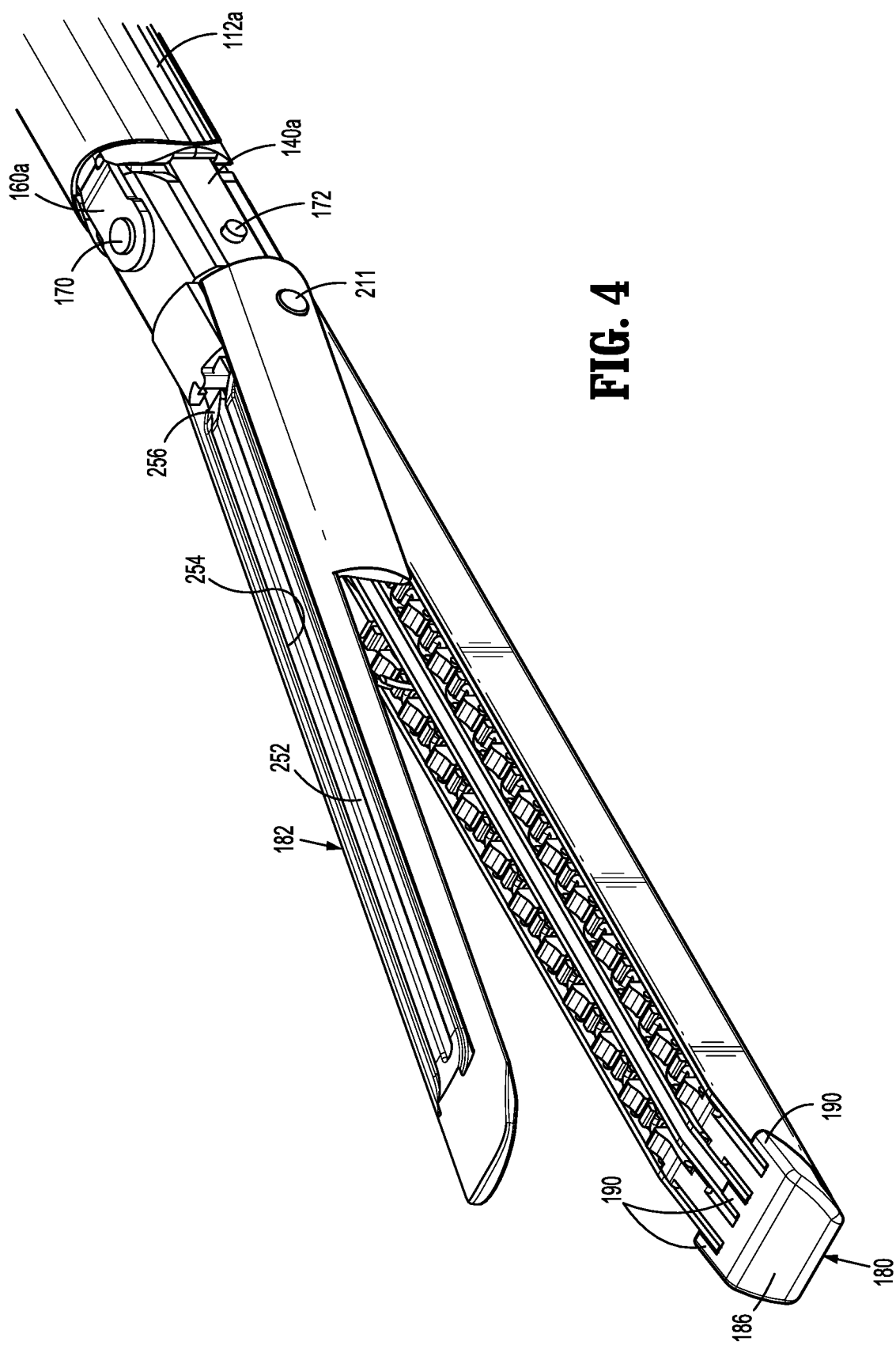
FIG. 4 is an enlarged view of the indicated area of detail shown in FIG. 1.

Referring also to FIGS. 3-3C, the reload 100 includes a proximal body portion 110, an elongated shaft portion 112 and a tool assembly 114. The proximal body portion 110 includes an inner housing 116 (FIG. 25A) defined by an upper housing half-section 116a and a lower housing half-section 116b. The housing half-sections 116a and 116b define channels which slidably receive a proximal drive member 118, a first articulation link 120 and a second articulation link 122. The housing half-sections 116a and 116b are received within a proximal body tube 125.

The first articulation link 120 is connected to the second articulation link 122 by an articulation member 123 which will be described in detail below. The proximal drive member 118 supports a drive coupler 124 that is adapted to engage a control rod (not shown) of the actuating device 12 (FIG. 1) to operate the tool assembly 114 of the reload 100. The proximal drive member 118 also supports a locking assembly 126 which includes a locking device 128 and a spring 130. Operation of the drive coupler 124 and the locking assembly 126 are described in the '361 patent which is incorporated herein by reference. As such, the drive coupler 124 and locking assembly 126 will not be described in further detail herein. A distal end of the proximal drive member 118 includes a T-shaped recess 118a. In addition, the distal ends of the first articulation link 120 and the second articulation link 122 include hook portions 120a and 122a, respectively (FIG. 3B). Each of these hook portions 120a and 122a and the T-shaped recess 118a are described in further detail below.

The elongated shaft portion 112 of the reload 100 includes an inner housing 134 (FIG. 25A) defined by upper and lower housing half-sections 134a and 134b which are received within a shaft portion tube 112a. A proximal end of the inner housing 134 of the elongated shaft portion 112 is received within the distal end of the inner housing 116 of the proximal body portion 110 and includes an annular recess 135. The annular recess 135 receives a protrusion 116c (FIG. 25A) formed within the inner housing 116 to axially secure the inner housing 116 of the proximal body portion 110 to the inner housing 134 of the shaft portion 112. The upper and lower housing half-sections 134a, 134b of the elongated shaft portion 112 define internal channels (not shown) which slidably receive a pair of distal drive members 136a, 136b, a pair of firing cams 138a, 138b, and a pair of cartridge channel members 140a, 140b. A proximal end of each of the cartridge channels 140a, 140b defines a cutout 142a, 142b, respectively. The cutouts 142a, 142b of the cartridge channels 140a, 140b receive one side of the hook portions 120a, 122a (FIG. 3B), respectively, of the first and second articulation links 120, 122 such that linear movement of the first and second articulation links 120, 122 effects linear movement of the cartridge channels 140a,140b as described in further detail below.

A proximal end of each of the distal drive members 136a, 136b includes a hook portion 144a and defines a recess 144b. Similarly, the proximal end of the firing cams 138a, 138b includes a hook portion 146a and define a recess 146b. Each of the recesses 144b, 146b is defined by a distal wall 144c, 146c, respectively. The distal wall 146c defining each recess 146b of the firing cams 138a, 138b is positioned distally of the distal wall 144c defining each recess 144b of the distal drive members 136a, 136b. The proximal drive member 118 and the proximal end of the distal drive members 136a, 136b are connected by a drive member link 119. The drive member link 119 has a proximal end configured to be received in the T-shaped slot 118a of the proximal drive member 118. A distal end of the drive member link 119 includes a hook portion 119a and defines a recess 119b. The hook portion 119a is received within the recesses 144b, 146b of the distal drive members 136a, 136b and the firing cam 138a, 138b, respectively, such that the hook portions 144a, 146a of the distal drive members 136a, 136b and the firing cams 138a, 138b, respectively, are slidably received within the recess 119b of the drive member link 119. As such, movement of the proximal drive member 118 effects corresponding movement of the drive member link 119. As the drive member link 119 is moved distally, the hook portion 119a of the drive member link 119 moves within the recesses 144b and 146b of the distal drive members 136a, 136b and the firing cams 138a, 138b, respectively. When the hook member 119a engages the distal walls 144c, 146c defining the recesses 144b and 146b of the distal drive members 136a, 136b and the firing cams 138a, 138b, respectively, distal movement of the drive member link 119 will effect corresponding distal movement of the distal drive members 136a, 136b and the firing cams 138a, 138b, respectively. As discussed above, the distal wall 146c of the recesses 146c of the firing cams 138a, 138b are positioned distally of the distal walls 144c of the distal drive members 136a, 136b. As such, distal movement of the drive member link 119 will effect distal movement of the distal drive members 136a, 136b prior to effecting distal movement of the firing cams 138a, 138b as described in further detail below. It is envisioned that the proximal drive member 118 and the drive member link 119 can be formed as a unitary component. As best shown in FIG. 3C, the distal end of the distal drive members 136a and 136b are secured to a working member 150 such as by welding. Alternately, other securement techniques can be used to secure the distal end of the drive members 136a, 136b to the working member 150. In one embodiment, the working member 150 includes an upper beam 152, a lower beam 154 and a vertical strut 156 interconnecting the upper and lower beams 152, 154. A cutting edge 156a is formed on or supported on a distal end of the vertical strut 156. The vertical strut 156 is movably positioned between the cartridge channels 140a, 140b, the firing cams 138a, 138b and the legs 188 of the cartridge body 184 as described in further detail below. The working member 150 is positioned and configured to move through the tool assembly 114 when the distal drive members 136a, 136b are moved distally within the elongated shaft portion 112 to actuate the tool assembly 114.

Referring again to FIGS. 3 and 3A, a pivot member 157 is secured to a distal end of the shaft housing half-sections 134a, 134b by upper and lower connecting members 160a, 160b. Each connecting member 160a, 160b includes a distal end which defines an opening 162 and a proximal end 164 which has a stepped configuration. The stepped configuration of the proximal end 164 of each connecting member 160a, 160b is received within a cutout 166 formed in the distal end of each of the upper and lower shaft housing half-sections 134a, 134b to axially fix the upper and lower connecting members 160a, 160b to the upper and lower shaft housing half-sections 134a, 134b, respectively. The openings 162 of each of the upper and lower connecting members 160a, 160b receive a respective pivot pin 170 (only one shown, FIG. 3A) formed on the upper and lower surfaces of the pivot member 157 to pivotally secure the pivot member 157 to the shaft housing half-sections 134a, 134b. The pivot member 157 also includes two transversely extending posts 172. Each post 172 is received in an opening 210a (FIG. 3C) formed in one of the cartridge channels 140a, 140b to secure the pivot member 156 between the cartridge channels 140a, 140b.

Referring to FIGS. 3-8, the tool assembly 114 includes a cartridge assembly 180 and an anvil 182. The cartridge assembly 180 (FIG. 6) includes a cartridge body 184 and a plurality of staples 185. The cartridge body 184 includes a tapered distal end 186 and first and second spaced legs 188. The tapered distal end 186 of the cartridge body 184 functions as a tissue guide and includes three proximally extending fingers 190. One of the fingers 190 is positioned on each side of each of the spaced legs 188 with one finger 190 being positioned between the spaced legs 188. Each of the fingers 190 defines a recess 192 with an adjacent leg 188. The recesses 192 receive the distal ends 191 (FIG. 3C) of the cartridge channels 140a, 140b to secure the cartridge body 184 to the distal end of the cartridge channels 140a, 140b.

Each of the first and second spaced legs 188 of the cartridge body 184 includes a series of rectangular cutouts 196 and notches 198 which are spaced along each leg 188 of the cartridge body 184. The rectangular cutouts 196 and spaced notches 198 are configured and dimensioned to releasably engage the staples 185 as described in detail below. A base 198a of each notch 198 has a circular configuration to facilitate rotation of the staples 185 within a respective notch 198 as the staples are formed as described in further detail below. A series of dimples 199 are spaced along inner and outer walls of the legs 188 of the cartridge body 184. The dimples 199 are positioned to engage a proximal leg portion 202a of each staple 185 to secure the staples 185 to the cartridge body 184 as described in detail below.

Figure 5A:
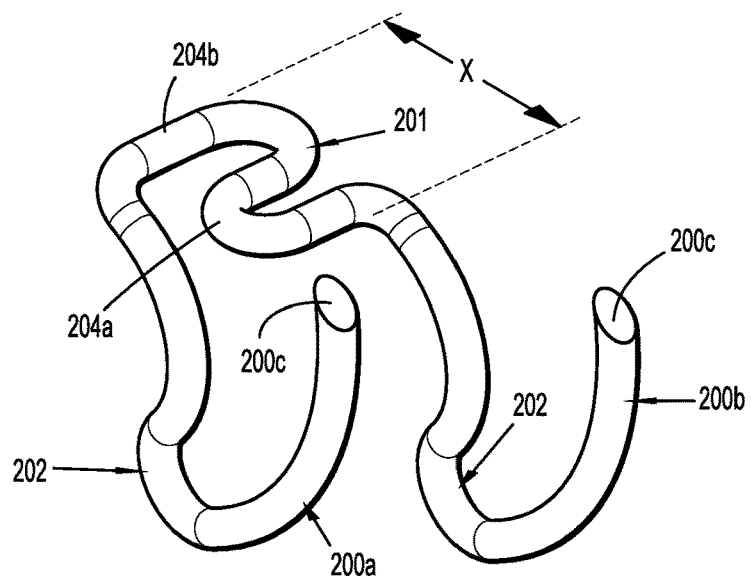
FIG. 5A is a perspective view from one side of a staple of the stapler reload shown in FIG. 3.
Figure 5B:
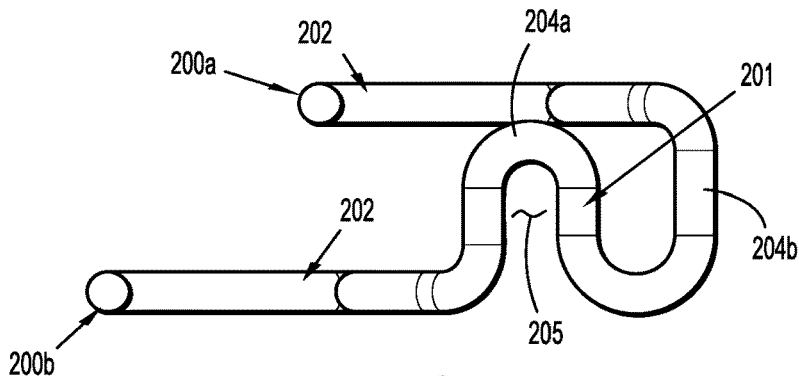
FIG. 5B is a top view of the staple shown in FIG. 5A.
Figure 5C:
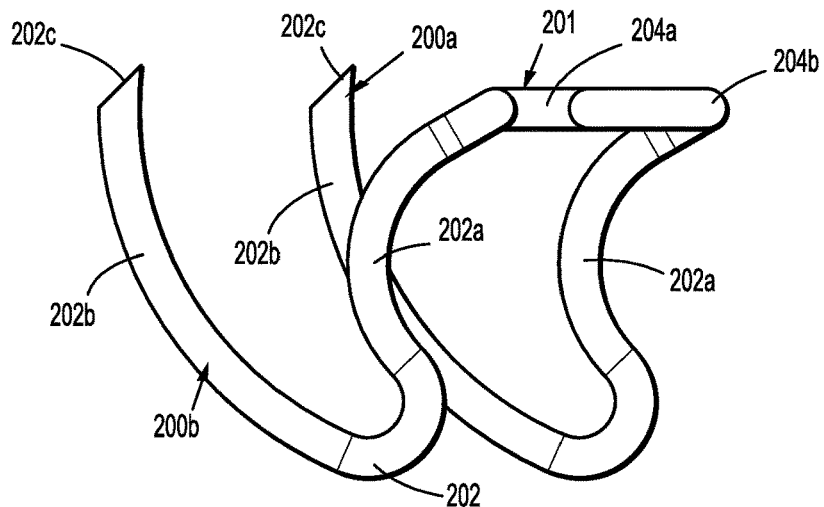
FIG. 5C is a perspective view from the other side of the staple shown in FIG. 3.
Figure 6:
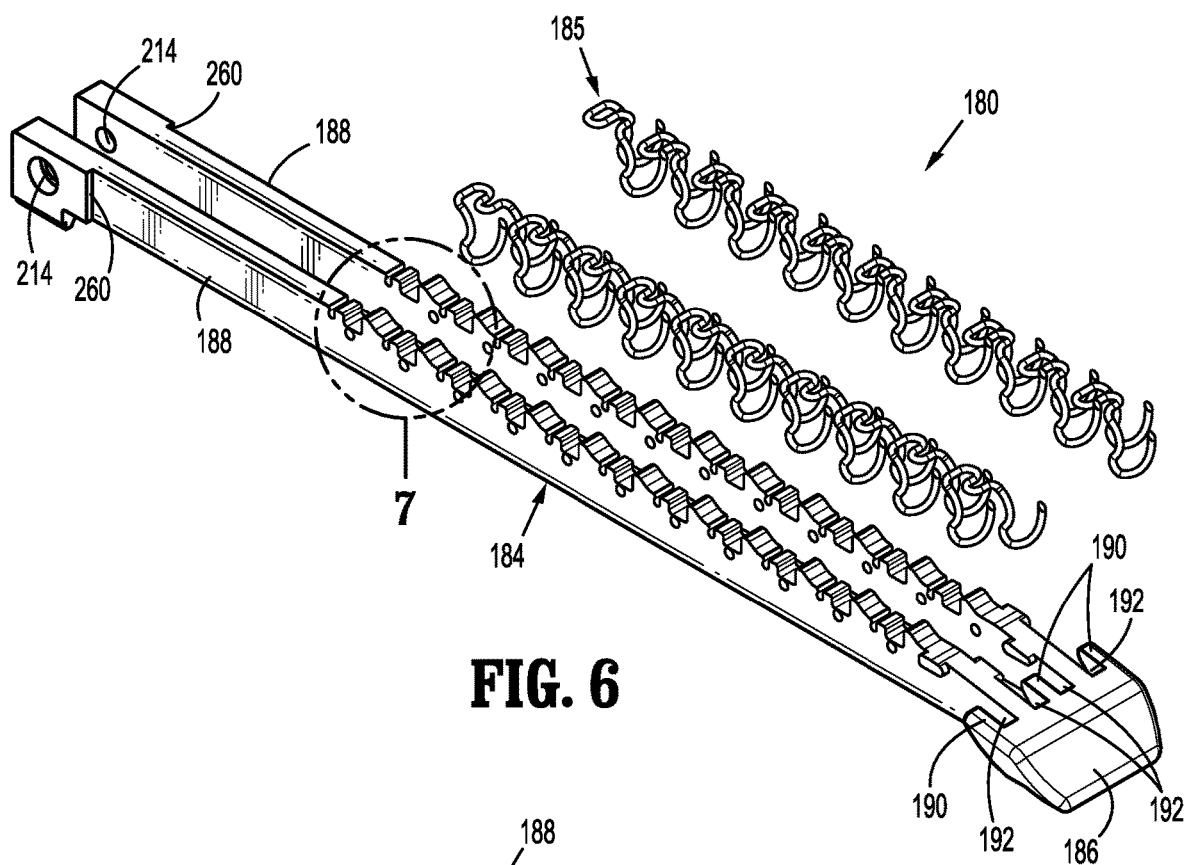
FIG. 6 is an enlarged view of the indicated area of detail shown in FIG. 3C.
Figure 7:
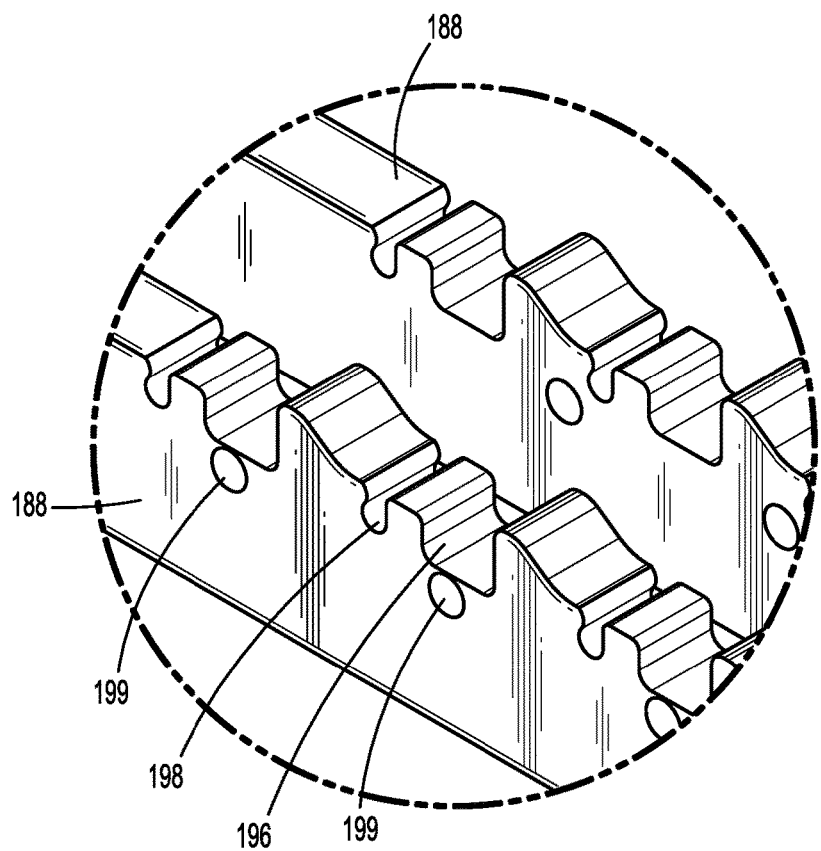
FIG. 7 is an enlarged view of the indicated area of detail shown in FIG. 6.
Figure 7A:
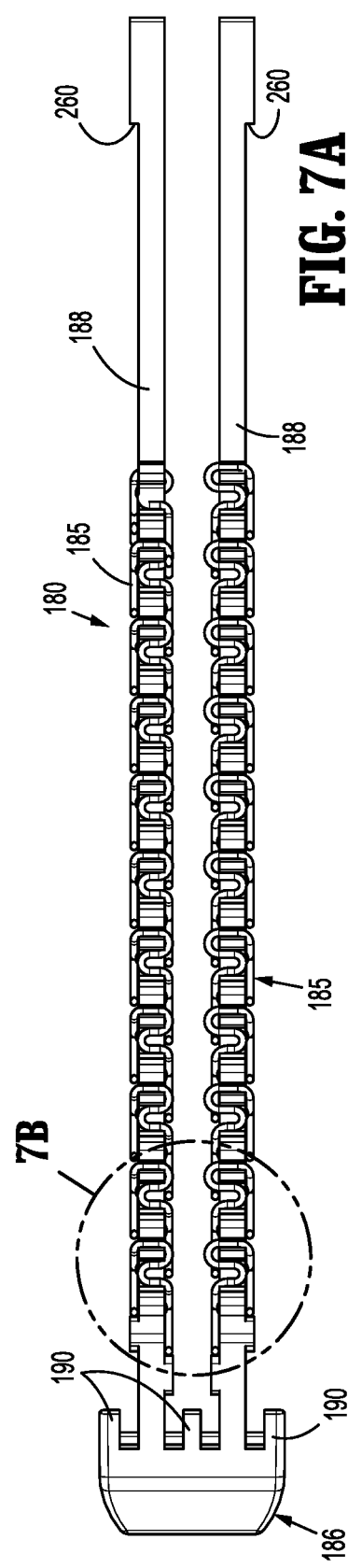
FIG. 7A is a top view of the cartridge assembly of the surgical stapler reload shown in FIG. 1A.
Figure 7B:
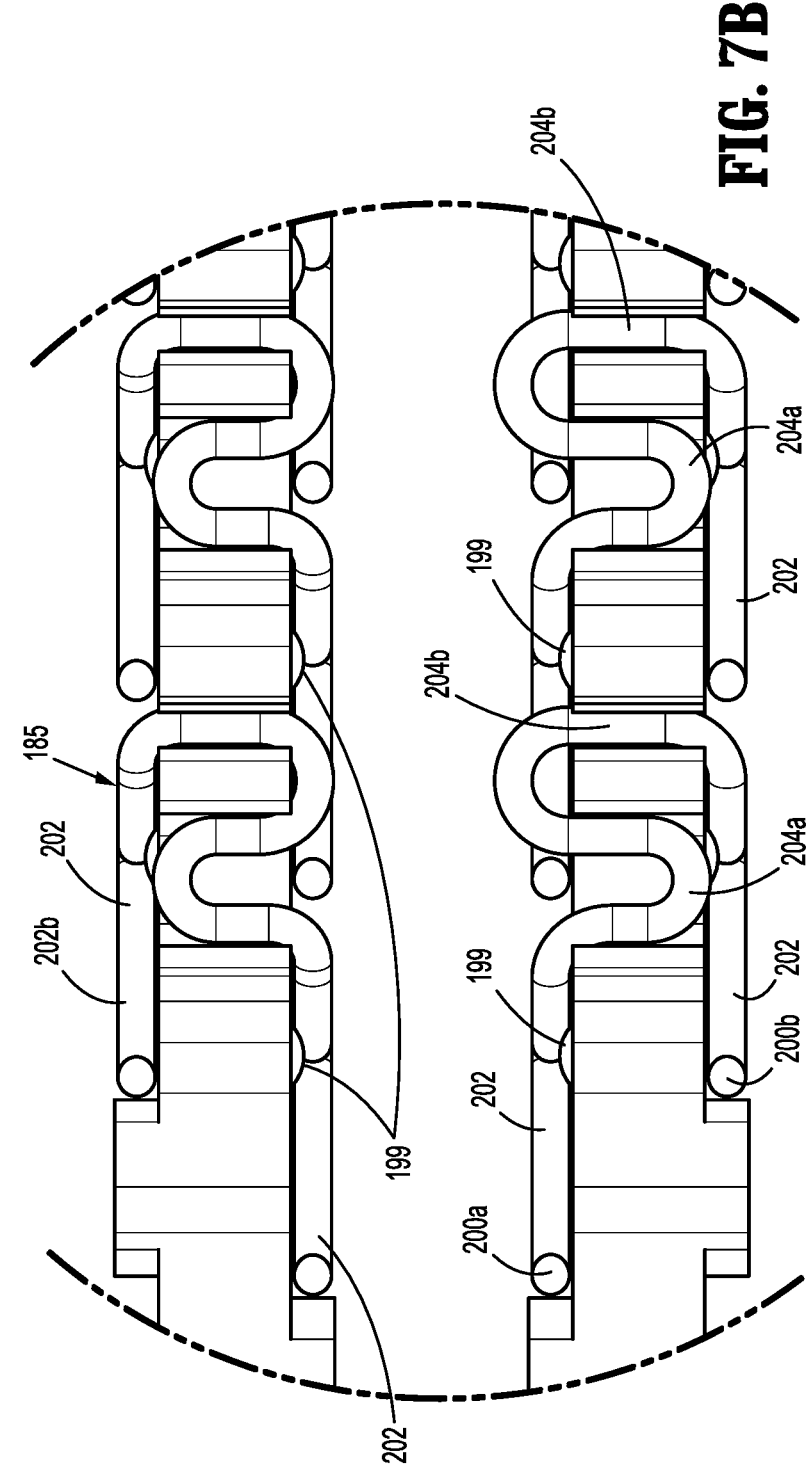
FIG. 7B is an enlarged view of the indicated area of detail shown in FIG. 7A.

Referring to FIGS. 5A-5C, each of the staples 185 includes a pair of staple legs 200a, 200b interconnected by an intermediate portion 201. Each of the staple legs 200a, 200b has tapered tip 200c and a curved, substantially V-shaped body 202. The intermediate portion 201 is S-shaped and has a first end connected to the staple leg 200a and a second end connected to the staple leg 200b.

The V-shaped body 202 of each of the staple legs 200a, 200b includes a proximal leg portion 202a and a distal leg portion 202b. One end of the proximal leg portion 202a is connected to one end of the intermediate portion 201 and the other end of the proximal leg portion 202a is connected to one end of the distal leg portion 202b. The other end of the distal leg portion 202b defines a tapered tip 202c. The distal leg portion 202b is curved upwardly and rearwardly towards the intermediate portion 2013.

Referring again to FIGS. 5A-8, each rectangular cutout 196 of the cartridge body 184 is configured to receive a distal U-shaped portion 204a of the intermediate portion 201 of the staple 185 to secure the staples 185 to a respective leg 188 of the cartridge body 184. In addition, each notch 198 is configured to receive a proximal portion 204b of the intermediate portion 201 of the staple 185 in snap-fit engagement to rotatably secure the staples 185 to respective legs 188 of the cartridge body 184. As discussed above, engagement between the dimples 199 and the proximal leg portion 202a of each staple 185 assists in releasably securing the staples to the cartridge body 184. With the staples 185 secured to the legs 188 of the cartridge body 184, the proximal portion 204b of the intermediate portion 201 of each staple 185 extends transversely across a respective leg 188 of the cartridge body 184 such that the legs 200a, 200b of each staple 185 are positioned on opposite sides of a respective leg 188 of the cartridge body 184 on which the staple 185 is supported.

Figure 8:
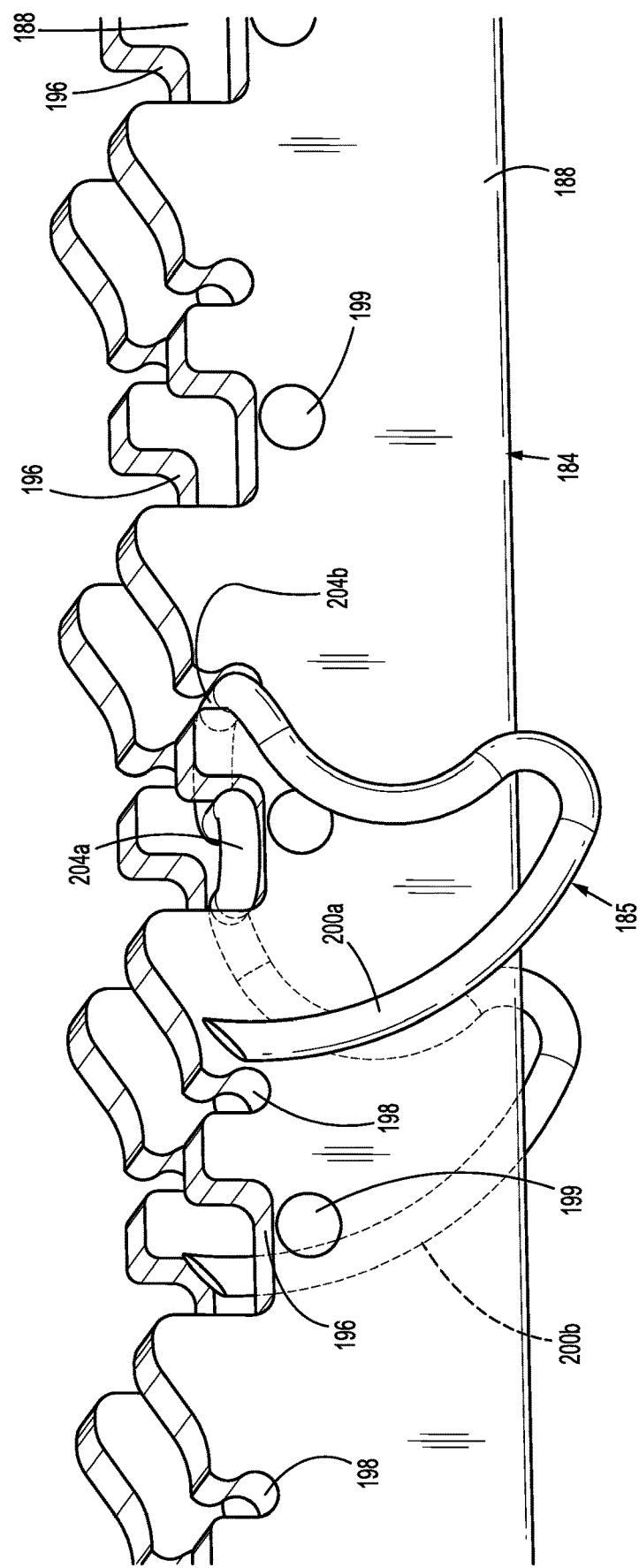
FIG. 8 is a side, cutaway view of the cartridge body supporting a staple.

As best shown in FIG. 8, the legs 200a and 200b of each staple 185 are staggered along a longitudinal axis of the cartridge body 184 by the distance defined by the width "X" (FIG. 5A) of the intermediate body portion 201. In one embodiment, the outer leg 200a of each staple 185 is positioned proximally of the inner leg 200b.

Referring to FIGS. 3-3C and 9-13, each of the cartridge channels 140a and 140b has a substantially similar configuration. As such, only cartridge channel 140b will be described in detail herein. Cartridge channel 140b (FIG. 3) includes a resilient body that extends from the proximal body portion 110 (FIG. 1) of the reload 100 (FIG. 1) to the tool assembly 114. A distal end of each cartridge channel 140b includes a U-shaped member 208 that receives a leg 188 of the cartridge body 184 and defines two openings (FIG. 13) including a proximal opening 210a and a distal opening 210b. The proximal opening 210a receives the post 172 (FIG. 3A) of the pivot member 157 to secure the cartridge channel 140b of the cartridge assembly 180 to the pivot member 157. The distal opening 210b receives a pin 211 (FIG. 3C) that extends through the opening 182a in a proximal end of the anvil 182, through the opening 210b in the cartridge channel 140b, and through an opening 214 (FIG. 6) in the proximal end of each of legs 188 of the cartridge body 184 to secure the proximal end of the legs 188 of cartridge body 184 to the respective cartridge channels 140a, 140b. A distal end 191 of each U-shaped member 208 is received in adjacent recesses 192 (FIG. 6) formed on opposite sides of each leg 188 of the cartridge body 184. The distal end 191 is defined by a pair of cutouts 191a (FIG. 12) and distally extending fingers 191b (FIG. 12). A bottom wall 193 (FIG. 13) of each cartridge channel 140b is w-shaped and defines channels that guide the rotational movement of the staples 185 within the cartridge channel 140b as the staples 185 are ejected from the cartridge assembly 180.

Referring to FIGS. 3-3C and 14-18, the distal end 220 of each firing cam 138a and 138b defines a cam member 222. Each cam member 222 has a curved shape. In certain embodiments, the cam member 222 includes a first portion for moving the staple 185 into engagement with staple forming depressions 182b of the anvil 182 and at least one other portion for forming the staple 185 into a closed configuration. In the embodiment shown, the cam member 222 has a portion for partially forming the staple 185, and a portion for deforming the staple 185 into its final configuration as described in further detail below.

Each cam member 222 of the first and second firing cams 138a, 138b has first and second cam surfaces 222a, 222b that are staggered along the longitudinal axis of the firing cam 138. Each cam member 222 is U-shaped and defines a channel 224 that receives a respective one of legs 188 (FIG. 3C) of the cartridge body 184. The cam members 222 are slidable about the respective legs 188 of the cartridge body 184 to move the first and second cam surfaces 222a, 222b into engagement with the legs 200a, 200b of the staples 185 supported on the respective legs 188 of the cartridge body 184.

Each of the cam surfaces 222a, 222b is curved and defines a first curved surface 226 and a second curved surface 228 which are interconnected by a plateau 230. The cam surfaces 222a, 222b have a height that increases from a distal end of each of the cam surfaces 222a, 222b towards a proximal end of each of the cam surfaces 222a, 222b. The first curved surface 226 of the cam surfaces 222a, 222b is configured to initiate deformation of a leg 200a, 200b of a staple 185 and the second curved surface 228 is configured to complete deformation of the leg 200a, 200b of a staple 185 and to disengage the leg 200a, 200b from the circular base 198a of a respective notch 198 of the cartridge body 184 as described in further detail below.

Figure 32:
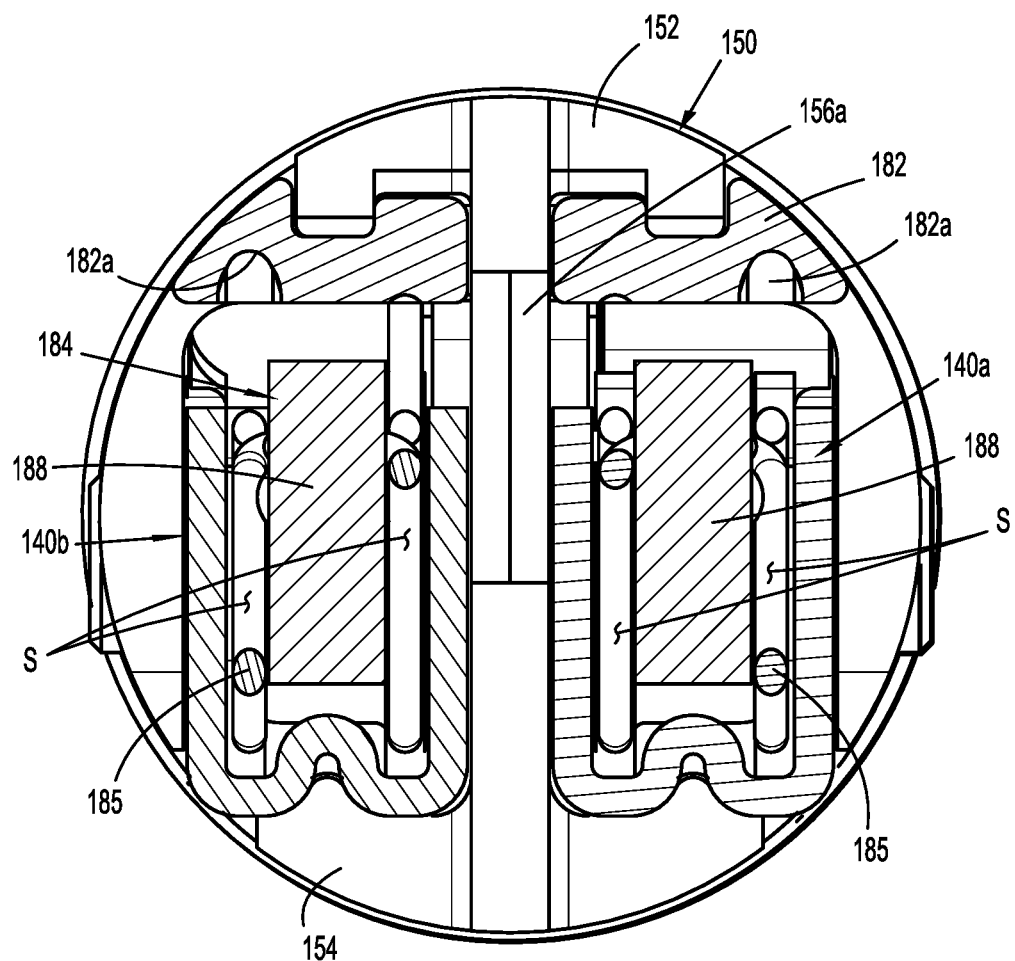
FIG. 32 is a cross-sectional view taken along section line 32-32 of FIG. 26.
Figure 33:
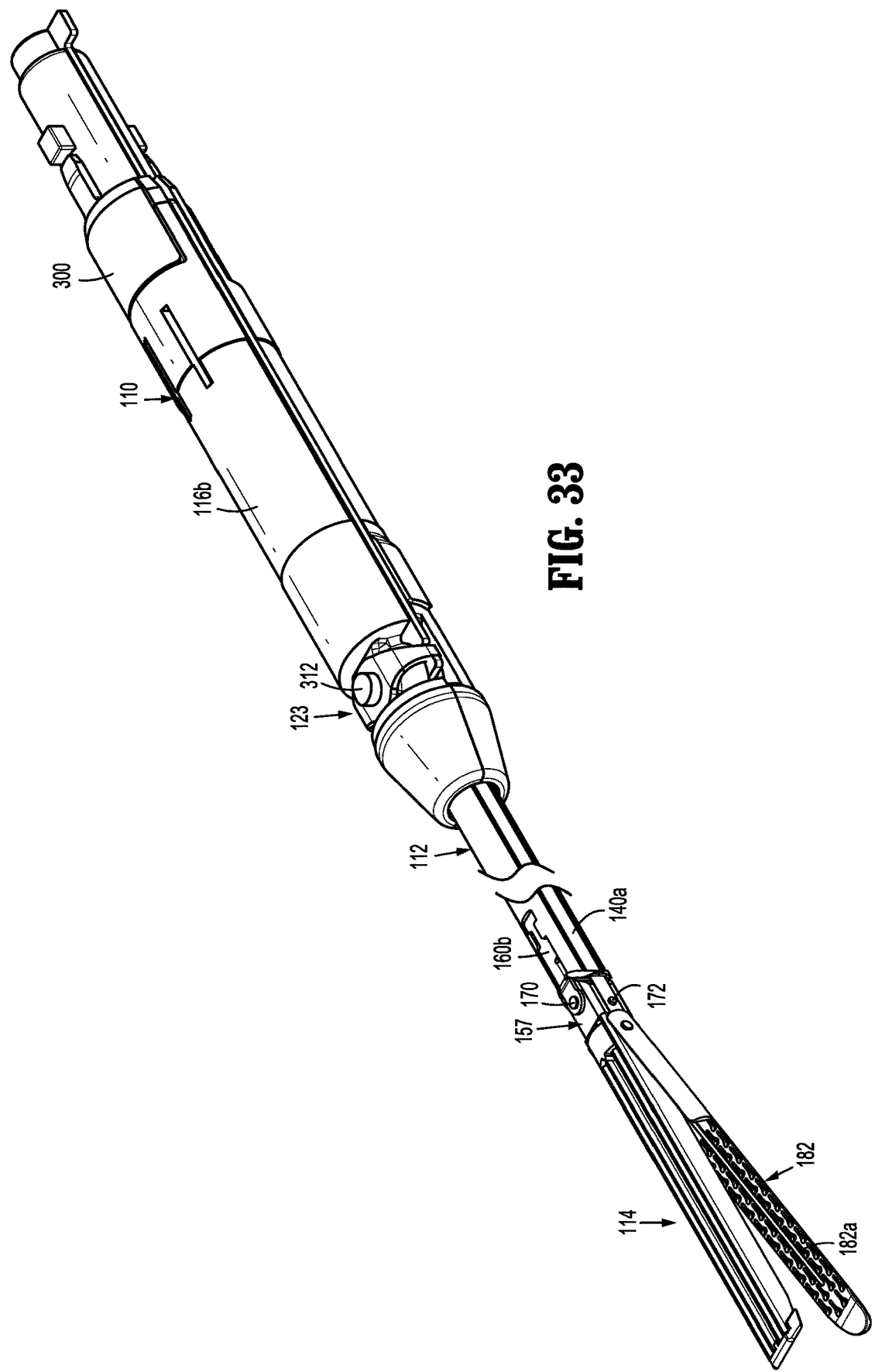
FIG. 33 is a side, perspective view of the stapler reload shown in FIG. 1A in a non-articulated and unapproximated position with the proximal tube of the proximal body portion and the shaft tube of the shaft portion removed.

Referring also to FIGS. 19 and 20, when the cartridge channels 140a and 140b are positioned about the legs 188 of the cartridge body 184 and secured to the cartridge body 184, a space "s" (FIG. 32) is defined between sidewalls of the legs 188 of the cartridge body 184 and inner walls of the cartridge channels 140a, 140b. The staple legs 200a, 200b are positioned in the space "s". In addition, the cam surfaces 222a, 222b of each of the firing cams 138a and 138b are slidably supported in the spaces "s". When the firing cams 138a, 138b are advanced distally from a retracted position to an advanced position, the cam surfaces 222a, 222b are moved between the legs 188 and the cartridge channels 140a, 140b into sequential contact with the legs 200a, 200b of the staples 185 (FIG. 18) to urge the staples 185 from the cartridge body 184 into the staple forming depressions 182b (FIG. 22A) of the anvil 182 as described in further detail below.

Referring to FIGS. 3C and 21-25B, the anvil 182 defines an elongated slot 252 and an elongated recess 254. The vertical strut 156 (FIG. 25B) of the working member 150 passes through the elongated slot 252 such that the upper beam 152 is slidably positioned in the elongated recess 254 of the anvil 182. A proximal end of the anvil 182 defines a tapered cam surface 256 (FIG. 22A) which is positioned in engagement with a distal end of the upper beam 152 of the working member 150 when the anvil 182 is in the open position as shown in FIG. 22A. The lower beam 154 is positioned to move along the bottom surface of the cartridge channels 140a, 140b. As shown, the anvil 182 is biased to an open position by a biasing member, e.g., one or more leaf springs 400 (FIG. 3C). In embodiments, the leaf springs 400 have a U-shaped proximal end 402 compressed between a proximal end of the cartridge body 184 and a distal face of the pivot member 157. A distal end of the leaf springs 400 engages an undersurface of the anvil 182 to urge the anvil 182 to the open position.

Referring briefly again to FIG. 3, the reload 100 includes a locking member 300 which is rotatably supported about a proximal end of the inner housing 116 of the proximal body portion 110. The locking member 300 is movable from a first position in which the locking member 300 blocks distal movement of the proximal drive member 118 to a second position in which the locking member 300 moves to a position to allow distal movement of the proximal drive member 118. U.S. Pat. No. 7,143,924 describes the locking member 300 and its method of operation in detail and is incorporated herein by reference in its entirety.

Figure 22B:
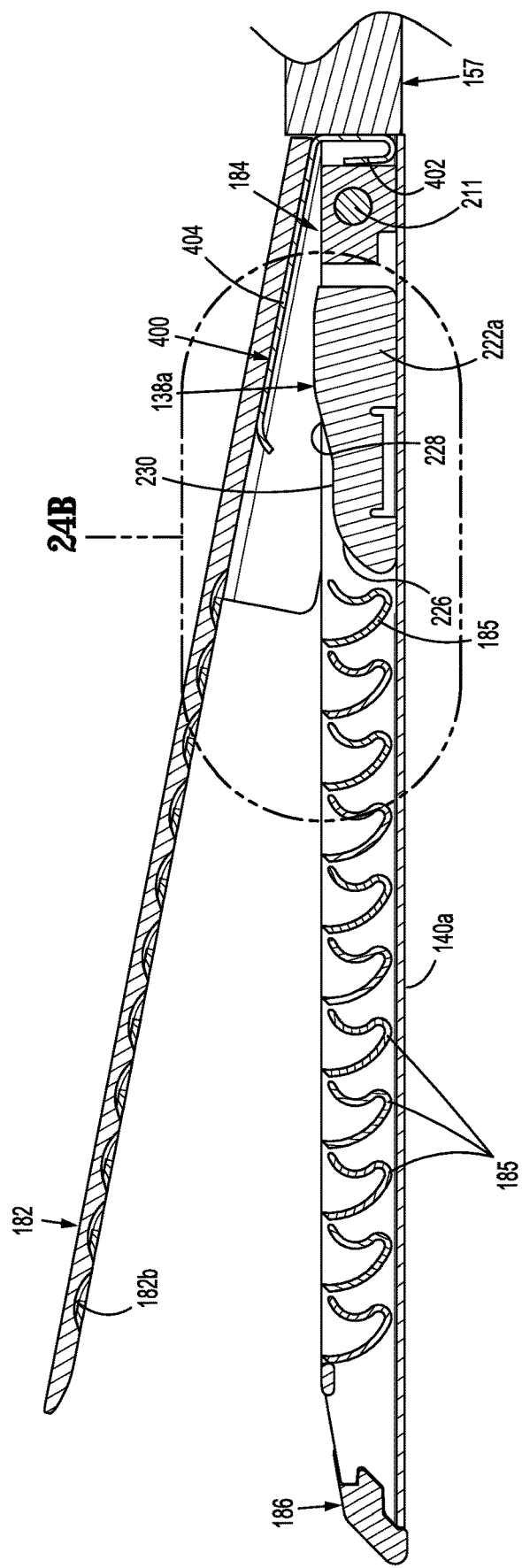
FIG. 22B is a cross-sectional view taken along section line 22B-22B of FIG. 21.
Figure 23A:
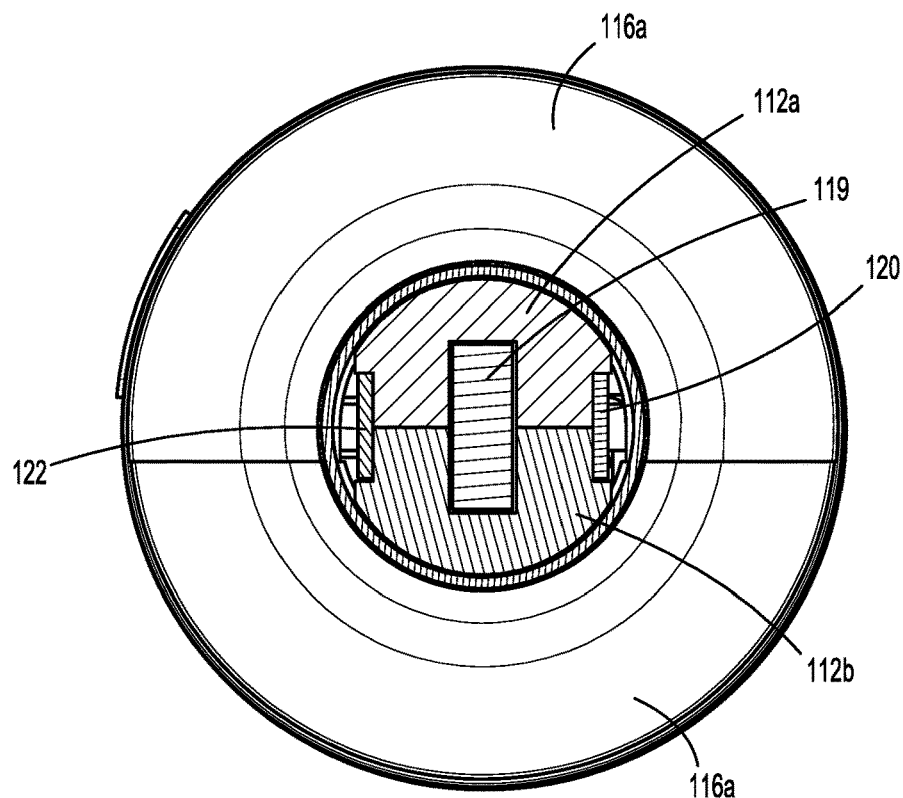
FIG. 23A is a cross-sectional view taken along section line 23A-23A of FIG. 21.
Figure 23B:
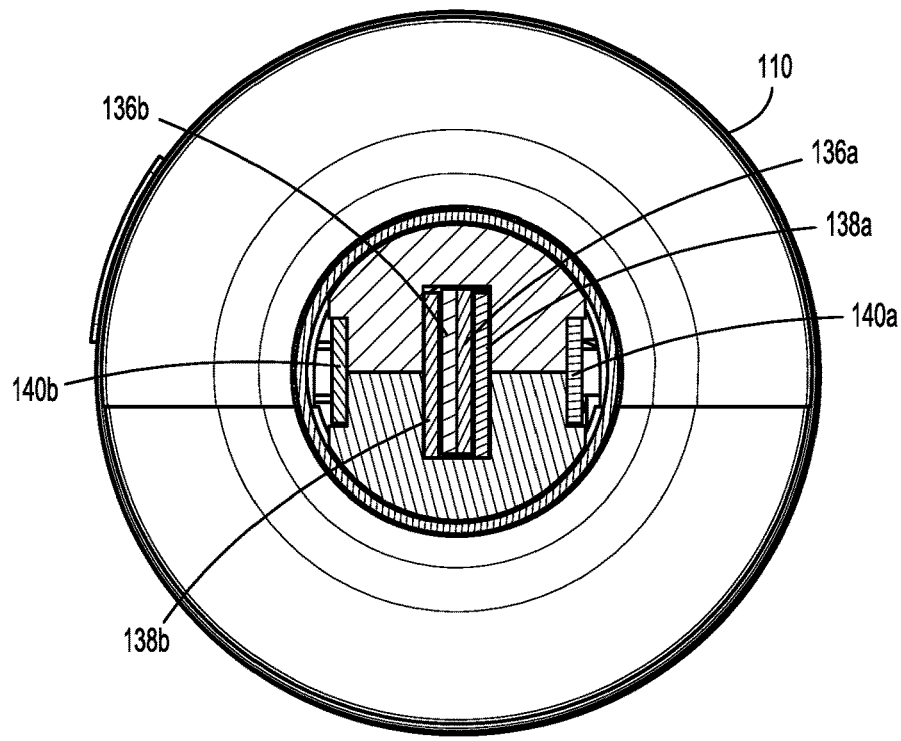
FIG. 23B is a cross-sectional view taken along section line 23B-23B of FIG. 21.
Figure 24A:
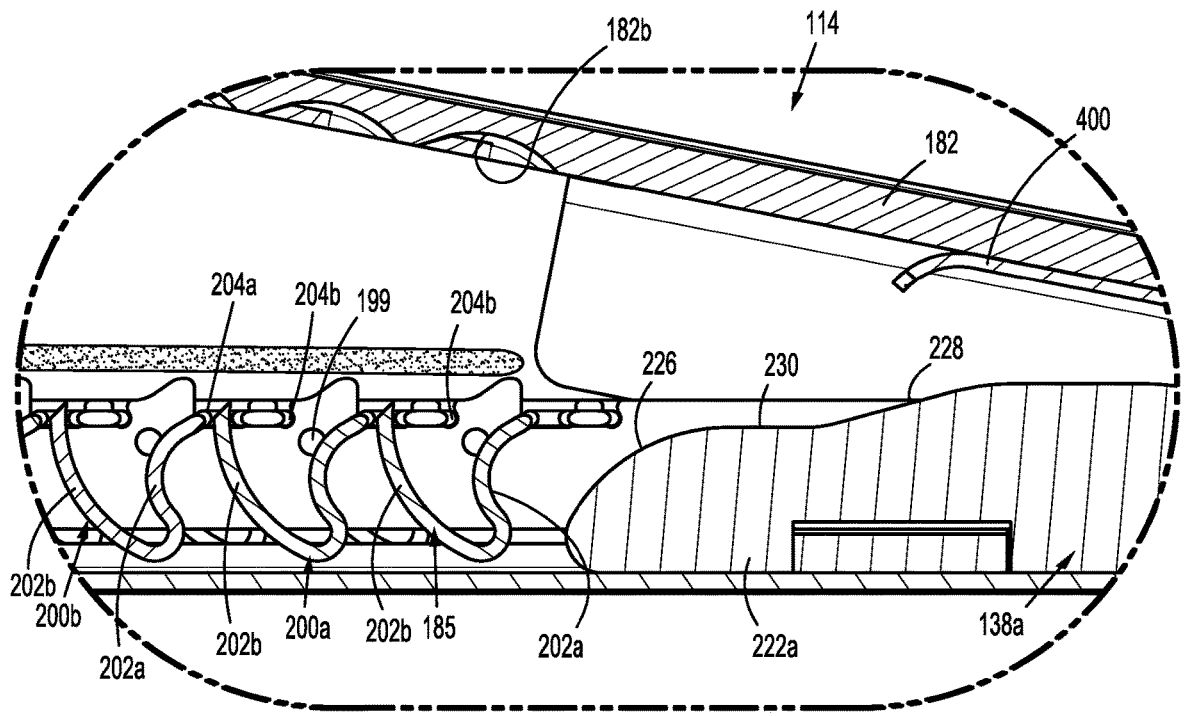
FIG. 24A is an enlarged view of the indicated area of detail shown in FIG. 22A.
Figure 24B:
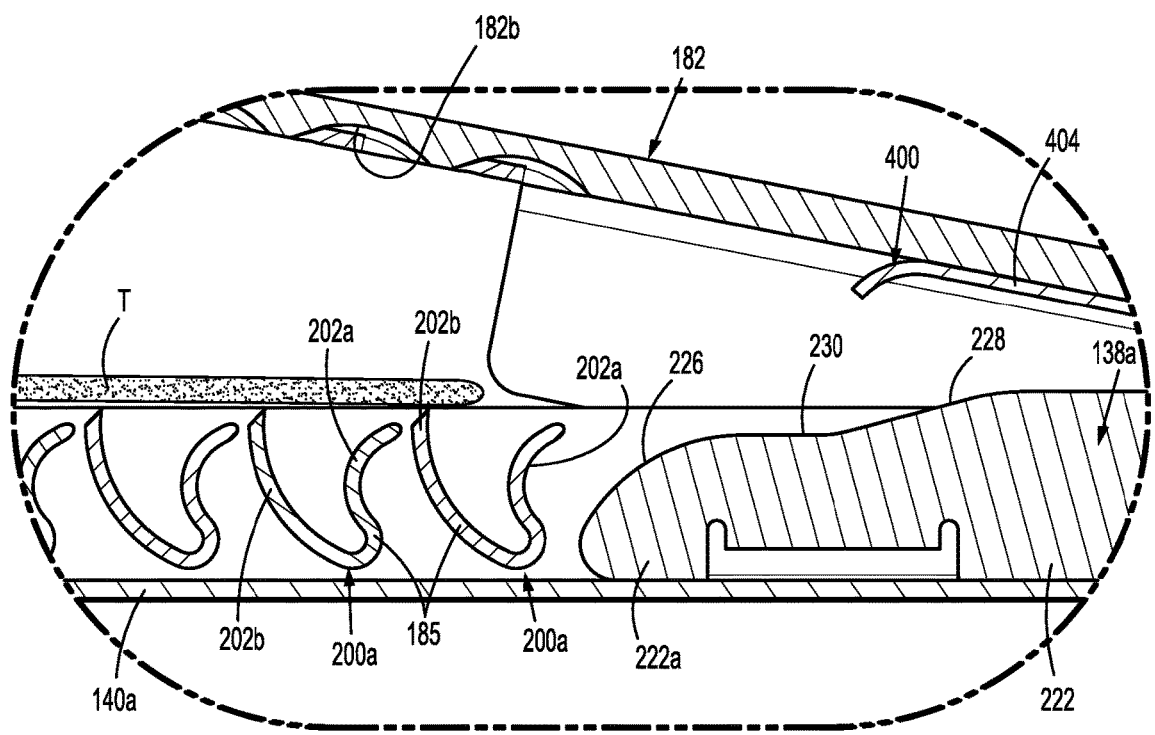
FIG. 24B is an enlarged view of the indicated area of detail shown in FIG. 22B.
Figure 26:
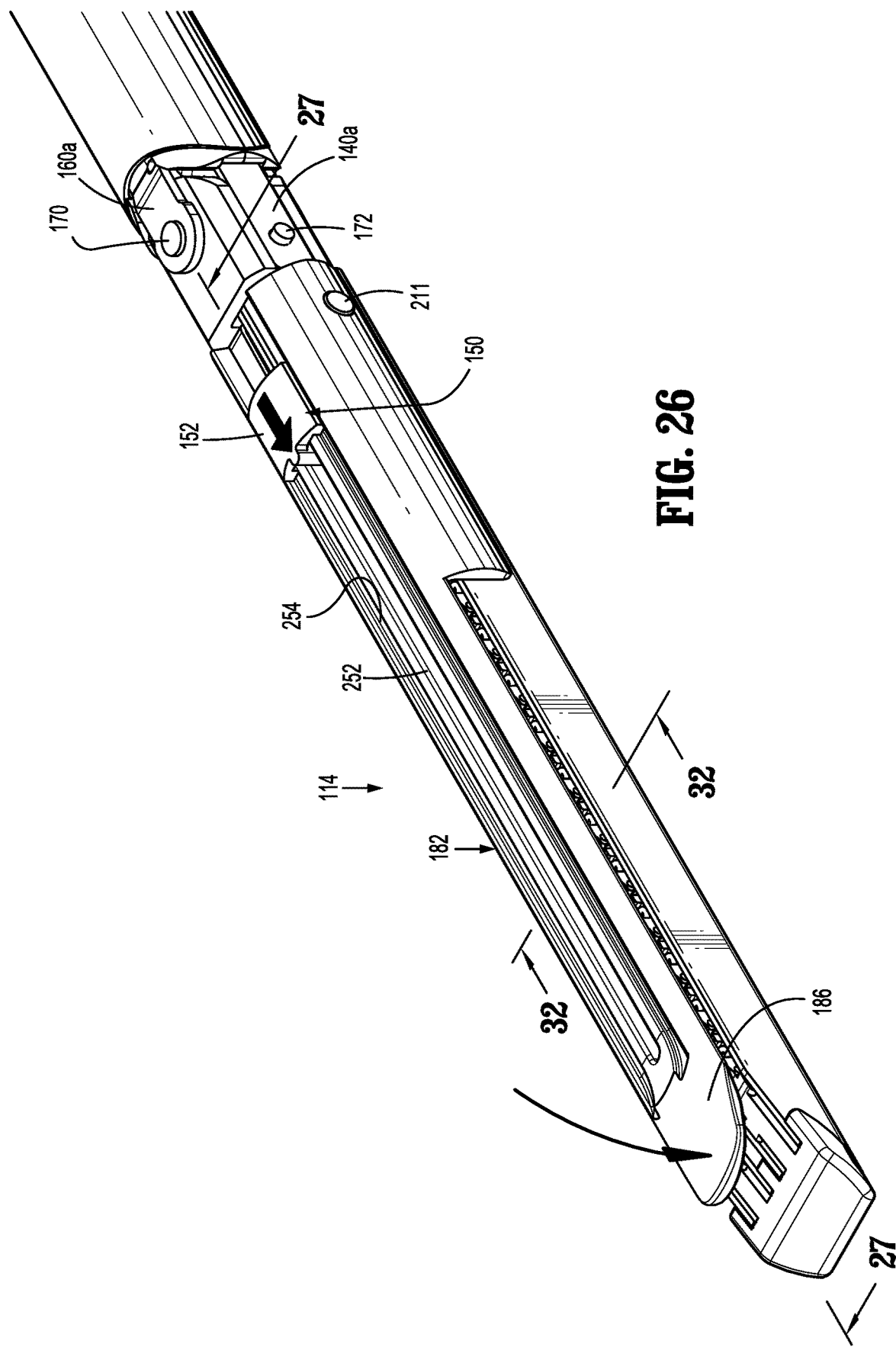
FIG. 26 is a top, perspective view of the tool assembly of the stapler reload shown in FIG. 21 with the tool assembly in the approximated position and the firing cams advanced into engagement with a proximal-most staple of the plurality of staples.

Referring again to FIGS. 3 and 21-25B, when the proximal drive member 118 (FIG. 3) is in a retracted position, the drive member link 119 and, thus, the distal drive members 136a, 136b and the firing cam 138a, 138b are also in a retracted position (FIG. 25B). In the retracted position, the hook portion 119a is engaged with the hook portions 144a, 146a of the distal drive members 136a, 136b and the firing cams 138a, 138b, respectively, and is positioned within the proximal end of the recesses 144b, 146b of the distal drive members 136a, 136b and the firing cams 138a, 138b. In addition, the distal end of the upper beam 152 of the working member 150 is positioned proximally of the tapered cam surface 256 (FIG. 22A) of the anvil 182 to allow the biasing members 400 to position or move the anvil 182 to the open position spaced from the cartridge body 184 (FIG. 22A). In the retracted position of the firing cams 138a, 138b, the cam surfaces 222a, 222b (FIG. 20) of each of the firing cams 138a, 138b is positioned proximally of the a respective leg 200a, 200b of the proximal-most staple 185 (FIG. 24A) such that a proximal end 259 (FIG. 18) of cam surface 222b of each firing cam 138a, 138b is in abutment with a shoulder 260 (FIG. 6) of a respective leg 188 of the cartridge body 184. Referring to FIG. 26, when the proximal drive member 118 is advanced via operation of the actuating device 12 (FIG. 1), the hook portion 119a of the drive member link 119 translates through the recesses 144b, 146b of the distal drive members 136a, 136b and of the firing cams 138a, 138b. The recesses 146b of the firing cams 138a, 138b extend distally of the recesses 144b of the distal drive members 136a, 136b. When the hook member 119a of the drive member link 119 engages a wall 144c, 146c defining a distal end of the recesses 144b and 146b of the distal drive members 136a, 136b and the firing cams 138a, 138b, respectively, distal movement of the drive member link 119 will effect corresponding distal movement of the distal drive members 136c, 136b and the firing cams 138a, 138b. As discussed above, the wall 146c defining the distal end of each of the recesses 146b is positioned distally of the wall 144c defining the distal end of each of the recesses 144b of the distal drive members 136a, 136b. As such, distal movement of the drive member link 119 will cause movement of the distal drive members 136a, 136b before causing distal movement of the firing cams 138a, 138b.

Figure 27:
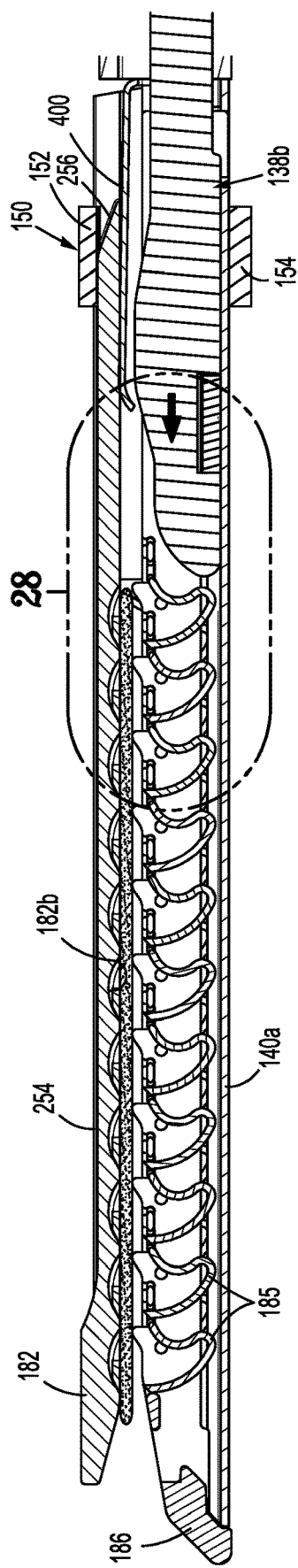
FIG. 27 is a side, cross-sectional view of the tool assembly of the stapler reload shown in FIG. 26.
Figure 28:
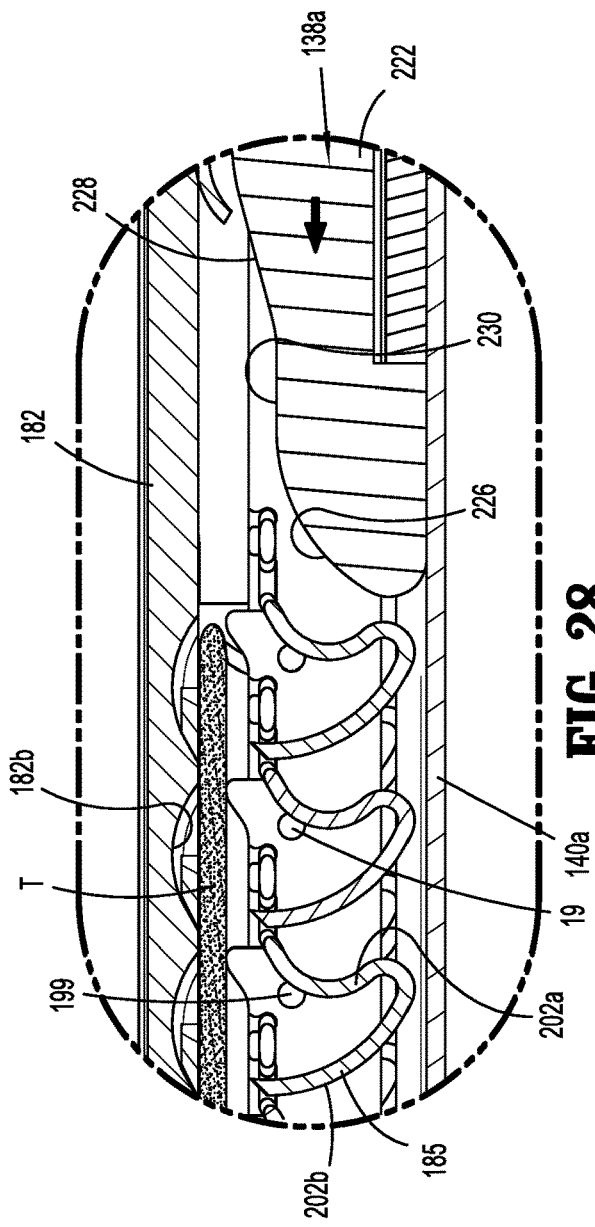
FIG. 28 is an enlarged view of the indicated area of detail shown in FIG. 27.
Figure 29:
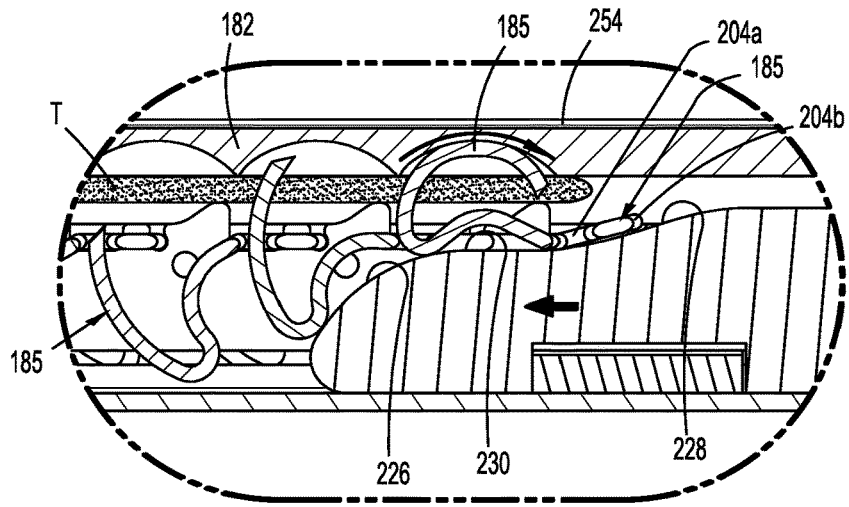
FIG. 29 is a view of the area of detail shown in FIG. 28 with the firing cams advanced into engagement with a second proximal-most staple.

When the distal drive members 136a, 136b are advanced via the drive member link 119, the working member 150 is advanced in relation to the anvil 182. As the working member 150 is advanced, the upper beam 152 of the working member 150 (FIG. 27) is moved over the tapered cam surface 256 (FIG. 27) of the anvil 182 to pivot the anvil 182 to an approximated position (FIG. 26). In the approximated position, the distal end of the cam surfaces 222a, 222b of each of the firing cams 138a, 138b are positioned immediately proximal of or in contact with the proximal leg portion 202a of the proximal-most staple of the plurality of staples 185.

Referring to FIGS. 27-33, continued advancement of the proximal drive member 118 (FIG. 25), will subsequently move the cam surfaces 222a, 222b (only 222b is shown in FIGS. 29-33) of each of the firing cams 138a, 138b sequentially into contact with the staples 185. More particularly, when the firing cams 138a, 138b are advanced about legs 188 of cartridge body 184, the cam surfaces 222a, 222b sequentially engage the proximal leg portions 202a of the staples 185 to rotate or pivot the staples 185 about the proximal portion 204b of the intermediate portion 201 within the notches 198. As the first curved cam surface 226 of cam surfaces 222a, 222b moves under the proximal leg portion 202a of each staple 185, each staple 185 is pivoted or rotated upwardly to direct the tapered tip 202c of the staple 185 into a staple forming depression 182b of the anvil 182 to initiate deformation of the staple 186 FIG. 28).

After the first curved cam surface 226 of the cam surfaces 222a, 222b moves past the proximal leg portion 202a of the staple 185, the plateau 230 of the cam surfaces 222a, 222b moves under the proximal leg portion 202a of the staple 185. The height of the plateau 230 is less than the height of the rectangular cutouts 196 and the base 198a of the notches 198. As such, at this stage of advancement of the firing cams 138a, 138b, the proximal-most staples 185 remain engaged with the legs 188 of the cartridge body 184.

Figure 30:
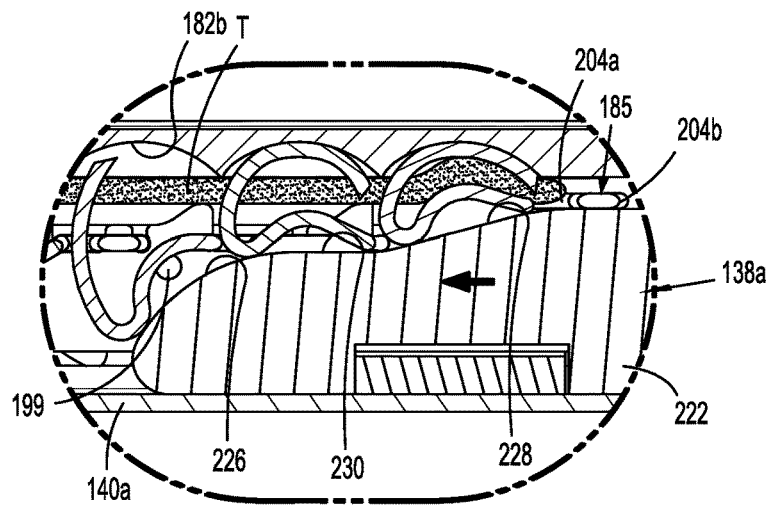
FIG. 30 is a view of the area of detail shown in FIG. 29 with the firing cams advanced into engagement with a third proximal-most staple.
Figure 30A:
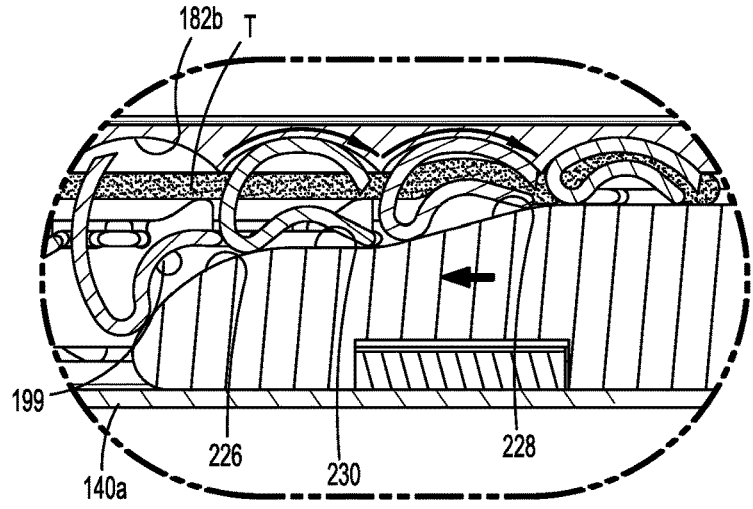
FIG. 30A is a view of the area of detail shown in FIG. 30 with the firing cam advanced into engagement with the fourth proximal-most staple and the proximal-most staple disengaged from the cartridge body.
Figure 31:
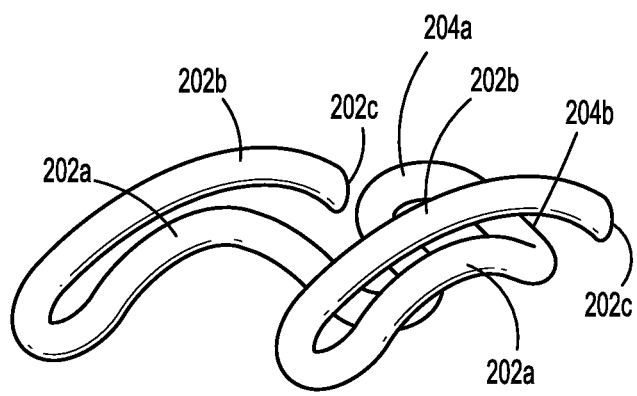
FIG. 31 is a perspective view of a staple of the tool assembly of the stapler reload shown in FIG. 26 after the staple has been deformed.

Upon continued advancement of the firing cams 138a, 138b, the second curved surface 228 of each of the cam surfaces 222a, 222b moves under the staples 185. Engagement of the second curved surface 228 of the cam surfaces 222a, 222b fully deforms the staple 185 and disengages or separates each staple 185 from the notches 198 of the legs 188 of the cartridge body 184. In that respect, the height at the proximal end of the second curved surface 228 of the cam surfaces 222a, 222b is greater that the height of the cutouts 196 and the base 198a of the notches 198. As discussed above, the staple legs 200a and 200b of each staple 185 and the cam surfaces 222a and 222b of each of the firing cams 138a and 138b are staggered or offset axially. In embodiments, the degree of offset of the staple legs 200a and 200b is equal to the degree of offset of the cam surfaces 222a and 222b such that the cam surfaces 222a engage the legs 200a of a staple 185 at the same time that the cam surfaces 222b engage the legs 200b of the staple 185. As shown in FIGS. 30 and 31, the legs 200a, 200b of the fully formed staple 185 have substantially D-shape configurations and are axially offset from each other.

Referring to FIGS. 3-3C and 33-37, the tool assembly 114 can be articulated by movement of the cartridge channels 140a, 140b in opposite directions in relation to each other. As discussed above, the cartridge channels 140a, 140b extend from the proximal body portion 110 through the elongated shaft portion 112 to the tool assembly 114. A distal end of each of the cartridge channels 140a, 140b is connected to the pivot member 157 by respective posts 172 (FIG. 3A) that extend through the proximal openings 210a of the cartridge channels 140a, 140b. The proximal ends of the cartridge channels 140a, 140b include cutouts 142a, 142b (FIG. 3B), respectively, that receive one side of hook portions 120a, 122a of the articulation rods 120, 122, respectively, to connect the articulation rods 120, 122 to the cartridge channels 140a, 140b. The first and second articulation links 120, 122 are slidably supported between the housing halves 116a, 116b of the proximal body portion 110. The first articulation link 120 has a distal end connected to the cartridge channel 140a and a proximal end connected to an articulation assembly 350 (FIG. 1) of the actuating device 12 (FIG. 1).

The articulation member 123 includes a C-shaped body 302 having spaced fingers 304, 306 and a central opening 308 (FIG. 34). The fingers 304, 306 are received in cutouts 310 formed in the distal end of first and second articulation links 120 and 122. The central opening 308 receives a housing post 312 (FIG. 35) formed on housing half 116b of the central body portion 110 (FIG. 1) such that movement of the first articulation link 120 in one direction as indicated by arrow "A" in FIG. 36 causes the articulation member 123 to pivot about the housing post 312 to cause movement of the second articulation link 122 in a second direction as indicated by arrow "B" in FIG. 37.

In use, when the first articulation link 120 is moved by the articulation assembly 350 in direction A, the cartridge channel 140a, which is axially fixed to the first articulation link 120 by placement of hook portion 120a in cutout 142a (FIG. 3B), is also moved in direction A. Movement of the first articulation link 120 in direction A effects pivotal movement of the articulation member 123 which causes movement of the second articulation link 122 in the direction of arrow B. Movement of the second articulation link 122 in direction of arrow B causes movement of cartridge channel 140b in the direction of arrow B.

As discussed above, the distal ends of cartridge channels 140a and 140b are connected to opposite sides of the pivot member 157 by posts 172. As the cartridge channels 140a, 140b are moved in opposite directions, the pivot member 157 is pivoted about the pivot pin 170 to pivot the tool assembly 114 in relation to shaft portion 112 such that the longitudinal axis of the tool assembly 114 moves from a position aligned with the longitudinal axis of the shaft portion 112 (FIG. 33) to a position at an angle to the longitudinal axis of the shaft portion 112. It is noted that the cartridge channels 140a, 140b, the firing cams 138a, 138b and the distal drive members 136a, 136b are all formed of a resilient material such as spring steel to facilitate movement about the axis of articulation, i.e., the axis of the pivot pin 170, to an articulated position.

Persons skilled in the art will understand that the devices and methods specifically described herein and illustrated in the accompanying drawings are non-limiting exemplary embodiments. It is envisioned that the elements and features illustrated or described in connection with one exemplary embodiment may be combined with the elements and features of another without departing from the scope of the present disclosure. As well, one skilled in the art will appreciate further features and advantages of the disclosure based on the above-described embodiments. Accordingly, the disclosure is not to be limited by what has been particularly shown and described, except as indicated by the appended claims.

What is claimed is:

1. A surgical staple comprising:
   a first curved leg having a proximal leg portion having a proximal end and a distal leg portion having a distal end;
   a second curved leg having a proximal leg portion having a proximal end and a distal leg portion having a distal end; and
   an intermediate portion defining and lying within a plane, the intermediate portion having a first end connected to the proximal end of the proximal leg portion of the first curved leg and a second end connected to the proximal end of the proximal leg portion of the second curved leg;
   wherein the distal ends of the first and second curved legs are positioned distally of and on the same side of the intermediate portion, the first and second ends of the intermediate portion being axially offset from each other, and wherein the distal leg portions of the first and second curved legs extend from the proximal leg portions upwardly towards the plane defined by the intermediate portion.

2. The surgical staple according to claim 1, wherein the intermediate portion of the surgical staple is S-shaped and includes a distal U-shaped portion and a proximal U-shaped portion.

3. The surgical staple according to claim 1, wherein each of the first and second legs includes a tapered tip.

4. The surgical staple according to claim 1, wherein each of the first and second legs is configured to have a D-shape when formed against an anvil.

5. A cartridge assembly comprising:
   a cartridge body having spaced legs, each of the spaced legs defining a longitudinal axis and having a plurality of notches and a plurality of cutouts spaced along the longitudinal axis, the plurality of notches and the plurality of cutouts alternatingly positioned on each of the spaced legs along the longitudinal axis of the respective legs; and
   a plurality of staples, each of the plurality of staples including first and second curved legs and an intermediate portion interconnecting the first and second curved legs, the intermediate portion of each of the plurality of staples including a U-shaped portion that is received within one of the plurality of cutouts on one of the spaced legs of the cartridge body to secure the respective one of the plurality of staples to the respective one of the spaced legs.

6. The cartridge assembly of claim 5, wherein the intermediate portion of each of the plurality of staples includes the U-shaped portion and a proximal portion positioned proximally of the U-shaped portion, the proximal portion of each of the plurality of staples rotatably received within a respective one of the notches.

7. The cartridge assembly of claim 6, wherein the proximal portion of each of the plurality of staples is U-shaped and the intermediate portion of each of the plurality of staples is S-shaped.

8. The cartridge assembly of claim 6, wherein the proximal portion of each of the plurality of staples is snap-fit into the respective one of the notches to rotatably secure the plurality of staples to the cartridge body.

9. The cartridge assembly of claim 6, wherein each of the spaced legs of the cartridge body includes a plurality of spaced dimples, each of the plurality of dimples engaging one of the first and second curved legs of a respective one of the plurality of staples to secure the plurality of staples within the cartridge assembly.

10. The cartridge assembly of claim 6, wherein the plurality of staples are supported along the longitudinal axes of the spaced legs of the cartridge body.

11. The cartridge assembly of claim 6, wherein the first and second curved legs of each of the plurality of staples includes a tapered tip.

12. The cartridge assembly of claim 6, wherein the first and second curved legs of each of the plurality of staples extends along the longitudinal axes of the spaced legs of the cartridge body.

13. The cartridge assembly of claim 6, wherein the cartridge body includes a tapered distal end, the tapered distal end interconnecting the spaced legs of the cartridge body.

14. The cartridge assembly of claim 6, wherein the first and second legs of each of the plurality of staples includes a distal end and a proximal end, the distal ends of each of the first and second curved legs positioned distally of the intermediate portion, and the intermediate portion of the surgical staple connecting the proximal ends of the first and second curved legs, wherein the first and second ends of the intermediate portion are axially offset from each other.

15. The cartridge assembly according to claim 6, wherein the first and second curved legs of each of the plurality of staples are configured to have a D-shape when formed against an anvil.

16. The cartridge assembly according to claim 6, wherein the curved legs of each of the plurality of staples is positioned on opposite sides of one of the respective spaced legs of the cartridge body.

* * * * *